US011141158B2

(12) United States Patent
Ketai et al.

(10) Patent No.: US 11,141,158 B2
(45) Date of Patent: Oct. 12, 2021

(54) INDEPENDENT GRIPPER

(71) Applicant: ABBOTT CARDIOVASCULAR SYSTEMS INC., Santa Clara, CA (US)

(72) Inventors: Theodore W. Ketai, San Francisco, CA (US); Jacob Greenberg, Mountain View, CA (US); Daniel Hale, Belmont, CA (US); Tanmay Mishra, Philadelphia, PA (US); Gabriel Gonzales, Milpitas, CA (US); Raghuveer Basude, Fremont, CA (US); Michael Hong, San Francisco, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 292 days.

(21) Appl. No.: 15/998,518

(22) Filed: Aug. 16, 2018

(65) Prior Publication Data

US 2019/0053803 A1    Feb. 21, 2019

Related U.S. Application Data

(60) Continuation of application No. 14/643,718, filed on Mar. 10, 2015, now abandoned, which is a division of
(Continued)

(51) Int. Cl.
*A61B 17/08* (2006.01)
*A61F 2/24* (2006.01)
(Continued)

(52) U.S. Cl.
CPC .............. *A61B 17/08* (2013.01); *A61B 17/10* (2013.01); *A61F 2/2454* (2013.01); *A61F 2/2466* (2013.01); *A61B 2017/00243* (2013.01)

(58) Field of Classification Search
CPC ...... A61F 2/246; A61F 2/2466; A61F 2/2454; A61B 17/122; A61B 17/0643;
(Continued)

(56) References Cited

U.S. PATENT DOCUMENTS 3,378,010 A    4/1968 Codling et al.
3,874,388 A *  4/1975 King .................. A61B 17/0057
606/232
(Continued)

FOREIGN PATENT DOCUMENTS

CA    2 296 317 C    1/2009
EP    0 558 031 B1    9/1993
(Continued)

OTHER PUBLICATIONS

European Search Report dated Apr. 23, 2020 in Application No. EP 19219129.
(Continued)

*Primary Examiner* — Kathleen S Holwerda
(74) *Attorney, Agent, or Firm* — Baker Botts L.L.P.

(57) ABSTRACT

The invention provides devices, systems and methods for tissue approximation and repair at treatment sites. The devices, systems and methods of the invention will find use in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The invention is particularly useful in those procedures requiring minimally-invasive or endovascular access to remote tissue locations, where the instruments utilized must negotiate long, narrow, and tortuous pathways to the treatment site. In addition, many of the devices and systems of the invention are adapted to be
(Continued)

reversible and removable from the patient at any point without interference with or trauma to internal tissues.

23 Claims, 44 Drawing Sheets

Related U.S. Application Data application No. 13/231,572, filed on Sep. 13, 2011, now Pat. No. 9,011,468.

(51) Int. Cl.
*A61B 17/10* (2006.01)
*A61B 17/00* (2006.01)

(58) Field of Classification Search
CPC ....... A61B 17/08; A61B 17/10; A61B 17/083; A61B 2017/00579; A61B 2017/00606; A61B 2017/00243
See application file for complete search history.

(56) References Cited

U.S. PATENT DOCUMENTS

| | | | |
|---|---|---|---|
| 4,007,743 | A * | 2/1977 | Blake ............ A61B 17/0057 606/232 |
| 4,055,861 | A | 11/1977 | Carpentier et al. |
| 4,327,736 | A | 5/1982 | Inoue |
| 4,340,091 | A | 7/1982 | Skelton et al. |
| 4,657,024 | A | 4/1987 | Coneys |
| 4,693,248 | A | 9/1987 | Failla |
| 4,716,886 | A | 1/1988 | Schulman et al. |
| 4,795,458 | A | 1/1989 | Regan |
| 4,809,695 | A | 3/1989 | Gwathmey et al. |
| 4,930,674 | A | 6/1990 | Barak |
| 5,002,562 | A | 3/1991 | Oberlander |
| 5,069,679 | A | 12/1991 | Taheri |
| 5,098,440 | A | 3/1992 | Hillstead |
| 5,125,895 | A | 6/1992 | Buchbinder et al. |
| 5,147,370 | A | 9/1992 | McNamara et al. |
| 5,171,259 | A | 12/1992 | Inoue |
| 5,222,963 | A | 6/1993 | Brinkerhoff et al. |
| 5,271,544 | A | 12/1993 | Fox et al. |
| 5,327,905 | A | 7/1994 | Avitall |
| 5,330,501 | A | 7/1994 | Tovey et al. |
| 5,334,217 | A | 8/1994 | Das |
| 5,363,861 | A | 11/1994 | Edwards et al. |
| 5,389,077 | A | 2/1995 | Melinyshyn et al. |
| 5,403,326 | A | 4/1995 | Harrison et al. |
| 5,425,744 | A | 6/1995 | Fagan et al. |
| 5,450,860 | A | 9/1995 | O'Connor |
| 5,452,837 | A | 9/1995 | Williamson, IV et al. |
| 5,456,400 | A | 10/1995 | Shichman et al. |
| 5,456,674 | A | 10/1995 | Bos et al. |
| 5,478,353 | A | 12/1995 | Yoon |
| 5,542,949 | A | 8/1996 | Yoon |
| 5,562,678 | A | 10/1996 | Booker |
| 5,601,224 | A | 2/1997 | Bishop et al. |
| 5,601,574 | A | 2/1997 | Stefanchik et al. |
| 5,607,462 | A | 3/1997 | Imran |
| 5,607,471 | A | 3/1997 | Seguin et al. |
| 5,609,598 | A | 3/1997 | Laufer et al. |
| 5,611,794 | A | 3/1997 | Sauer et al. |
| 5,636,634 | A | 6/1997 | Kordis et al. |
| 5,695,504 | A | 12/1997 | Gifford, III et al. |
| 5,713,911 | A | 2/1998 | Racenet et al. |
| 5,716,417 | A | 2/1998 | Girard et al. |
| 5,741,297 | A | 4/1998 | Simon |
| 5,755,778 | A | 5/1998 | Kleshinski |
| 5,782,239 | A | 7/1998 | Webster, Jr. |
| 5,797,960 | A | 8/1998 | Stevens et al. |
| 5,810,847 | A | 9/1998 | Laufer et al. |
| 5,814,097 | A | 9/1998 | Sterman et al. |
| 5,843,178 | A | 12/1998 | Vanney et al. |
| 5,849,019 | A | 12/1998 | Yoon |
| 5,855,601 | A | 1/1999 | Bessler et al. |
| 5,976,159 | A | 11/1999 | Bolduc et al. |
| 6,015,417 | A | 1/2000 | Reynolds, Jr. |
| 6,048,351 | A | 4/2000 | Gordon et al. |
| 6,079,414 | A | 6/2000 | Roth |
| 6,117,144 | A | 9/2000 | Nobles et al. |
| 6,120,496 | A | 9/2000 | Whayne et al. |
| 6,149,658 | A | 11/2000 | Gardiner et al. |
| 6,156,055 | A | 12/2000 | Ravenscroft |
| 6,165,183 | A | 12/2000 | Kuehn et al. |
| 6,182,664 | B1 | 2/2001 | Cosgrove |
| 6,193,734 | B1 | 2/2001 | Bolduc et al. |
| 6,200,315 | B1 | 3/2001 | Gaiser et al. |
| 6,217,528 | B1 | 4/2001 | Koblish et al. |
| 6,269,819 | B1 | 8/2001 | Oz et al. |
| 6,290,674 | B1 | 9/2001 | Roue et al. |
| 6,312,447 | B1 | 11/2001 | Grimes |
| 6,332,880 | B1 | 12/2001 | Yang et al. |
| 6,346,074 | B1 | 2/2002 | Roth |
| 6,419,696 | B1 | 7/2002 | Ortiz et al. |
| 6,461,366 | B1 | 10/2002 | Seguin |
| 6,482,224 | B1 | 11/2002 | Michler et al. |
| 6,496,420 | B2 | 12/2002 | Manning |
| 6,544,215 | B1 | 4/2003 | Bencini et al. |
| 6,551,303 | B1 | 4/2003 | Van Tassel et al. |
| 6,575,971 | B2 | 6/2003 | Hauck et al. |
| 6,599,311 | B1 | 7/2003 | Biggs et al. |
| 6,626,930 | B1 | 9/2003 | Allen et al. |
| 6,629,534 | B1 | 10/2003 | St. Goar et al. |
| 6,669,687 | B1 | 12/2003 | Saadat |
| 6,695,866 | B1 | 2/2004 | Kuehn et al. |
| 6,719,767 | B1 | 4/2004 | Kimblad |
| 6,752,813 | B2 | 6/2004 | Goldfarb et al. |
| 6,770,083 | B2 | 8/2004 | Seguin |
| 6,797,002 | B2 | 9/2004 | Spence et al. |
| 6,837,867 | B2 | 1/2005 | Kortelling |
| 6,855,137 | B2 | 2/2005 | Bon |
| 6,875,224 | B2 | 4/2005 | Grimes |
| 6,908,481 | B2 | 6/2005 | Cribier |
| 6,926,730 | B1 | 8/2005 | Nguyen et al. |
| 7,011,669 | B2 | 3/2006 | Kimblad |
| 7,101,395 | B2 | 9/2006 | Tremulis et al. |
| 7,112,207 | B2 | 9/2006 | Allen et al. |
| 7,125,421 | B2 | 10/2006 | Tremulis et al. |
| 7,226,467 | B2 | 6/2007 | Lucatero et al. |
| 7,556,632 | B2 | 7/2009 | Zadno |
| 7,563,267 | B2 | 7/2009 | Goldfarb et al. |
| 7,569,062 | B1 | 8/2009 | Kuehn et al. |
| 7,604,646 | B2 | 10/2009 | Goldfarb et al. |
| 7,635,329 | B2 | 12/2009 | Goldfarb et al. |
| 7,655,015 | B2 | 2/2010 | Goldfarb et al. |
| 7,666,204 | B2 | 2/2010 | Thornton et al. |
| 7,704,269 | B2 | 4/2010 | St. Goar et al. |
| 7,736,388 | B2 | 6/2010 | Goldfarb et al. |
| 7,798,953 | B1 | 9/2010 | Wilk |
| 7,811,296 | B2 | 10/2010 | Goldfarb et al. |
| 7,972,323 | B1 | 7/2011 | Bencini et al. |
| 7,972,330 | B2 | 7/2011 | Alejandro et al. |
| 7,981,139 | B2 | 7/2011 | Martin et al. |
| 8,057,493 | B2 | 11/2011 | Goldfarb et al. |
| 8,062,313 | B2 | 11/2011 | Kimblad |
| 8,118,822 | B2 | 2/2012 | Schaller et al. |
| 8,216,230 | B2 | 7/2012 | Hauck et al. |
| 8,216,256 | B2 | 7/2012 | Raschdorf, Jr. et al. |
| 8,303,608 | B2 | 11/2012 | Goldfarb et al. |
| 8,500,761 | B2 | 8/2013 | Goldfarb et al. |
| 8,608,795 | B2 | 12/2013 | Melsheimer et al. |
| 8,734,505 | B2 | 5/2014 | Goldfarb et al. |
| 8,740,920 | B2 | 6/2014 | Goldfarb et al. |
| 9,510,829 | B2 | 12/2016 | Goldfarb et al. |
| 10,076,415 | B1 | 9/2018 | Metchik et al. |
| 10,105,222 | B1 | 10/2018 | Metchik et al. |
| 10,123,873 | B1 | 11/2018 | Metchik et al. |
| 10,130,475 | B1 | 11/2018 | Metchik et al. |
| 10,136,993 | B1 | 11/2018 | Metchik et al. |
| 10,159,570 | B1 | 12/2018 | Metchik et al. |
| 10,231,837 | B1 | 3/2019 | Metchik et al. |
| 10,238,493 | B1 | 3/2019 | Metchik et al. |

(56) References Cited

U.S. PATENT DOCUMENTS

| | | |
|---|---|---|
| 10,245,144 B1 | 4/2019 | Metchik et al. |
| D847,983 S | 5/2019 | Ho et al. |
| 10,314,586 B2 | 6/2019 | Greenberg et al. |
| 10,413,408 B2 | 9/2019 | Krone et al. |
| 10,507,109 B2 | 12/2019 | Metchik et al. |
| 10,517,726 B2 | 12/2019 | Chau et al. |
| 10,524,792 B2 | 1/2020 | Hernandez et al. |
| 10,595,997 B2 | 3/2020 | Metchik et al. |
| 10,646,342 B1 | 5/2020 | Marr et al. |
| 10,779,837 B2 | 9/2020 | Lee et al. |
| D902,403 S | 11/2020 | Marsot et al. |
| 10,856,988 B2 | 12/2020 | McNiven et al. |
| 2002/0013571 A1 | 1/2002 | Goldfarb et al. |
| 2002/0183787 A1 | 12/2002 | Wahr et al. |
| 2003/0069593 A1 | 4/2003 | Tremulis et al. |
| 2003/0167071 A1 | 9/2003 | Martin et al. |
| 2004/0034365 A1 | 2/2004 | Lentz et al. |
| 2004/0044350 A1 | 3/2004 | Martin et al. |
| 2004/0049207 A1 | 3/2004 | Goldfarb et al. |
| 2005/0267493 A1 | 12/2005 | Schreck et al. |
| 2006/0089671 A1 | 4/2006 | Goldfarb et al. |
| 2007/0038293 A1 | 2/2007 | Goar St. et al. |
| 2007/0197858 A1 | 8/2007 | Goldfarb et al. |
| 2008/0255427 A1 | 10/2008 | Satake et al. |
| 2009/0163934 A1* | 6/2009 | Raschdorf, Jr. .. A61B 17/00234 606/139 |
| 2009/0326567 A1 | 12/2009 | Goldfarb et al. |
| 2010/0022823 A1 | 1/2010 | Goldfarb et al. |
| 2010/0121433 A1 | 5/2010 | Bolling et al. |
| 2010/0324585 A1 | 12/2010 | Miles et al. |
| 2012/0022633 A1 | 1/2012 | Olson et al. |
| 2017/0042546 A1 | 2/2017 | Goldfarb et al. |
| 2017/0049455 A1 | 2/2017 | Seguin |
| 2017/0239048 A1 | 8/2017 | Goldfarb et al. |
| 2017/0265994 A1 | 9/2017 | Krone |
| 2018/0021133 A1 | 1/2018 | Barbarino |
| 2018/0036119 A1 | 2/2018 | Wei et al. |
| 2018/0092661 A1 | 4/2018 | Prabhu |
| 2018/0146964 A1 | 5/2018 | Garcia et al. |
| 2018/0235657 A1 | 8/2018 | Abunassar |
| 2018/0242976 A1 | 8/2018 | Kizuka |
| 2018/0243086 A1 | 8/2018 | Barbarino et al. |
| 2018/0325671 A1 | 11/2018 | Abunassar et al. |
| 2018/0344460 A1 | 12/2018 | Wei |
| 2018/0353181 A1 | 12/2018 | Wei |
| 2018/0360457 A1 | 12/2018 | Ellis et al. |
| 2019/0053803 A1 | 2/2019 | Ketai et al. |
| 2019/0125536 A1 | 5/2019 | Prabhu et al. |
| 2019/0151041 A1 | 5/2019 | Ho et al. |
| 2019/0151089 A1 | 5/2019 | Wei |
| 2019/0159899 A1 | 5/2019 | Marsot et al. |
| 2019/0167197 A1 | 6/2019 | Abunassar et al. |
| 2019/0183571 A1 | 6/2019 | De Marchena |
| 2019/0209293 A1 | 7/2019 | Metchik et al. |
| 2019/0247187 A1 | 8/2019 | Kizuka |
| 2019/0274831 A1 | 9/2019 | Prabhu |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1 | 1/2020 | Dell et al. |
| 2020/0060687 A1 | 2/2020 | Hernández et al. |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0187942 A1 | 6/2020 | Wei |
| 2020/0205829 A1 | 7/2020 | Wei |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |

FOREIGN PATENT DOCUMENTS

| | | |
|---|---|---|
| EP | 1 383 448 B1 | 6/2008 |
| FR | 2 768 324 A1 | 3/1999 |
| FR | 2768324 A1 | 3/1999 |
| FR | 2 768 325 B1 | 11/1999 |
| JP | 2006528911 A | 12/2006 |
| JP | 6174103 82 | 8/2017 |
| WO | WO 91/01689 A1 | 2/1991 |
| WO | WO 92/12690 A1 | 8/1992 |
| WO | WO 94/018893 A1 | 9/1994 |
| WO | WO 96/32882 A1 | 10/1996 |
| WO | WO 97/27807 A1 | 8/1997 |
| WO | WO 98/07375 A1 | 2/1998 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | 2004103162 A2 | 12/2004 |
| WO | 2005112792 A2 | 12/2005 |
| WO | WO 2015/057289 A1 | 4/2015 |
| WO | WO 2016/178722 A1 | 11/2016 |
| WO | WO 2018/093663 A1 | 5/2018 |

OTHER PUBLICATIONS

Communication dated Sep. 19, 2018 issued by the European Patent Office; European Patent Application No. EP181732648.
International Search Report and Written Opinion issued in International Application No. PCT/US12/54381 dated Dec. 21, 2012.
International Search Report and Written Opinion issued in International Application No. PCT/US12/54363 dated Nov. 13, 2012.
Communication dated Mar. 11, 2015 from the Japanese Patent Office in counterpart application No. 2014530711.
Communication dated May 18, 2015, issued by the European Patent Office in corresponding European Application No. 12831066.1.
Communication dated Apr. 28, 2015, issued by the European Patent Office in corresponding European Application No. 12831066.1.
Communication dated Aug. 2, 2017 issued by the State Intellectual Property Office of People's Republic of China in counterpart application No. 2016108296826.
Communication dated Apr. 23, 2018 issued by the Japanese Patent Office in counterpart application No. 2017-132005.

* cited by examiner

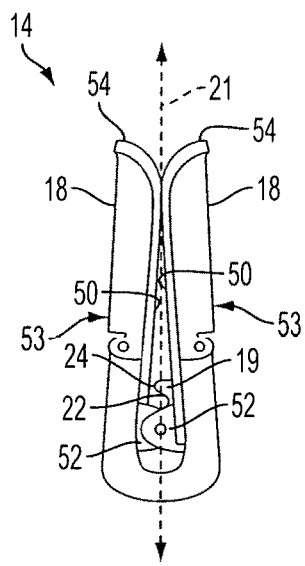
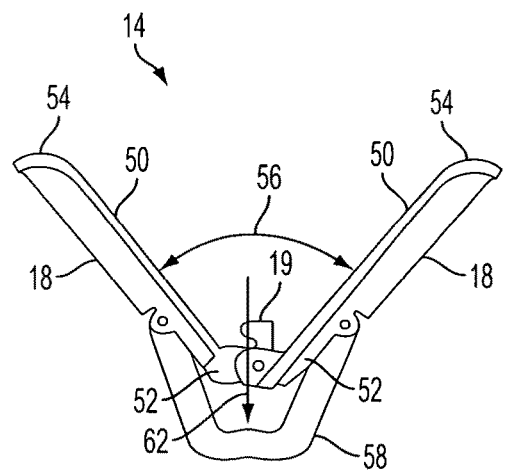
FIG. 7A    FIG. 7B
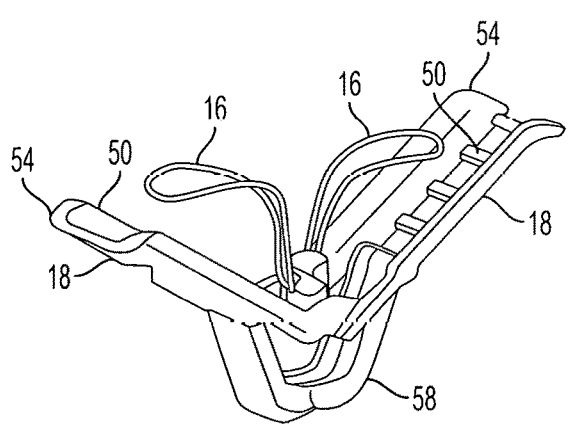
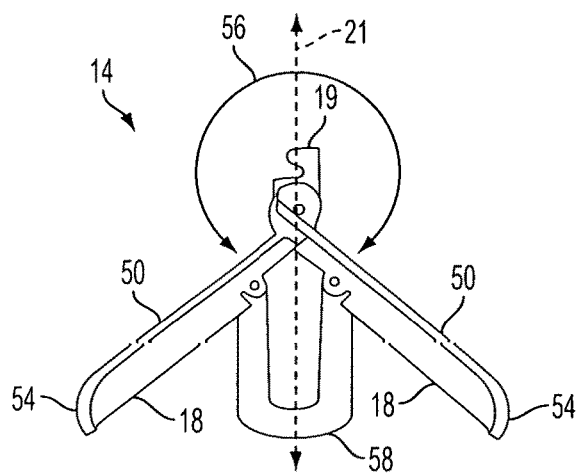
FIG. 8A    FIG. 8B

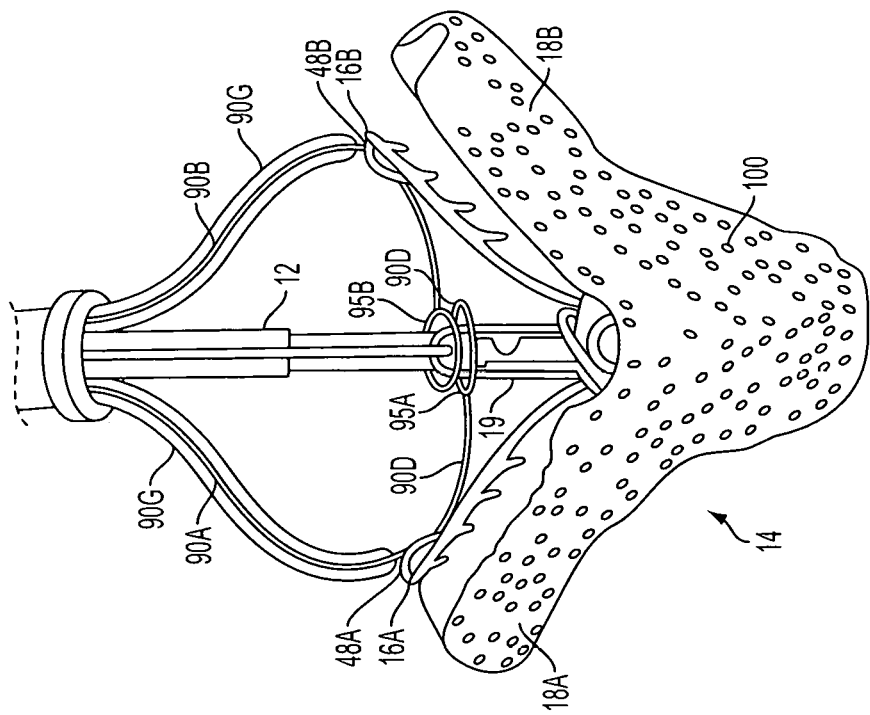
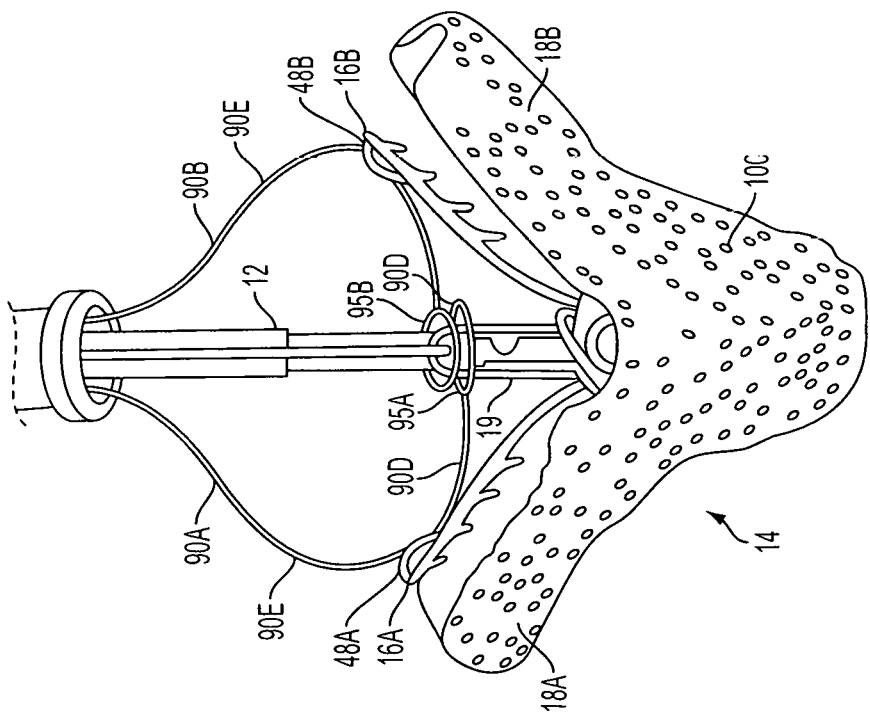
FIG. 22B
FIG. 22A

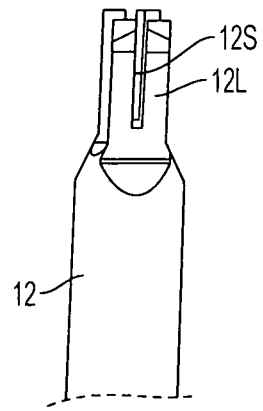 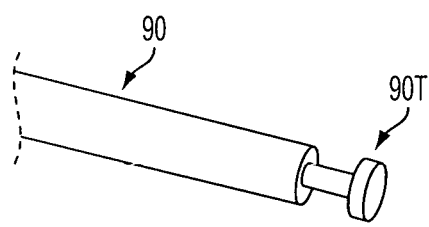 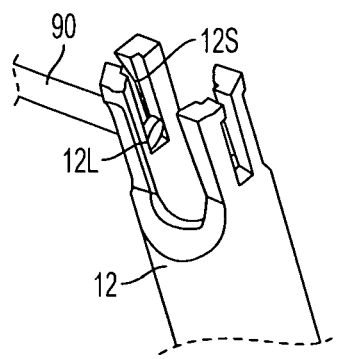
FIG. 50A     FIG. 50B     FIG. 50C
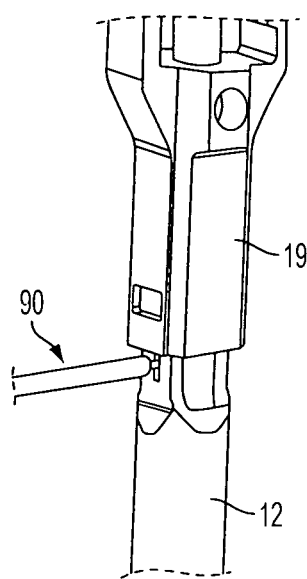 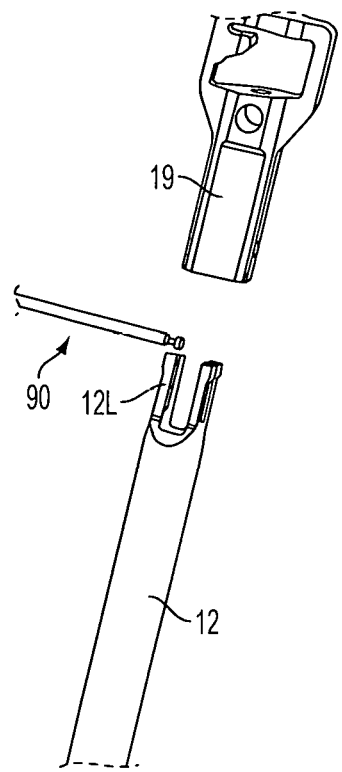
FIG. 50D     FIG. 50E

INDEPENDENT GRIPPER

CROSS-REFERENCE TO RELATED APPLICATION

The present application is a continuation of U.S. patent application Ser. No. 14/643,718, filed Mar. 10, 2015, which is a divisional of U.S. patent application Ser. No. 13/231,572, filed Sep. 13, 2011, the full disclosure of which is incorporated herein by reference.

BACKGROUND OF THE INVENTION

1. Field of the Invention

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall may be damaged or otherwise dysfunctional. Commonly, the valve annulus may be damaged, dilated, or weakened limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity. More recently, minimally invasive catheter based procedures have been developed to deliver implantable clips to the incompetent valve. These clips are used to fasten a portion of the valve leaflets together, thereby reducing the regurgitation. While the clips appear to be promising, delivery and deployment of the clip can be challenging. In some situations, it may be challenging to visualize the clip and valve leaflets using techniques such as fluoroscopy and echocardiography. Therefore, improved attachment mechanisms and attachment evaluation methods would be desirable.

For these reasons, it would be desirable to provide improved methods, devices, and systems for performing the repair of mitral and other cardiac valves. Such methods, devices, and systems should preferably not require open chest access and be capable of being performed either endovascularly, i.e., using devices which are advanced to the heart from a point in the patient's vasculature remote from the heart or by a minimally invasive approach. Further, such devices and systems should provide features which allow easier delivery of fixation devices, as well as repositioning and optional removal of the fixation device prior to fixation to ensure optimal placement. Still more preferably, the methods, devices, and systems would be useful for repair of tissues in the body other than heart valves. At least some of these objectives will be met by the inventions described hereinbelow.

2. Description of the Related Art

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759.

Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorac. Surg. 66:1640-1646, describe open surgical procedures for performing "edge-to-edge" or "bow-tie" mitral valve repair where edges of the opposed valve leaflets are sutured together to lessen regurgitation. Dec and Fuster (1994) N. Engl. J. Med. 331:1564-1575 and Alvarez et al. (1996) J. Thorac. Cardiovasc. Surg. 112:238-247 are review articles discussing the nature of and treatments for dilated cardiomyopathy.

Mitral valve annuloplasty is described in the following publications. Bach and Bolling (1996) Am. J. Cardiol. 78:966-969; Kameda et al. (1996) Ann. Thorac. Surg. 61:1829-1832; Bach and Bolling (1995) Am. Heart J. 129:1165-1170; and Bolling et al. (1995) 109:676-683. Linear segmental annuloplasty for mitral valve repair is described in Ricchi et al. (1997) Ann. Thorac. Surg. 63:1805-1806. Tricuspid valve annuloplasty is described in McCarthy and Cosgrove (1997) Ann. Thorac. Surg. 64:267-268; Tager et al. (1998) Am. J. Cardiol. 81:1013-1016; and Abe et al. (1989) Ann. Thorac. Surg. 48:670-676.

Percutaneous transluminal cardiac repair procedures are described in Park et al. (1978) Circulation 58:600-608; Uchida et al. (1991) Am. Heart J. 121: 1221-1224; and Ali Khan et al. (1991) Cathet. Cardiovasc. Diagn. 23:257-262.

Endovascular cardiac valve replacement is described in U.S. Pat. Nos. 5,840,081; 5,411,552; 5,554,185; 5,332,402; 4,994,077; and 4,056,854. See also U.S. Pat. No. 3,671,979 which describes a catheter for temporary placement of an artificial heart valve.

Other percutaneous and endovascular cardiac repair procedures are described in U.S. Pat. Nos. 4,917,089; 4,484,579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769,812; and 5,718,725.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above. Aspects of the invention provide devices, systems and methods for tissue approximation and repair at treatment sites. The devices, systems and methods of the invention will find use in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The invention is particularly useful in those procedures requiring minimally-invasive or endovascular access to remote tissue locations, where the instruments utilized must negotiate long, narrow, and tortuous pathways to the treatment site. In addition, many of the devices and systems of the invention are adapted to be reversible and removable from the patient at any point without interference with or trauma to internal tissues.

According to certain aspects of the invention, the devices, systems and methods are adapted for fixation of tissue at a treatment site. Exemplary tissue fixation applications include cardiac valve repair, septal defect repair, vascular ligation and clamping, laceration repair and wound closure, but the invention may find use in a wide variety of tissue approximation and repair procedures. In one embodiment, the devices, systems and methods of the invention are adapted for repair of cardiac valves, and particularly the mitral valve, as a therapy for regurgitation. The invention enables two or more valve leaflets to be coapted using an "edge-to-edge" or "bow-tie" technique to reduce regurgitation, yet does not require open heart surgery through the chest and heart wall as in conventional approaches. Using the devices, systems and methods of the invention, the mitral valve can be accessed from a remote surgical or vascular access point and the two valve leaflets may be coapted using endovascular or minimally invasive approaches. In some circumstances the invention may also find application in open surgical approaches as well. According certain aspects of the invention, the mitral valve may be approached either from the atrial side (antegrade approach) or the ventricular side (retrograde approach), and either through blood vessels or through the heart wall.

The devices, systems and methods of the invention are centered on variety of devices which may be used individually or in a variety of combinations to form interventional systems. In preferred embodiments, the interventional system includes a multi-catheter guiding system, a delivery catheter and an interventional device. Each of these components will be discussed herein.

According to one aspect of the invention, a fixation system for engaging tissue comprises an implantable fixation device comprising a pair of fixation elements each having a first end, a free end opposite the first end, and an engagement surface therebetween for engaging the tissue. The first ends are movably coupled together such that the fixation elements are moveable between a closed position, wherein the engagement surfaces face each other, to a first open position wherein the engagement surfaces are positioned away from each other. The fixation system also comprises an actuation mechanism coupled to the fixation elements adapted to move the fixation elements between the closed position and the first open position and a pair of gripping elements comprising a first gripping element and a second gripping element. Each of the gripping elements is moveable with respect to one of the fixation elements and configured to be moved in opposition to one of the engagement surfaces so as to capture tissue therebetween. The fixation system also comprises a first gripper actuator releasably coupled to the implantable fixation device and configured to individually actuate the gripping elements. The free ends of the fixation elements are moveably coupled to move between a closed position where the engagement surfaces face each other and a closed position where the engagement surfaces face away from one another. The fixation elements may each have a concave portion for receiving a corresponding one of the pair of gripping elements when the gripping elements are moved into opposition to one of the engagement surfaces.

The first gripping actuator may be releasably coupled to the implantation fixation device and actuatable between a first configuration and a second configuration that moves the first gripping element toward a first fixation element of the pair of fixation elements. The first gripper actuator may also be actuatable between the second configuration and a third configuration that moves the second gripping element toward a second fixation element of the pair of fixation elements independently of the movement of the first gripping element.

The elongate delivery shaft may comprise a proximal portion and a distal portion, wherein the distal portion is releasably coupled to the proximal portion of the implantable fixation device. The gripper actuator may comprise a proximal end and a distal end, the distal end being releasably coupled to at least one of the proximal end of the implantable fixation device or the distal end of the elongate delivery shaft. The gripper actuator may further comprise a gripper line that extends from the proximal end of the delivery shaft and which is coupled to each of the first gripping element and the second gripping element at portions of the gripper line between the proximal end of the delivery shaft and releasably coupled to at least one of the proximal end of the implantable fixation device or the distal end of the elongate delivery shaft.

According to another aspect, the gripper line may be actuated by tension on the gripper line and configured to apply a different resultant force the each of the first gripping element and the second gripping element to induce the individual activation of the gripping elements at different levels of tension. The gripper actuator may be configured to be released from the implantable fixation device when the elongate delivery shaft is decoupled from the implantable fixation device.

According to another aspect, a fixation system for engaging tissue may comprise an implantable fixation device comprising a pair of fixation elements including a first fixation element and a second fixation element, each having a first end, a free end opposite the first end, and an engagement surface therebetween for engaging the tissue. The first ends may be movably coupled together such that the fixation elements are moveable between a closed position, wherein the engagement surfaces face each other, to a first open position wherein the engagement surfaces are positioned away from each other. An actuation mechanism may be coupled to the fixation elements and adapted to move the fixation elements between the closed position and the first open position. The fixation system may also include a pair of gripping elements comprising a first gripping element and a second gripping element, each of the gripping elements configured to be moveable with respect to one of the fixation elements and configured to be moved in opposition to one of the engagement surfaces so as to capture tissue therebetween. The fixation system may comprise a first gripper actuator releasably coupled to the implantable fixation device and configured to actuate the first gripping element, the first gripper actuator having a first configuration and a second configuration, wherein actuating the first gripper actuator between the first configuration and the second configuration moves the first gripping element with respect to the first fixation element. A second gripper actuator may also be releasably coupled to the implantable fixation device and configured to actuate the second gripping element, the second gripper actuator having first configuration and a second configuration, wherein actuating second gripper actuator between the first configuration and the second configuration moves the first gripping element with respect to the first fixation element. The first gripper actuator and the second gripper actuator may be actuatable between the first configuration and the second configuration independently of each other.

The first gripper actuator may comprise a first gripper line having a proximal end and a distal end, and the second gripper actuator may comprise a second gripper line having a proximal end and a distal end. The distal portions of the first gripper line and the second gripper line may be releasably coupled to the implantable fixation device.

The fixation system may also comprise an elongate delivery shaft having a proximal portion and a distal portion, wherein the distal portion of the elongate delivery shaft is releasably coupled to a proximal portion of the fixation device. The first gripper actuator may comprise a first gripper line having a proximal end and a distal end, and the second gripper actuator may comprise a second gripper line having a proximal end and a distal end, wherein the distal portions of the first gripper line and the second gripper line are releasably coupled to at least one of the proximal end of the implantable fixation device or the distal end of the elongate delivery shaft. The first gripper actuator and the second gripper actuator may be configured to be released from the at least one of the proximal end of the implantable fixation device or the distal end of the elongate delivery shaft when the elongate delivery shaft is decoupled from the implantable fixation device.

The fixation system may also comprise a gripper pusher releasably coupled to the implantable fixation device adjacent the pair of gripping elements, the gripper pusher having an expanded configuration and a collapsed configuration. Also, when in the expanded configuration the gripper pusher may be configured to engage the pair of gripping elements and advances the pair of gripping elements toward the engagement surfaces of the fixation elements. On the other hand, when in the collapsed configuration the gripper pusher has a reduced radial profile relative to the gripper pusher radial profile in the expanded configuration thereby allowing the pair of gripping elements to move away from the engagement surfaces of the fixation elements. The first gripping actuator may be releasably coupled to the implantation fixation device and be actuatable between a first configuration and a second configuration that moves the first gripping element toward a first fixation element of the pair of fixation elements. The first gripper actuator may also be actuatable between the second configuration and a third configuration that moves the second gripping element toward a second fixation element of the pair of fixation elements independently of the movement of the first gripping element.

According to another aspect, a distal portion of the gripper pusher may be releasably attached to the implantable fixation device. The gripper pusher may comprise a pair of elongate flexible arms and a shaft of the implantable fixation device includes apertures for releasably engaging a distal end of each of the pair of elongate flexible arms. Also, a proximal portion of the implantable fixation device may comprise a pair of apertures, wherein the distal portion of the elongate delivery shaft comprises a pair of L-shaped ends resiliently biased to fit into the pair of apertures, and wherein the distal ends of the pair of elongate flexible arms are releasably coupled to the implantable fixation device by being fitted into the apertures and with the pair of L-shaped ends. The fixation system may also comprise an actuation rod configured to extend through the elongate delivery shaft and into the implantable fixation device to actuate the pair of fixation elements, wherein the fixation system is configured such that withdrawal of the actuation rod from the implantable fixation device releases the L-shaped ends and the distal ends of the pair of elongate flexible arms from the implantable fixation device.

According to another aspect, the first gripper actuator and the second gripper actuator each comprise distal ends, wherein placing the distal ends of the first gripper actuator and the second gripper actuator adjacent the distal portion of the elongate deliver shaft and coupling the distal portion of the elongate delivery shaft to the proximal portion of the fixation device locks the distal ends of the first gripper actuator and the second gripper actuator in position. The distal ends of the first gripper actuator and the second gripper actuator may comprise a narrow portion and a wide portion, and the elongate delivery shaft and the fixation device may be shaped to form hollow portions that when coupled together hold the wide portion of the first gripper actuator and the second gripper actuator in position.

According to another aspect, the distal ends of the first gripper actuator and the second gripper actuator may comprise a narrow portion and a wide portion and the elongate delivery shaft may comprise open slots having a width narrower than the wide portion of the first and second gripper actuators. The fixation device may be configured to closes the open slots when coupled to the elongate delivery shaft to hold the first gripper actuator and the second gripper actuator in position.

According to another aspect, the fixation system may comprise a covering assembly coupled to and disposed over the distal portion of the elongate delivery shaft. The covering assembly may comprise an outer slideable section and an inner section having a T-shaped opening such that the first gripper actuator is releasably coupled to the fixation device by sliding a T-shaped distal end of the first gripper actuator into the T-shaped opening of the inner section of the covering assembly and sliding the outer slideable section to cover the T-shaped openings.

According to another aspect, the fixation system may comprise an actuator rod that extends through the delivery shaft and into the implantable fixation device to actuate the pair of fixation elements. The delivery shaft may comprise opening portions and liners disposed inside of the delivery shaft configured to occlude the opening portions. The pair of gripper actuators may be disposed in a corresponding one of the opening portions and fixed by the liners when the actuator rod is extended into the implantable fixation device and released by the liners when the actuator rod is withdraw from the implantable fixation device. The liner may be hingedly attached to the delivery shaft.

The fixation system may further comprise an actuator rod that extends through the delivery shaft and into the implantable fixation device to actuate the pair of fixation elements. The delivery shaft may comprise opening portions and spring members disposed on the exterior of the delivery shaft having bent portions that extend into the opening portions, each spring member having a notched end and the notched ends of the spring members being configured to abut to form an opening sized to releasably engage the first gripper actuator. The actuator rod may have a taper shape configured to press the bent portions when the actuator rod is withdrawn from the implantable fixation device to release the first gripper actuator by causing the notched ends to separate.

According to another aspect, a method for fixing tissue is provided. The method comprises providing an implantable fixation device comprising a pair of fixation elements each having a first end, a free end opposite the first end, and an engagement surface therebetween for engaging the tissue, the first ends being movably coupled together such that the fixation elements are moveable between a closed position wherein the engagement surfaces face each other to a first open position wherein the engagement surfaces are positioned away from each other; an actuation mechanism coupled to the fixation elements adapted to move the fixation elements between the closed position and the first open position; and a pair of gripping elements comprising a first gripping element and a second gripping element, each of the gripping elements moveable with respect to one of the fixation elements and configured to be moved in opposition to one of the engagement surfaces so as to capture tissue therebetween. The method also comprises positioning the fixation elements so that tissue is disposed between the pair of gripping elements and the engagement surfaces of the pair of fixation element; and activating a first gripper actuator to individually actuate the first gripping elements to grasp tissue between the first gripping element and one of the fixation elements.

Other aspects of the nature and advantages of the invention are set forth in the detailed description set forth below, taken in conjunction with the drawings.

BRIEF DESCRIPTION OF THE DRAWINGS

The above and other aspects and features of the present invention will become more apparent by describing in detail exemplary embodiments thereof with reference to the attached drawings in which:

FIGS. 7A-7B and 8A-8B illustrate the movement of fixation elements of an embodiment of the fixation device of the present invention.

FIGS. 22A, 22B, and 23-27 illustrate another embodiment of a fixation device having a covering and independent actuation.

FIGS. 49A-49C, 50A-50E, 51A-51B and 52A-52G illustrate various embodiments of coupling a proximal element line to a proximal element of a fixation device.

DETAILED DESCRIPTION OF THE INVENTION

I. Cardiac Physiology

Figure 1:
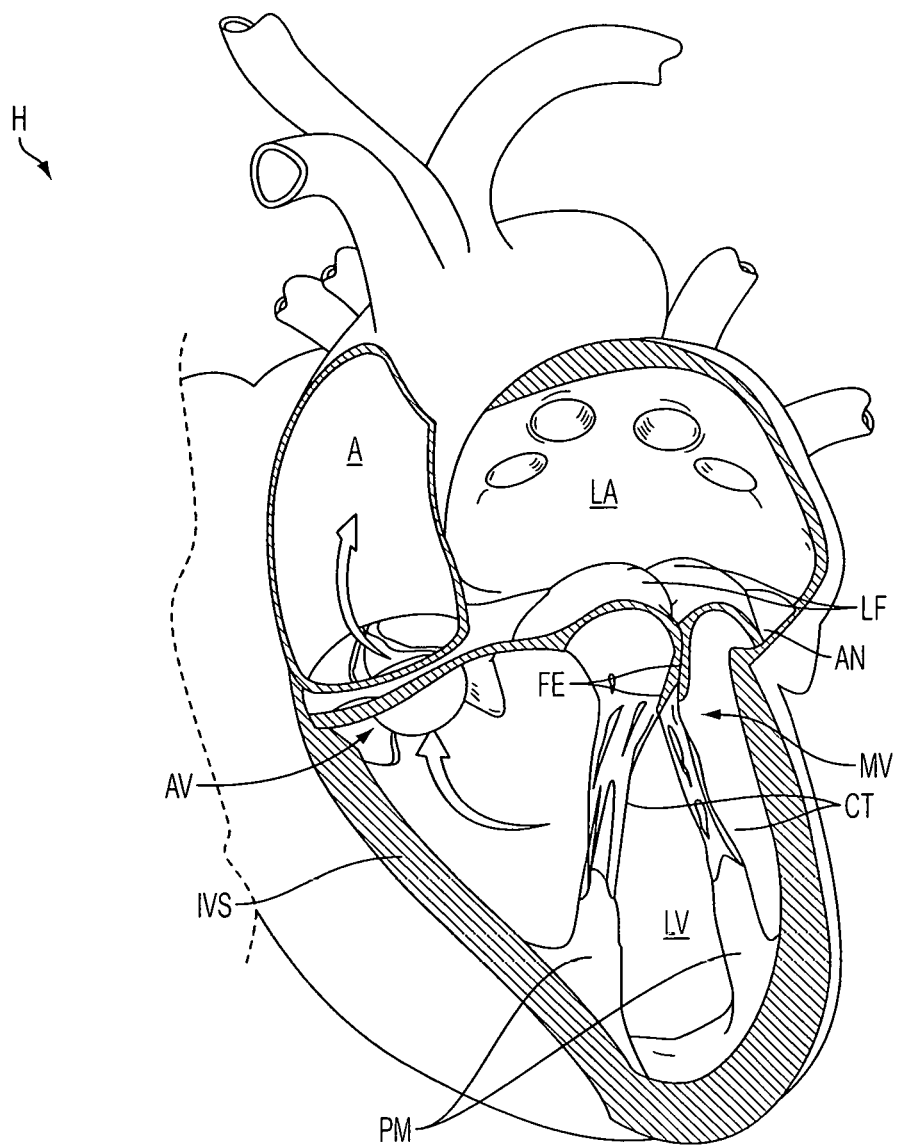
FIG. 1 illustrates the left ventricle and left atrium of the heart during systole.

The left ventricle LV of a normal heart H in systole is illustrated in FIG. 1. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendinae CT (referred to hereinafter as the chordae) which include a plurality of branching tendons secured over the lower surfaces of each of the valve leaflets LF. The chordae CT in turn, are attached to the papillary muscles PM which extend upwardly from the lower portions of the left ventricle and intraventricular septum IVS.

Figure 2A:
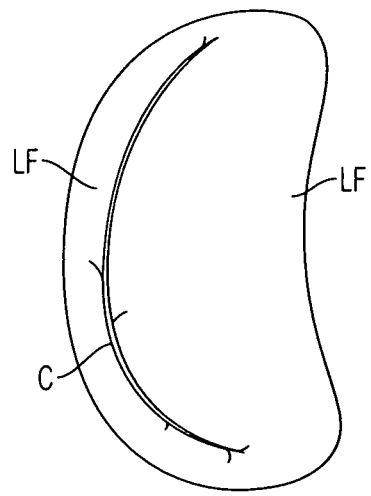
FIG. 2A illustrates free edges of leaflets in normal coaptation.
Figure 2B:
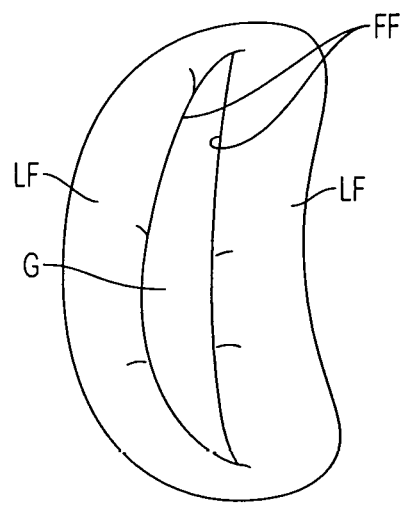
FIG. 2B illustrates the free edges in regurgitative coaptation.

A number of structural defects in the heart can cause mitral valve regurgitation. Regurgitation occurs when the valve leaflets do not close properly allowing leakage from the ventricle into the atrium. As shown in FIG. 2A, the free edges of the anterior and posterior leaflets normally meet along a line of coaptation C. An example of a defect causing regurgitation is shown in FIG. 2B. Here an enlargement of the heart causes the mitral annulus to become enlarged, making it impossible for the free edges FE to meet during systole. This results in a gap G which allows blood to leak through the valve during ventricular systole. Ruptured or elongated chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper closure.

II. General Overview

Aspects of the present invention provides methods and devices for grasping, approximating and fixating tissues such as valve leaflets to treat cardiac valve regurgitation, particularly mitral valve regurgitation. The present invention also provides features that allow repositioning and removal of the device if so desired, particularly in areas where removal may be hindered by anatomical features such as chordae CT. Such removal would allow the surgeon to reapproach the valve in a new manner if so desired.

Grasping will preferably be atraumatic providing a number of benefits. By atraumatic, it is meant that the devices and methods of the invention may be applied to the valve leaflets and then removed without causing any significant clinical impairment of leaflet structure or function. The leaflets and valve continue to function substantially the same as before the invention was applied. Thus, some minor penetration or denting of the leaflets may occur using the invention while still meeting the definition of "atraumatic". This enables the devices of the invention to be applied to a diseased valve and, if desired, removed or repositioned without having negatively affected valve function. In addition, it will be understood that in some cases it may be necessary or desirable to pierce or otherwise permanently affect the leaflets during either grasping, fixing or both. In some of these cases, grasping and fixation may be accomplished by a single device. Although a number of embodiments are provided to achieve these results, a general overview of the basic features will be presented herein. Such features are not intended to limit the scope of the invention and are presented with the aim of providing a basis for descriptions of individual embodiments presented later in the application.

Figure 3A:
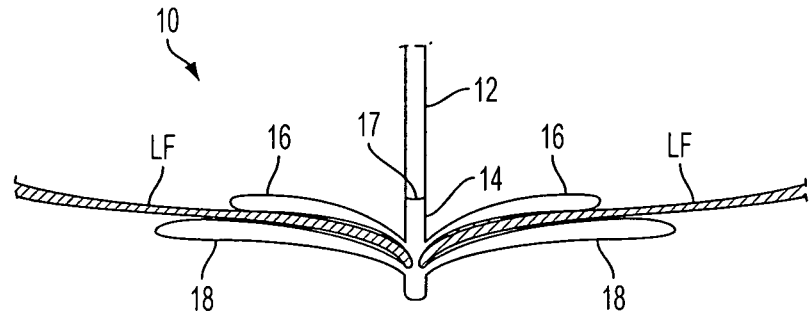
FIGS. 3A-3C illustrate grasping of the leaflets with a fixation device, inversion of the distal elements of the fixation device and removal of the fixation device, respectively.

The devices and methods of the invention rely upon the use of an interventional tool that is positioned near a desired treatment site and used to grasp the target tissue. In endovascular applications, the interventional tool is typically an interventional catheter. In surgical applications, the interventional tool is typically an interventional instrument. In preferred embodiments, fixation of the grasped tissue is accomplished by maintaining grasping with a portion of the interventional tool which is left behind as an implant. While the invention may have a variety of applications for tissue approximation and fixation throughout the body, it is particularly well adapted for the repair of valves, especially cardiac valves such as the mitral valve. Referring to FIG. 3A, an interventional tool 10, having a delivery device, such as a shaft 12, and a fixation device 14, is illustrated having approached the mitral valve MV from the atrial side and grasped the leaflets LF. The mitral valve may be accessed either surgically or by using endovascular techniques, and either by a retrograde approach through the ventricle or by an antegrade approach through the atrium, as described above. For illustration purposes, an antegrade approach is described.

The fixation device 14 is releasably attached to the shaft 12 of the interventional tool 10 at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the mitral valve, proximal shall refer to the atrial or upstream side of the valve leaflets and distal shall refer to the ventricular or downstream side of the valve leaflets.

The fixation device 14 typically comprises proximal elements 16 (or gripping elements) and distal elements 18 (or fixation elements) which protrude radially outward and are positionable on opposite sides of the leaflets LF as shown so as to capture or retain the leaflets therebetween. The proximal elements 16 are preferably comprised of cobalt chromium, nitinol or stainless steel, and the distal elements 18 are preferably comprised of cobalt chromium or stainless steel, however any suitable materials may be used. The fixation device 14 is coupleable to the shaft 12 by a coupling mechanism 17. The coupling mechanism 17 allows the fixation device 14 to detach and be left behind as an implant to hold the leaflets together in the coapted position.

Figure 3B:
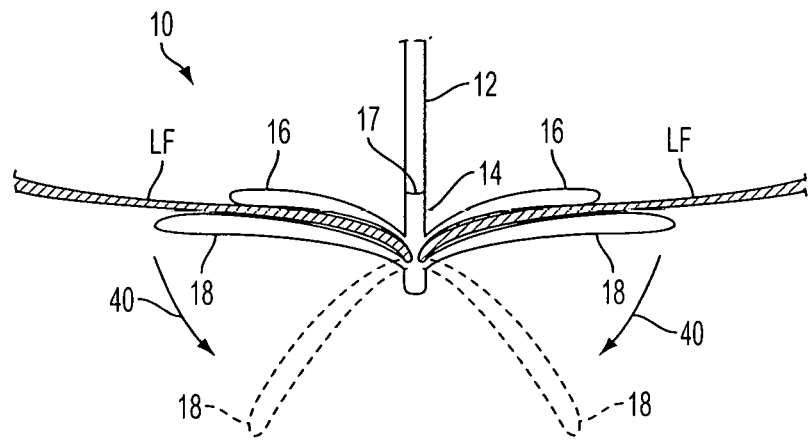
Figure 3C:
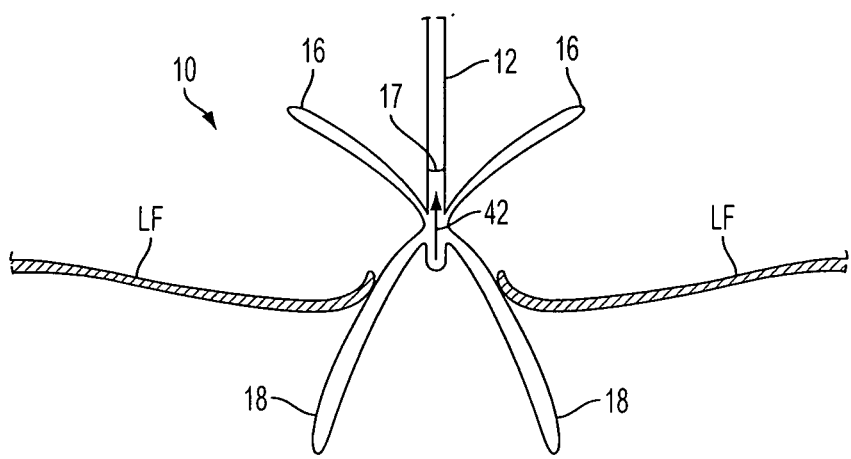

In some situations, it may be desired to reposition or remove the fixation device 14 after the proximal elements 16, distal elements 18, or both have been deployed to capture the leaflets LF. Such repositioning or removal may be desired for a variety of reasons, such as to reapproach the valve in an attempt to achieve better valve function, more optimal positioning of the device 14 on the leaflets, better purchase on the leaflets, to detangle the device 14 from surrounding tissue such as chordae, to exchange the device 14 with one having a different design, or to abort the fixation procedure, to name a few. To facilitate repositioning or removal of the fixation device 14 the distal elements 18 are releasable and optionally invertible to a configuration suitable for withdrawal of the device 14 from the valve without tangling or interfering with or damaging the chordae, leaflets or other tissue. FIG. 3B illustrates inversion wherein the distal elements 18 are moveable in the direction of arrows 40 to an inverted position. Likewise, the proximal elements 16 may be raised, if desired. In the inverted position, the device 14 may be repositioned to a desired orientation wherein the distal elements may then be reverted to a grasping position against the leaflets as in FIG. 3A. Alternatively, the fixation device 14 may be withdrawn (indicated by arrow 42) from the leaflets as shown in FIG. 3C. Such inversion reduces trauma to the leaflets and minimizes any entanglement of the device with surrounding tissues. Once the device 14 has been withdrawn through the valve leaflets, the proximal and distal elements may be moved to a closed position or configuration suitable for removal from the body or for reinsertion through the mitral valve.

Figure 4:
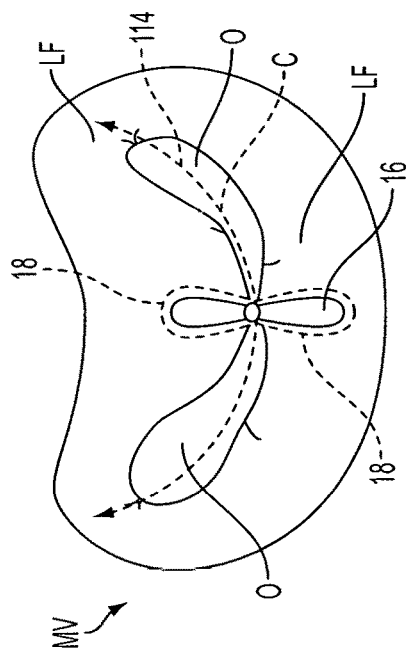
FIG. 4 illustrates the position of the fixation device in a desired orientation relative to the leaflets.

FIG. 4 illustrates the position of the fixation device 14 in a desired orientation in relation to the leaflets LF. This is a short-axis view of the mitral valve MV from the atrial side, therefore, the proximal elements 16 are shown in solid line and the distal elements 18 are shown in dashed line. The proximal and distal elements 16, 18 are positioned to be substantially perpendicular to the line of coaptation C. The device 14 may be moved roughly along the line of coaptation to the location of regurgitation. The leaflets LF are held in place so that during diastole, as shown in FIG. 4, the leaflets LF remain in position between the elements 16, 18 surrounded by openings O which result from the diastolic pressure gradient. Advantageously, leaflets LF are coapted such that their proximal or upstream surfaces are facing each other in a vertical orientation, parallel to the direction of blood flow through mitral valve MV. The upstream surfaces may be brought together so as to be in contact with one another or may be held slightly apart, but will preferably be maintained in the vertical orientation in which the upstream surfaces face each other at the point of coaptation. This simulates the double orifice geometry of a standard surgical bow-tie repair. Color Doppler echo will show if the regurgitation of the valve has been reduced. If the resulting mitral flow pattern is satisfactory, the leaflets may be fixed together in this orientation. If the resulting color Doppler image shows insufficient improvement in mitral regurgitation, the interventional tool 10 may be repositioned. This may be repeated until an optimal result is produced wherein the leaflets LF are held in place.

Figure 5B:
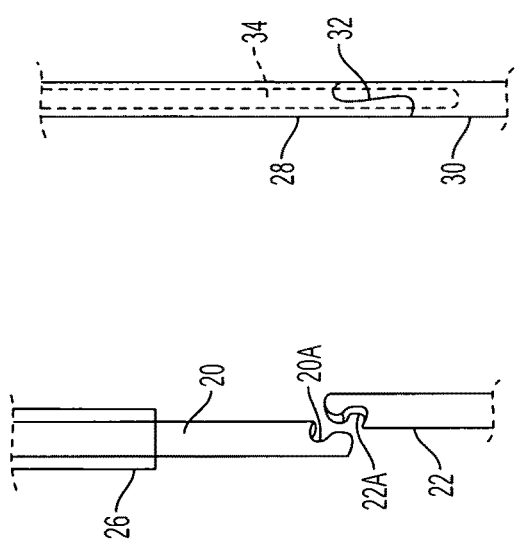
Figure 5A:
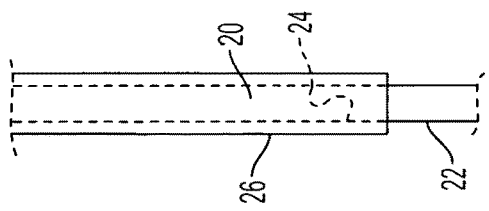

Once the leaflets are coapted in the desired arrangement, the fixation device 14 is then detached from the shaft 12 and left behind as an implant to hold the leaflets together in the coapted position. As mentioned previously, the fixation device 14 is coupled to the shaft 12 by a coupling mechanism 17. FIGS. 5A-5B, 6A-6B illustrate exemplary embodiments of such coupling mechanisms. FIG. 5A shows an upper shaft 20 and a detachable lower shaft 22 which are interlocked at a joining line or mating surface 24. The mating surface 24 may have any shape or curvature which will allow or facilitate interlocking and later detachment. A snuggly fitting outer sheath 26 is positioned over the shafts 20, 22 to cover the mating surface 24 as shown. FIG. 5B illustrates detachment of the lower shaft 22 from the upper shaft 20. This is achieved by retracting the outer sheath 26, so that the mating surface 24 is exposed, which allows the shafts 20, 22 to separate.

Figure 6B:
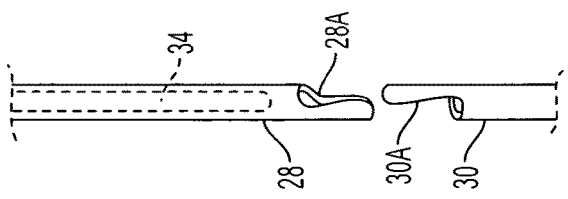
FIGS. 5A-5B and 6A-6B illustrate exemplary embodiments of coupling mechanisms of the instant application.
Figure 6A:
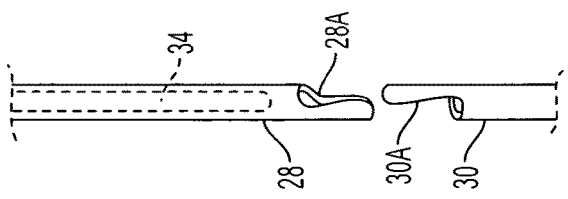

Similarly, FIG. 6A illustrates a tubular upper shaft 28 and a detachable tubular lower shaft 30 which are interlocked at a mating surface 32. Again, the mating surface 32 may have any shape or curvature which will allow or facilitate interlocking and later detachment. The tubular upper shaft 28 and tubular lower shaft 30 form an outer member having an axial channel. A snuggly fitting rod 34 or inner member is inserted through the tubular shafts 28, 30 to bridge the mating surface 32 as shown. FIG. 6B illustrates detachment of the lower shaft 30 from the upper shaft 28. This is achieved by retracting the rod 34 to a position above the mating surface 32 which in turn allows the shafts 28, 30 to separate. Other examples of coupling mechanisms are described and illustrated in copending U.S. patent application Ser. No. 09/894,493), incorporated herein by reference for all purposes.

Similarly, FIG. 6A illustrates a tubular upper shaft 28 and a detachable tubular lower shaft 30 which are interlocked at a mating surface 32. Again, the mating surface 32 may have any shape or curvature which will allow or facilitate interlocking and later detachment. The tubular upper shaft 28 and tubular lower shaft 30 form an outer member having an axial channel. A snuggly fitting rod 34 or inner member is inserted through the tubular shafts 28, 30 to bridge the mating surface 32 as shown. FIG. 6B illustrates detachment of the lower shaft 30 from the upper shaft 28. This is achieved by retracting the rod 34 to a position above the mating surface 32 which in turn allows the shafts 28, 30 to separate. Other examples of coupling mechanisms are described and illustrated in copending U.S. patent application Ser. No. 09/894,493, incorporated herein by reference for all purposes.

III. Fixation Device

A. Introduction and Placement

The fixation device 14 is delivered to the valve or the desired tissues with the use of a delivery device. The delivery device may be rigid or flexible depending on the application. For endovascular applications, the delivery device comprises a flexible delivery catheter which will be described in later sections. Typically, however, such a catheter comprises a shaft, having a proximal end and a distal end, and a fixation device releasably attached to its distal end. The shaft is usually elongate and flexible, suitable for intravascular introduction. Alternatively, the delivery device may comprise a shorter and less flexible interventional instrument which may be used for trans-thoracic surgical introduction through the wall of the heart, although some flexibility and a minimal profile will generally be desirable. A fixation device is releasably coupleable with the delivery device as illustrated in FIG. 3A. The fixation device may have a variety of forms, a few embodiments of which will be described herein.

FIGS. 7A-8B illustrate an embodiment of a fixation device 14 in various positions or configurations. FIG. 7A illustrates the fixation device 14 in a closed configuration for delivery through the patient's vasculature and, in this example, through the mitral valve. The fixation device 14 includes a coupling member 19 which allows detachment of the fixation device 14 for implantation. In this example, the coupling member 19 is shown to include the lower shaft 22 and mating surface 24 of FIGS. 5A-5B, and therefore the coupling member 19 would function similarly as described above. The fixation device 14 also includes a pair of opposed distal elements 18, each distal element 18 having an engagement surface 50 facing inwardly toward the opposed distal element 18 in the closed configuration. Distal elements 18 preferably comprise elongate arms 53, each arm having a proximal end 52 rotatably connected to the coupling member 19 and a free end 54. Suitable connections for arms 53 to coupling member 19 include pins, living hinges, or other known rotational connection mechanisms. In the closed configuration of FIG. 7A, free ends 54 point in a first direction such that the arms 53 and engagement surfaces 50 are nearly parallel to each other and to an axis 21, and preferably are angled slightly inwardly toward each other. In a preferred embodiment, when tissue is not present between arms 53, the arms 53 may be closed until free ends 54 either touch each other or engage shaft 12 when fixation device 14 is attached thereto, thereby minimizing the profile of the fixation device 14 for passage through a delivery device.

FIGS. 7B-8A illustrate the fixation device 14 in an open position wherein the engagement surfaces 50 are disposed at a separation angle 56 apart, wherein the separation angle 56 is typically up to approximately 180 degrees, preferably up to 90-180 degrees, and arms 53 are disposed generally symmetrically relative to axis 21. The arms 53 may be moveable to the open position by a variety of actuation mechanisms. For example, a plunger or actuator rod may be advanced through the coupling member 19, as indicated by arrow 62, so as to engage a spring or spring loaded actuation mechanism 58 which is attached to the distal elements 18. By exerting a force against the actuation mechanism 58, the distal elements 18 are rotated relative to coupling member 19. The distal elements 18 may be held in this open position by the actuator rod against the resistance provided by the spring of the actuation mechanism 58 which biases the distal elements 18 toward the closed position of FIG. 7A when the distal elements 18 are less than 180 degrees apart. The spring loading of the actuation mechanism 58 resists outward movement of the actuation mechanism 58 and urges the device 14 towards the closed position.

In this embodiment, proximal elements 16 comprise resilient loop-shaped wire forms biased outwardly and attached to the coupling member 19 so as to be biased to an open position shown in FIG. 8A but moveable rotationally inwardly when arms 53 are closed. The wire forms may be flexible enough to be rigidly attached to coupling member 19 and resiliently deflectable inwardly, or they may be attached by a rotational coupling such as a pin or living hinge. In use, leaflets LF are positioned between the proximal elements 16 and distal elements 18. Once, the leaflets LF are positioned between the proximal and distal elements 16, 18, the distal elements 18 may be closed, compressing the leaflets between engagement surfaces 50 and proximal elements 18. Depending upon the thickness of the leaflets, the arrangements of the leaflets, the position of the fixation device on the leaflets and other factors, the arms 53 may be maintained in the open position of FIG. 7B, moved to the fully closed position of FIG. 7A, or placed in any of various positions in between so as to coapt the leaflets LF and hold them in the desired position with the desired degree of force. In any case, the fixation device 14 will remain in place as an implant following detachment from the delivery catheter.

In some situations, as previously mentioned, it may be desirable to reopen the fixation device 14 following initial placement. To reopen the device 14, the actuator rod may be readvanced or reinserted through the coupling member 19 and readvanced to press against the actuation mechanism 58, as previously indicated by arrow 62 in FIG. 7B. Again, such advancement applies a force against the actuation mechanism 58 in the manner described above thus moving arms 53 outwardly to release force against leaflets and move engagement surfaces 50 away from proximal elements 16. The leaflets are then free to move relative to fixation device 14. The fixation device 14 may then be repositioned as desired and the actuator rod retracted to reclose the distal elements 18 to coapt the leaflets.

Under some circumstances, it may be further desirable to withdraw the fixation device 14 back through the valve or completely from the patient following initial insertion through the valve. Should this be attempted with the clip in the closed or open positions illustrated in FIGS. 7A-8A, there may be a risk that arms 53 could interfere or become entangled with the chordae, leaflets or other tissues. To avoid this, the fixation element 14 is preferably adapted for inversion of arms 53 so that free ends 54 point in a second direction, opposite to the first direction in which the free ends 54 pointed in the closed position, each arm 53 forming an obtuse angle relative to axis 21 as illustrated in FIG. 8B. The arms 53 may be rotated so that the engagement surfaces 50 are disposed at a separation angle 56 of up to 360 degrees, and preferably at least up to 270 degrees. This may be accomplished by exerting a force against actuation mechanism 58 with a push rod or plunger extending through coupling member 19 as described above. In this embodiment, once the distal elements 18 have rotated beyond 180 degrees apart, the spring loading of the actuation mechanism 58 biases the distal elements 18 toward the inverted position. The spring loading of the actuation mechanism 58 resists outward movement of the actuation mechanism 58 and urges the device 14 towards the inverted position.

With arms 53 in the inverted position, engagement surfaces 50 provide an atraumatic surface deflect tissues as the fixation device is withdrawn. This allows the device to be retracted back through the valve annulus without risk of injury to valvular and other tissues. In some cases, once the fixation device 14 has been pulled back through the valve, it will be desirable to return the device to the closed position for withdrawal of the device from the body (either through the vasculature or through a surgical opening).

The embodiment illustrated in FIGS. 7A-8B is assembled from separate components composed of biocompatible materials. The components may be formed from the same or different materials, including but not limited to stainless steel or other metals, Elgiloy®, nitinol, titanium, tantalum, metal alloys or polymers. Additionally, some or all of these components may be made of bioabsorbable materials that will be absorbed by surrounding tissues or will dissolve into the bloodstream following implantation. It has been found that in mitral valve repair applications the fixation devices of the invention are completely surrounded by tissue within a few months of implantation, after which the devices could dissolve or be absorbed without negative impact to the repair.

Figure 9:
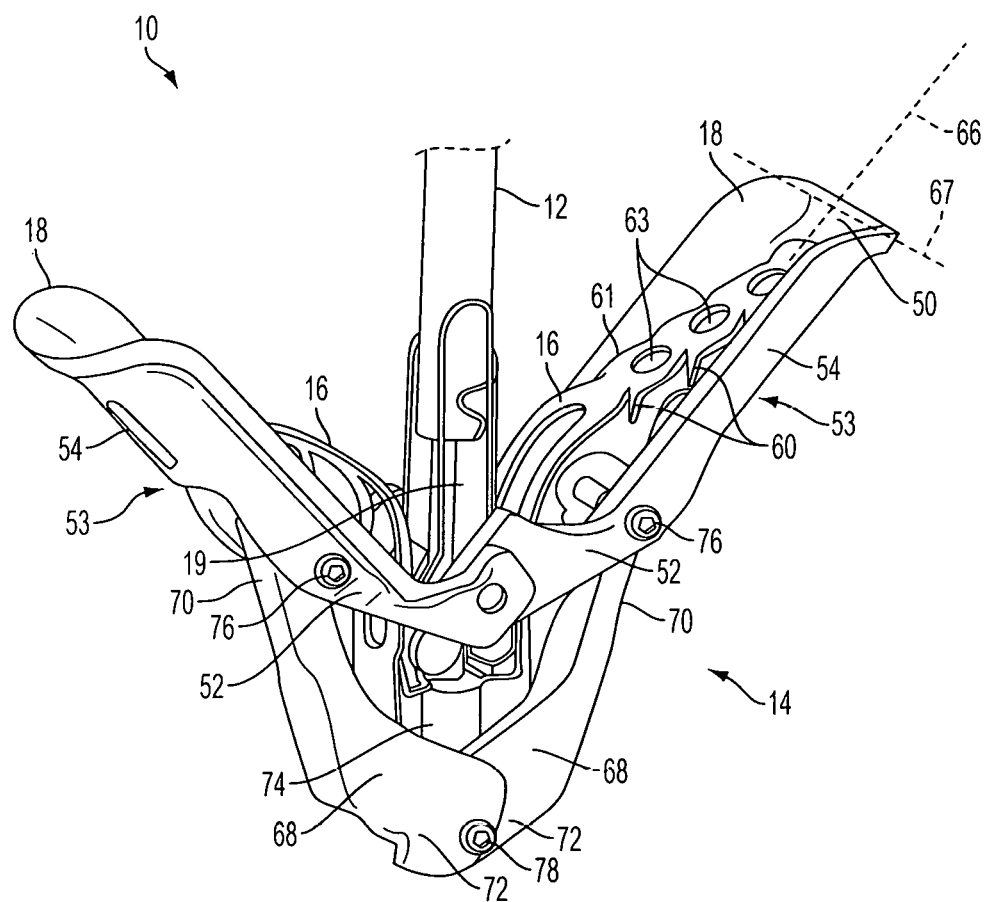
FIG. 9 illustrates another embodiment of the fixation device.

FIG. 9 illustrates another embodiment of a fixation device 14. Here, the fixation device 14 is shown coupled to a shaft 12 to form an interventional tool 10. The fixation device 14 includes a coupling member 19 and a pair of opposed distal elements 18. The distal elements 18 comprise elongate arms 53, each arm having a proximal end 52 rotatably connected to the coupling member 19 and a free end 54. The free ends 54 have a rounded shape to minimize interference with and trauma to surrounding tissue structures. Preferably, each free end 54 defines a curvature about two axes, one being an axis 66 perpendicular to longitudinal axis of arms 53. Thus, the engagement surfaces 50 have a cupped or concave shape to surface area in contact with tissue and to assist in grasping and holding the valve leaflets. This further allows arms 53 to nest around the shaft 12 in the closed position to minimize the profile of the device. Preferably, arms 53 are at least partially cupped or curved inwardly about their longitudinal axes 66. Also, preferably, each free end 54 defines a curvature about an axis 67 perpendicular to axis 66 or the longitudinal axis of arms 53. This curvature is a reverse curvature along the most distal portion of the free end 54. Likewise, the longitudinal edges of the free ends 54 may flare outwardly. Both the reverse curvature and flaring minimize trauma to the tissue engaged therewith.

In an embodiment suitable for mitral valve repair, the transverse width across engagement surfaces 50 (which determines the width of tissue engaged) is at least about 2 mm, usually 3-10 mm, and preferably about 4-6 mm. In some situations, a wider engagement is desired wherein the engagement surfaces 50 are larger, for example about 2 cm, or multiple fixation devices are used adjacent to each other. Arms 53 and engagement surfaces 50 are configured to engage a length of tissue of about 4-10 mm, and preferably about 6-8 mm along the longitudinal axis of arms 53. Arms 53 further include a plurality of openings to enhance grip and to promote tissue ingrowth following implantation.

The valve leaflets are grasped between the distal elements 18 and proximal elements 16. In some embodiments, the proximal elements 16 are flexible, resilient, and cantilevered from coupling member 19. The proximal elements are preferably resiliently biased toward the distal elements. Each proximal element 16 is shaped and positioned to be at least partially recessed within the concavity of the distal element 18 when no tissue is present. When the fixation device 14 is in the open position, the proximal elements 16 are shaped such that each proximal element 16 is separated from the engagement surface 50 near the proximal end 52 of arm 53 and slopes toward the engagement surface 50 near the free end 54 with the free end of the proximal element contacting engagement surface 50, as illustrated in FIG. 9. This shape of the proximal elements 16 accommodates valve leaflets or other tissues of varying thicknesses.

Proximal elements 16 include a plurality of openings 63 and scalloped side edges 61 to increase grip on tissue. The proximal elements 16 optionally include frictional accessories, frictional features or grip-enhancing elements to assist in grasping and/or holding the leaflets. In preferred embodiments, the frictional accessories comprise barbs 60 having tapering pointed tips extending toward engagement surfaces 50. It may be appreciated that any suitable frictional accessories may be used, such as prongs, windings, bands, barbs, grooves, channels, bumps, surface roughening, sintering, high-friction pads, coverings, coatings or a combination of these. Optionally, magnets may be present in the proximal and/or distal elements. It may be appreciated that the mating surfaces will be made from or will include material of opposite magnetic charge to cause attraction by magnetic force. For example, the proximal elements and distal elements may each include magnetic material of opposite charge so that tissue is held under constant compression between the proximal and distal elements to facilitate faster healing and ingrowth of tissue. Also, the magnetic force may be used to draw the proximal elements 16 toward the distal elements 18, in addition to or alternatively to biasing of the proximal elements toward the distal elements. This may assist in deployment of the proximal elements 16. In another example, the distal elements 18 each include magnetic material of opposite charge so that tissue positioned between the distal elements 18 is held therebetween by magnetic force.

The proximal elements 16 may be covered with a fabric or other flexible material as described below to enhance grip and tissue ingrowth following implantation. Preferably, when fabrics or coverings are used in combination with barbs or other frictional features, such features will protrude through such fabric or other covering so as to contact any tissue engaged by proximal elements 16.

In an exemplary embodiment, proximal elements 16 are formed from metallic sheet of a spring-like material using a stamping operation which creates openings 63, scalloped edges 61 and barbs 60. Alternatively, proximal elements 16 could be comprised of a spring-like material or molded from a biocompatible polymer. It should be noted that while some types of frictional accessories that can be used in the present invention may permanently alter or cause some trauma to the tissue engaged thereby, in a preferred embodiment, the frictional accessories will be atraumatic and will not injure or otherwise affect the tissue in a clinically significant way. For example, in the case of barbs 60, it has been demonstrated that following engagement of mitral valve leaflets by fixation device 14, should the device later be removed during the procedure barbs 60 leave no significant permanent scarring or other impairment of the leaflet tissue and are thus considered atraumatic.

The fixation device 14 also includes an actuation mechanism 58. In this embodiment, the actuation mechanism 58 comprises two link members or legs 68, each leg 68 having a first end 70 which is rotatably joined with one of the distal elements 18 at a riveted joint 76 and a second end 72 which is rotatably joined with a stud 74. The legs 68 are preferably comprised of a rigid or semi-rigid metal or polymer such as Elgiloy®, cobalt chromium or stainless steel, however any suitable material may be used. While in the embodiment illustrated both legs 68 are pinned to stud 74 by a single rivet 78, it may be appreciated, however, that each leg 68 may be individually attached to the stud 74 by a separate rivet or pin. The stud 74 is joinable with an actuator rod 64 (not shown) which extends through the shaft 12 and is axially extendable and retractable to move the stud 74 and therefore the legs 68 which rotate the distal elements 18 between closed, open and inverted positions. Likewise, immobilization of the stud 74 holds the legs 68 in place and therefore holds the distal elements 18 in a desired position. The stud 74 may also be locked in place by a locking feature which will be further described in later sections.

In any of the embodiments of fixation device 14 disclosed herein, it may be desirable to provide some mobility or flexibility in distal elements 18 and/or proximal elements 16 in the closed position to enable these elements to move or flex with the opening or closing of the valve leaflets. This provides shock absorption and thereby reduces force on the leaflets and minimizes the possibility for tearing or other trauma to the leaflets. Such mobility or flexibility may be provided by using a flexible, resilient metal or polymer of appropriate thickness to construct the distal elements 18. Also, the locking mechanism of the fixation device (described below) may be constructed of flexible materials to allow some slight movement of the proximal and distal elements even when locked. Further, the distal elements 18 can be connected to the coupling mechanism 19 or to actuation mechanism 58 by a mechanism that biases the distal element into the closed position (inwardly) but permits the arms to open slightly in response to forces exerted by the leaflets. For example, rather than being pinned at a single point, these components may be pinned through a slot that allowed a small amount of translation of the pin in response to forces against the arms. A spring is used to bias the pinned component toward one end of the slot.

Figure 10A:
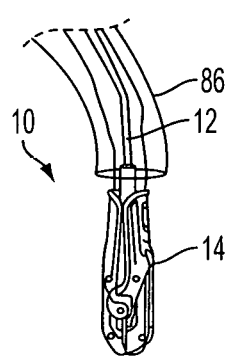
FIGS. 10A-10B, 11A-11B, 12A-12B, 13A-13B and 14-16 illustrate the fixation device of FIG. 7 in various possible positions during introduction and placement of the device within the body to perform a therapeutic procedure.
Figure 10B:
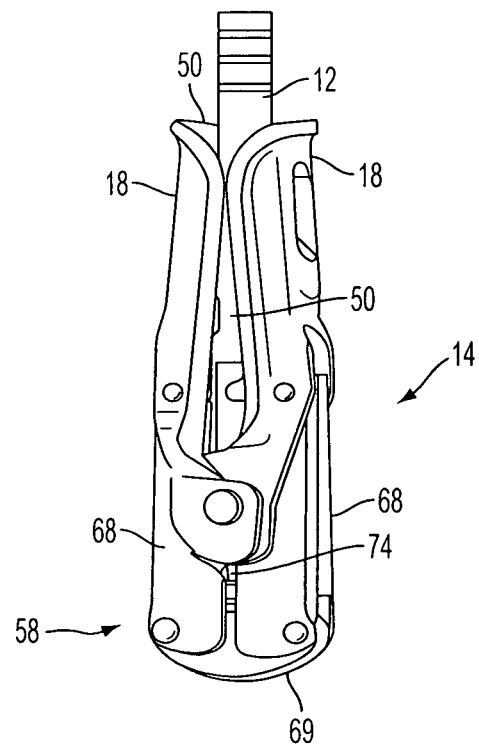

FIGS. 10A-10B, 11A-11B, 12A-12B, 13A-13B, and FIGS. 14-16 illustrate embodiments of the fixation device 14 of FIG. 9 in various possible positions during introduction and placement of the device 14 within the body to perform a therapeutic procedure. FIG. 10A illustrates an embodiment of an interventional tool 10 delivered through a catheter 86. It may be appreciated that the interventional tool 10 may take the form of a catheter, and likewise, the catheter 86 may take the form of a guide catheter or sheath. However, in this example the terms interventional tool 10 and catheter 86 will be used. The interventional tool 10 comprises a fixation device 14 coupled to a shaft 12 and the fixation device 14 is shown in the closed position. FIG. 10B illustrates a similar embodiment of the fixation device of FIG. 10A in a larger view. In the closed position, the opposed pair of distal elements 18 are positioned so that the engagement surfaces 50 face each other. Each distal element 18 comprises an elongate arm 53 having a cupped or concave shape so that together the arms 53 surround the shaft 12 and optionally contact each other on opposite sides of the shaft. This provides a low profile for the fixation device 14 which is readily passable through the catheter 86 and through any anatomical structures, such as the mitral valve. In addition, FIG. 10B further includes an actuation mechanism 58. In this embodiment, the actuation mechanism 58 comprises two legs 68 which are each movably coupled to a base 69. The base 69 is joined with an actuator rod 64 which extends through the shaft 12 and is used to manipulate the fixation device 14. In some embodiments, the actuator rod 64 attaches directly to the actuation mechanism 58, particularly the base 69. However, the actuator rod 64 may alternatively attach to a stud 74 which in turn is attached to the base 69.

In some embodiments, the stud 74 is threaded so that the actuator rod 64 attaches to the stud 74 by a screw-type action. However, the rod 64 and stud 74 may be joined by any mechanism which is releasable to allow the fixation device 14 to be detached from shaft 12.

Figure 11A:
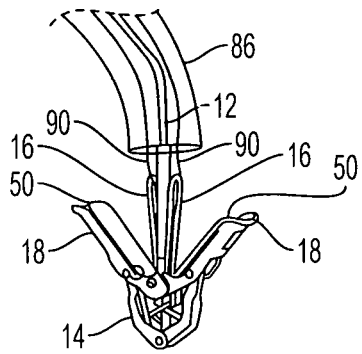
Figure 11B:
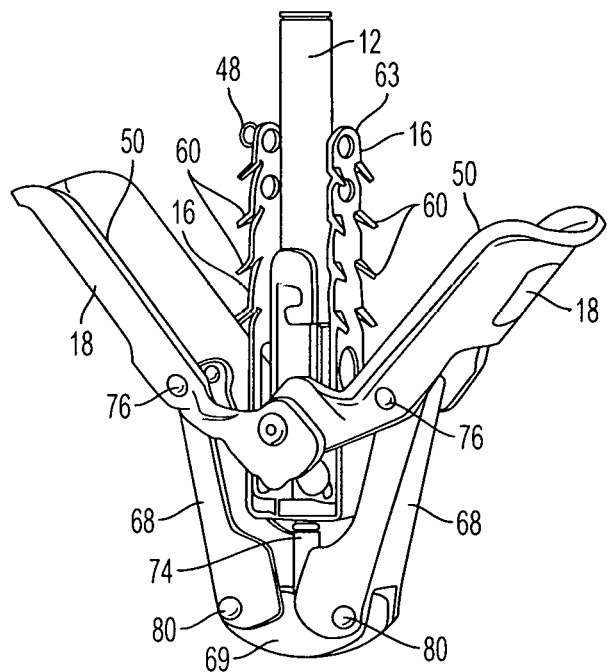

FIGS. 11A-11B illustrate the fixation device 14 in the open position. In the open position, the distal elements 18 are rotated so that the engagement surfaces 50 face a first direction. Distal advancement of the stud 74 relative to coupling member 19 by action of the actuator rod 64 applies force to the distal elements 18 which begin to rotate around joints 76 due to freedom of movement in this direction. Such rotation and movement of the distal elements 18 radially outward causes rotation of the legs 68 about joints 80 so that the legs 68 are directly slightly outwards. The stud 74 may be advanced to any desired distance correlating to a desired separation of the distal elements 18. In the open position, engagement surfaces 50 are disposed at an acute angle relative to shaft 12, and are preferably at an angle of between 90 and 180 degrees relative to each other. In one embodiment, in the open position the free ends 54 of arms 53 have a span therebetween of about 10-20 mm, usually about 12-18 mm, and preferably about 14-16 mm.

Proximal elements 16 are typically biased outwardly toward arms 53. The proximal elements 16 may be moved inwardly toward the shaft 12 and held against the shaft 12 with the aid of proximal element lines 90 which can be in the form of sutures, wires, nitinol wire, rods, cables, polymeric lines, or other suitable structures. The proximal element lines 90 may be connected with the proximal elements 16 by threading the lines 90 in a variety of ways. When the proximal elements 16 have a loop shape, as shown in FIG. 11A, the line 90 may pass through the loop and double back. When the proximal elements 16 have an elongate solid shape, as shown in FIG. 11B, the line 90 may pass through one or more of the openings 63 in the element 16. Further, a line loop 48 may be present on a proximal element 16, also illustrated in FIG. 11B, through which a proximal element line 90 may pass and double back. Such a line loop 48 may be useful to reduce friction on proximal element line 90 or when the proximal elements 16 are solid or devoid of other loops or openings through which the proximal element lines 90 may attach. A proximal element line 90 may attach to the proximal element 16 by detachable means which would allow a single line 90 to be attached to a proximal element 16 without doubling back and would allow the single line 90 to be detached directly from the proximal element 16 when desired. Examples of such detachable means include hooks, snares, clips or breakable couplings, to name a few. By applying sufficient tension to the proximal element line 90, the detachable means may be detached from the proximal element 16 such as by breakage of the coupling. Other mechanisms for detachment may also be used. Similarly, a lock line 92 may be attached and detached from a locking mechanism by similar detachable means.

In the open position, the fixation device 14 can engage the tissue which is to be approximated or treated. The embodiment illustrated in FIGS. 9-11 is adapted for repair of the mitral valve using an antegrade approach from the left atrium. The interventional tool 10 is advanced through the mitral valve from the left atrium to the left ventricle. The distal elements 18 are oriented to be perpendicular to the line of coaptation and then positioned so that the engagement surfaces 50 contact the ventricular surface of the valve leaflets, thereby grasping the leaflets. The proximal elements 16 remain on the atrial side of the valve leaflets so that the leaflets lie between the proximal and distal elements. In this embodiment, the proximal elements 16 have frictional accessories, such as barbs 60 which are directed toward the distal elements 18. However, neither the proximal elements 16 nor the barbs 60 contact the leaflets at this time.

The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 12A:
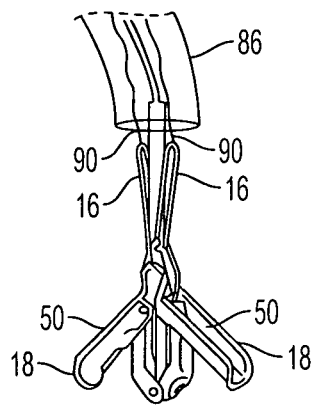
Figure 12B:
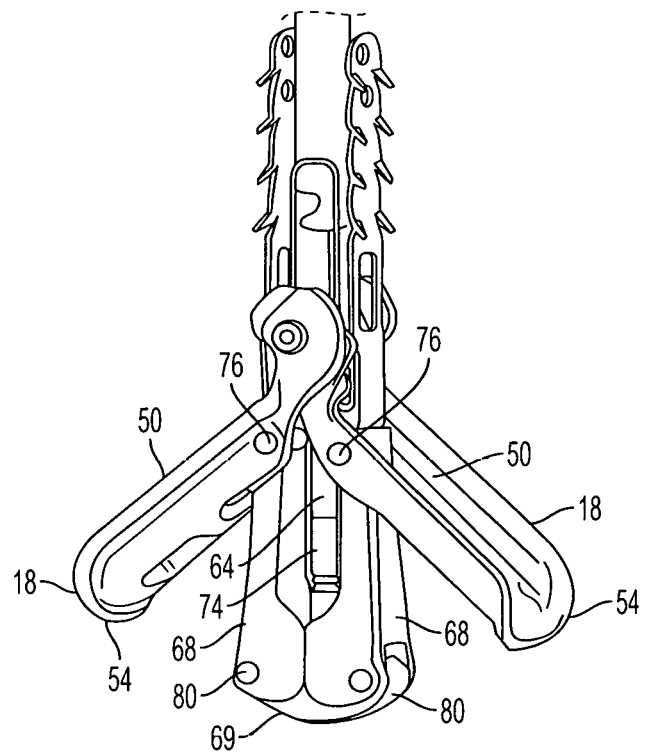

It may also be desired to invert the fixation device 14 to aid in repositioning or removal of the fixation device 14. FIGS. 12A-12B illustrate the fixation device 14 in the inverted position. By further advancement of stud 74 relative to coupling member 19, the distal elements 18 are further rotated so that the engagement surfaces 50 face outwardly and free ends 54 point distally, with each arm 53 forming an obtuse angle relative to shaft 12. The angle between arms 53 is preferably in the range of about 270 to 360 degrees. Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm. In this illustration, the proximal elements 16 remain positioned against the shaft 12 by exerting tension on the proximal element lines 90. Thus, a relatively large space may be created between the elements 16, 18 for repositioning. In addition, the inverted position allows withdrawal of the fixation device 14 through the valve while minimizing trauma to the leaflets. Engagement surfaces 50 provide an atraumatic surface for deflecting tissue as the fixation device is retracted proximally. It should be further noted that barbs 60 are angled slightly in the distal direction (away from the free ends of the proximal elements 16), reducing the risk that the barbs will catch on or lacerate tissue as the fixation device is withdrawn.

Figure 13A:
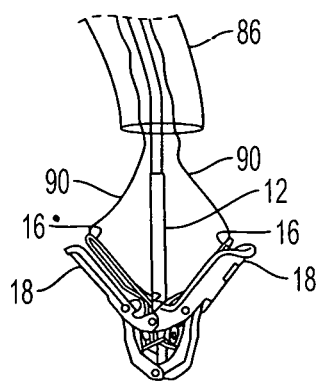
Figure 13B:
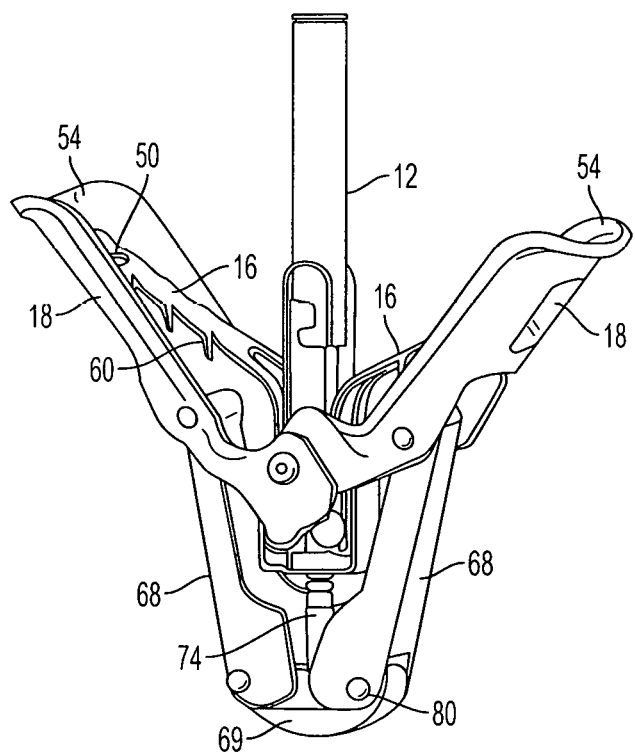

Once the fixation device 14 has been positioned in a desired location against the valve leaflets, the leaflets may then be captured between the proximal elements 16 and the distal elements 18. FIGS. 13A-13B illustrate the fixation device 14 in such a position. Here, the proximal elements 16 are lowered toward the engagement surfaces 50 so that the leaflets are held therebetween. In FIG. 13B, the proximal elements 16 are shown to include barbs 60 which may be used to provide atraumatic gripping of the leaflets. Alternatively, larger, more sharply pointed barbs or other penetration structures may be used to pierce the leaflets to more actively assist in holding them in place. This position is similar to the open position of FIGS. 11A-11B, however the proximal elements 16 are now lowered toward arms 53 by releasing tension on proximal element lines 90 to compress the leaflet tissue therebetween. At any time, the proximal elements 16 may be raised and the distal elements 18 adjusted or inverted to reposition the fixation device 14, if regurgitation is not sufficiently reduced.

Figure 14:
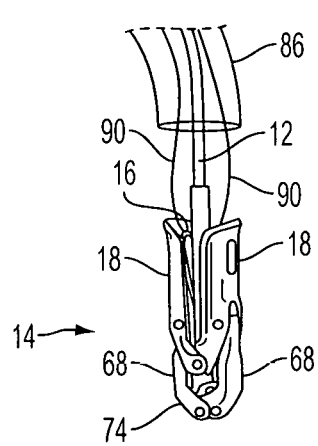

After the leaflets have been captured between the proximal and distal elements 16, 18 in a desired arrangement, the distal elements 18 may be locked to hold the leaflets in this position or the fixation device 14 may be returned to or toward a closed position. Such locking will be described in a later section. FIG. 14 illustrates the fixation device 14 in the closed position wherein the leaflets (not shown) are captured and coapted. This is achieved by retraction of the stud 74 proximally relative to coupling member 19 so that the legs 68 of the actuation mechanism 58 apply an upwards force to the distal elements 18 which in turn rotate the distal elements 18 so that the engagement surfaces 50 again face one another. The released proximal elements 16 which are biased outwardly toward distal elements 18 are concurrently urged inwardly by the distal elements 18. The fixation device 14 may then be locked to hold the leaflets in this closed position as described below.

Figure 15:
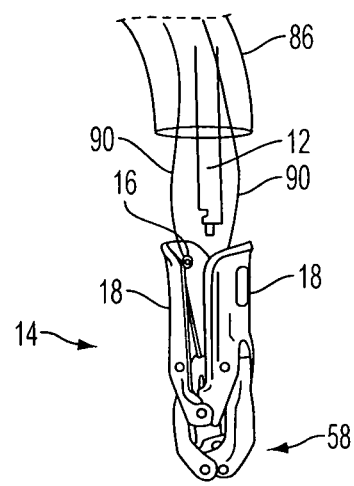

As shown in FIG. 15, the fixation device 14 may then be released from the shaft 12. As mentioned, the fixation device 14 is releasably coupleable to the shaft 12 by coupling member 19. FIG. 15 illustrates the coupling structure, a portion of the shaft 12 to which the coupling member 19 of the fixation device 14 attaches. As shown, the proximal element lines 90 may remain attached to the proximal elements 16 following detachment from shaft 12 to function as a tether to keep the fixation device 14 connected with the catheter 86. Optionally, a separate tether coupled between shaft 12 and fixation device 14 may be used expressly for this purpose while the proximal element lines 90 are removed. In any case, the repair of the leaflets or tissue may be observed by non-invasive visualization techniques, such as echocardiography, to ensure the desired outcome. If the repair is not desired, the fixation device 14 may be retrieved with the use of the tether or proximal element lines 90 so as to reconnect coupling member 19 with shaft 12.

In an exemplary embodiment, proximal element lines 90 are elongated flexible threads, wire, cable, sutures or lines extending through shaft 12, looped through proximal elements 16, and extending back through shaft 12 to its proximal end. When detachment is desired, one end of each line may be released at the proximal end of the shaft 12 and the other end pulled to draw the free end of the line distally through shaft 12 and through proximal element 16 thereby releasing the fixation device.

Figure 16:
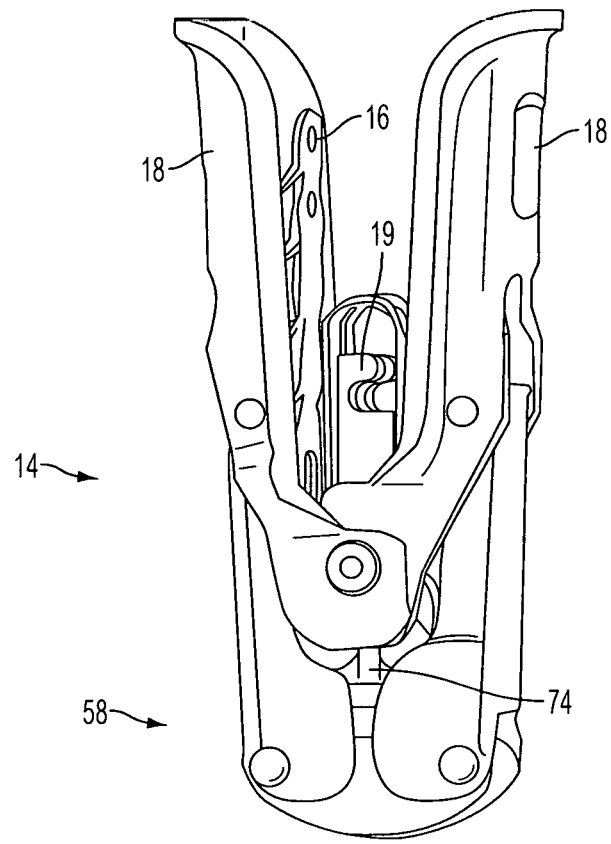

FIG. 16 illustrates a released fixation device 14 in a closed position. As shown, the coupling member 19 remains separated from the shaft 12 of the interventional tool 10 and the proximal elements 16 are deployed so that tissue (not shown) may reside between the proximal elements 16 and distal elements 18.

Figure 17A:
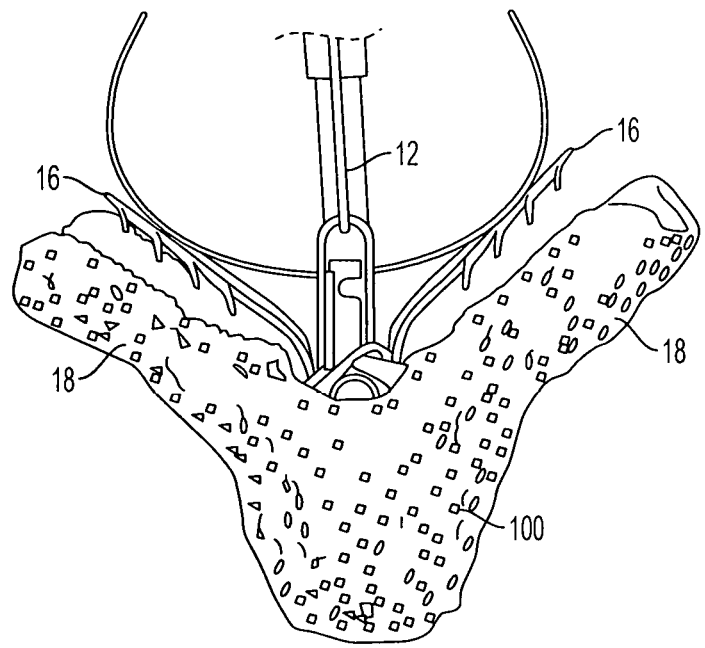
FIGS. 17A-17C illustrate the fixation device in various positions.
Figure 17B:
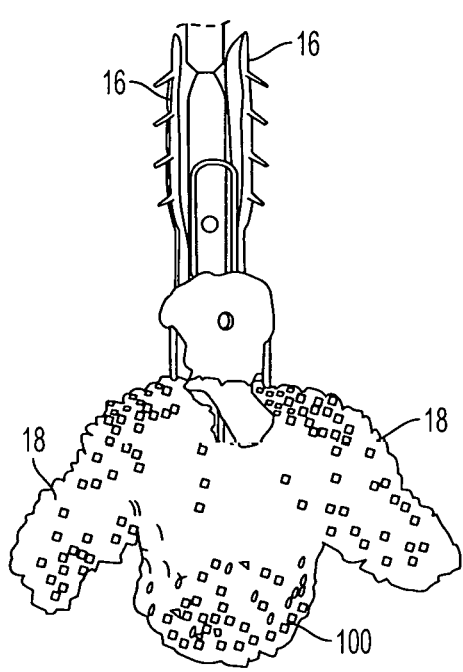
Figure 17C:
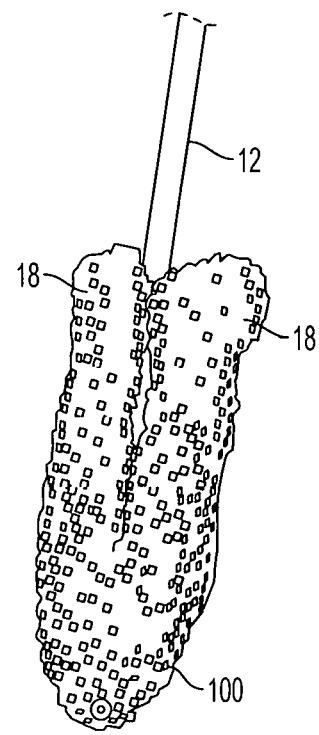

FIGS. 17A-17C illustrate a covering 100 on the fixation device 14 wherein the device 14 is in various positions. FIG. 17A shows the covering 100 encapsulating the distal elements 18 and the actuation mechanism 58 while the device 14 is in the open position. Thus, the engagement surfaces 50 are covered by the covering 100 which helps to minimize trauma on tissues and provides additional friction to assist in grasping and retaining tissues. FIG. 17B shows the device 14 of FIG. 17A in the inverted position. The covering 100 is loosely fitted and/or is flexible or elastic such that the device 14 can freely move to various positions and the covering 100 conforms to the contours of the device 14 and remains securely attached in all positions. FIG. 17C shows the device 14 in the closed position. Thus, when the fixation device 14 is left behind as an implant in the closed position, the exposed surfaces of the device 14 are substantially covered by the covering 100. It may be appreciated that the covering 100 may cover specific parts of the fixation device 14 while leaving other parts exposed. For example, the covering 100 may comprise sleeves that fit over the distal elements 18 and not the actuation mechanism 58, caps that fit over the distal ends 54 of the distal elements 18 or pads that cover the engagement surfaces 50, to name a few. It may be appreciated that, the covering 100 may allow any frictional accessories, such as barbs, to be exposed. Also, the covering 100 may cover the proximal elements 16 and/or any other surfaces of the fixation device 14. In any case, the covering 100 should be durable to withstand multiple introduction cycles and, when implanted within a heart, a lifetime of cardiac cycles.

The covering 100 may alternatively be comprised of a polymer or other suitable materials dipped, sprayed, coated or otherwise adhered to the surfaces of the fixation device 14. Optionally, the polymer coating may include pores or contours to assist in grasping the tissue and/or to promote tissue ingrowth.

Figure 18:
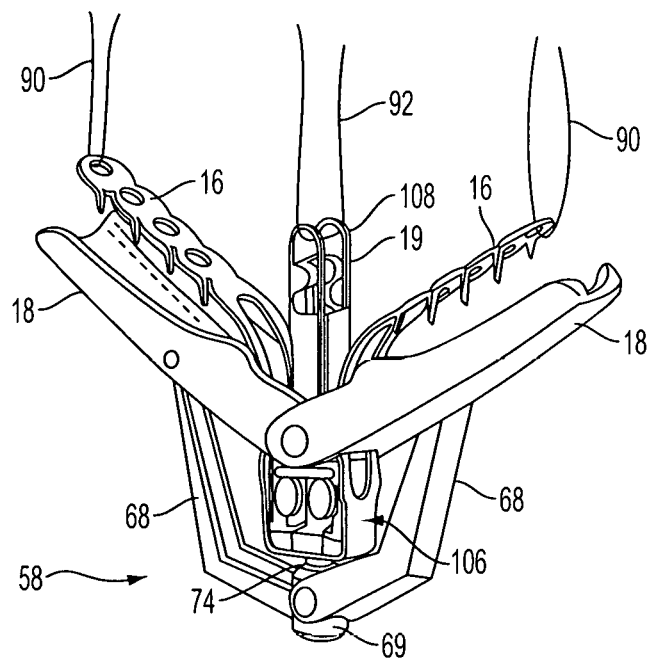
FIGS. 18-19 illustrate an embodiment of the fixation device including proximal elements and a locking mechanism.

Any of the coverings 100 may optionally include drugs, antibiotics, anti-thrombosis agents, or anti-platelet agents such as heparin, COUMADIN® (Warfarin Sodium), to name a few. These agents may, for example, be impregnated in or coated on the coverings 100. These agents may then be delivered to the grasped tissues surrounding tissues and/or bloodstream for therapeutic effects C. Fixation Device Locking Mechanisms As mentioned previously, the fixation device 14 optionally includes a locking mechanism for locking the device 14 in a particular position, such as an open, closed or inverted position or any position therebetween. It may be appreciated that the locking mechanism includes an unlocking mechanism which allows the device to be both locked and unlocked. FIGS. 18-21 illustrate an embodiment of a locking mechanism 106. Referring to FIG. 18, in this embodiment, the locking mechanism 106 is disposed between the coupling member 19 and the base 69 of the actuation mechanism 58. The base 69 is fixedly attached to the stud 74 which extends through the locking mechanism 106. The stud 74 is releasably attached to the actuator rod 64 which passes through the coupling member 19 and the shaft 12 of the interventional tool 10. The base 69 is also connected to the legs 68 of the actuation mechanism 58 which are in turn connected to the distal elements 18.

FIG. 18 also illustrates the proximal elements 16, which in this embodiment straddle the locking mechanism and join beneath the locking mechanism 106. The proximal elements 16 are shown supported by proximal element lines 90. The proximal elements 16 are raised and lowered by manipulation of the proximal element lines 90. In addition, lock lines 92 are shown connected with a release harness 108 of the locking mechanism 106. The lock lines 92 are used to lock and unlock the locking mechanism 106 as will be described below. The proximal element lines 90 and lock lines 92 may be comprised of any suitable material, typically wire, nitinol wire, cable, suture or thread, to name a few. In addition, the proximal element lines 90 and/or lock lines 92 may include a coating, such as parylene. Parylene is a vapor deposited pinhole free protective film which is conformal and biocompatible. It is inert and protects against moisture, chemicals, and electrical charge.

Figure 19:
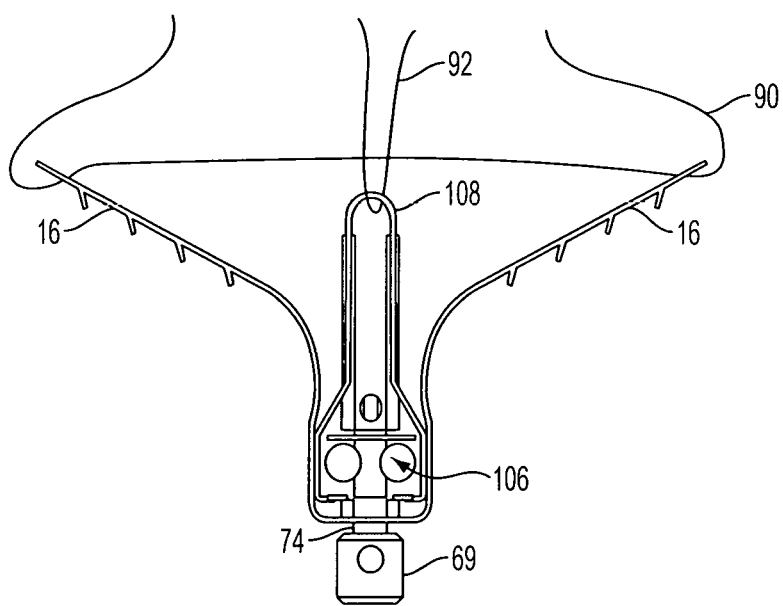

FIG. 19 provides a front view of the locking mechanism 106 of FIG. 18. However, here the proximal elements 16 are supported by a single proximal element line 90 which is through both of the proximal elements 16. In this arrangement both of the elements are raised and lowered simultaneously by action of a single proximal element line 90. Whether the proximal elements 16 are manipulated individually by separate proximal element lines 90 or jointly by a single proximal element line 90, the proximal element lines 90 may extend directly through openings in the proximal elements and/or through a layer or portion of a covering 100 on the proximal elements, or through a suture loop above or below a covering 100.

Figure 20:
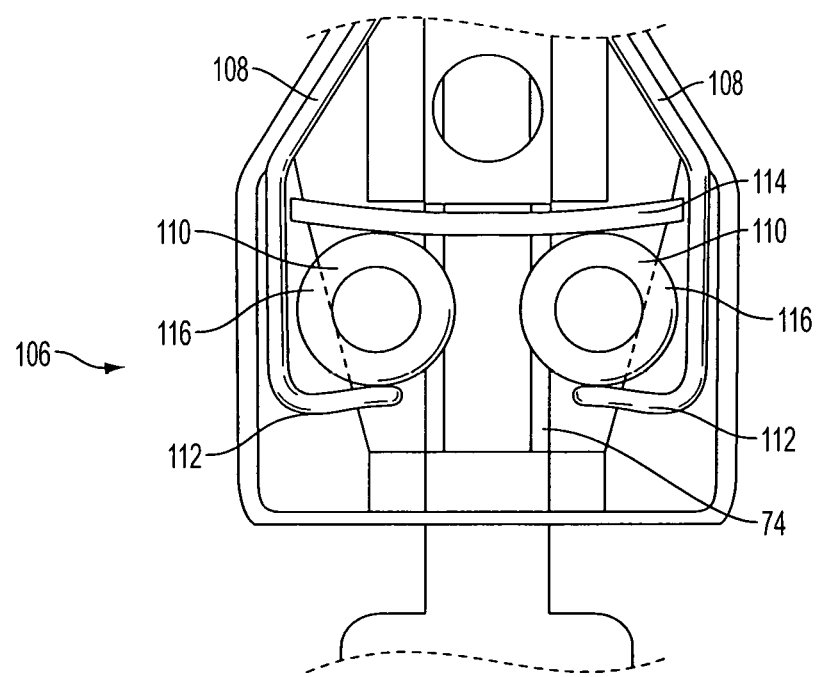
FIGS. 20-21 provide a cross-sectional view of the locking mechanism in the unlocked and locked positions respectively.
Figure 21:
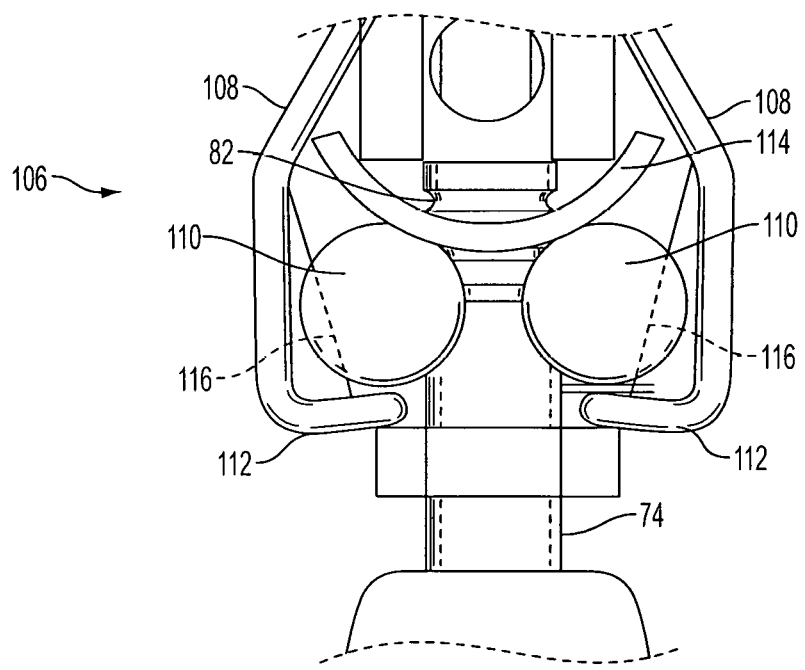

FIGS. 20-21 illustrate the locking mechanism 106 showing the locking mechanism 106 in the unlocked and locked positions respectively. Referring to FIG. 20, the locking mechanism 106 includes one or more wedging elements, such as rolling elements. In this embodiment, the rolling elements comprise a pair of barbells 110 disposed on opposite sides of the stud 74, each barbell having a pair of generally cylindrical caps and a shaft therebetween. The barbells 110 and the stud 74 are preferably comprised of cobalt chromium or stainless steel, however any suitable material may be used. The barbells 110 are manipulated by hooked ends 112 of the release harness 108. When an upwards force is applied to the harness 108 by the lock line 92 (illustrated in FIG. 18), the hooked ends 112 raise the barbells 110 against a spring 114, as shown in FIG. 20. This draws the barbells 110 up along a sidewall or sloping surface 116 which unwedges the barbells 110 from against the stud 74. In this position, the stud 74 is free to move. Thus, when the lock line 92 raises or lifts the harness 108, the locking mechanism 106 is in an unlocked position wherein the stud 74 is free to move the actuation mechanism 58 and therefore the distal elements 18 to any desired position. Release of the harness 108 by the lock line 92 transitions the locking mechanism 106 to a locked position, illustrated in FIG. 21. By releasing the upwards force on the barbells 110 by the hooked ends 112, the spring 114 forces the barbells 110 downwards and wedges the barbells 110 between the sloping surface 116 and the stud 74. This restricts motion of the stud 74, which in turn locks the actuation mechanism 58 and therefore distal elements 18 in place. In addition, the stud 74 may include one or more grooves 82 or indentations which receive the barbells 110. This may provide more rapid and positive locking by causing the barbells 110 to settle in a definite position, increase the stability of the locking feature by further preventing movement of the barbells 110, as well as tangible indication to the user that the barbell has reached a locking position. In addition, the grooves 82 may be used to indicate the relative position of the distal elements 18, particularly the distance between the distal elements 18. For example, each groove 82 may be positioned to correspond with a 0.5 or 1.0 mm decrease in distance between the distal elements 18. As the stud 74 is moved, the barbells 110 will contact the grooves 82; by counting the number of grooves 82 that are felt as the stud 74 is moved, the user can determine the distance between the distal elements 18 and can provide the desired degree of coaptation based upon leaflet thickness, geometry, spacing, blood flow dynamics and other factors. Thus, the grooves 82 may provide tactile feedback to the user.

The locking mechanism 106 allows the fixation device 14 to remain in an unlocked position when attached to the interventional tool 10 during grasping and repositioning and then maintain a locked position when left behind as an implant. It may be appreciated, however, that the locking mechanism 106 may be repeatedly locked and unlocked throughout the placement of the fixation device 14 if desired. Once the final placement is determined, the lock line 92 and proximal element lines 90 are removed and the fixation device is left behind.

While the above described embodiments of the invention utilize a push-to-open, pull-to-close mechanism for opening and closing distal elements 18, it should be understood that a pull-to-open, push-to-close mechanism is equally possible. For example, distal elements 18 may be coupled at their proximal ends to stud 74 rather than to coupling member 19, and legs 68 may be coupled at their proximal ends to coupling member 19 rather than to stud 74. In this example, when stud 74 is pushed distally relative to coupling member 19, distal elements 18 would close, while pulling on stud 74 proximally toward coupling member 19 would open distal elements 18.

D. Individual Actuation of Proximal Elements

Figure 23:
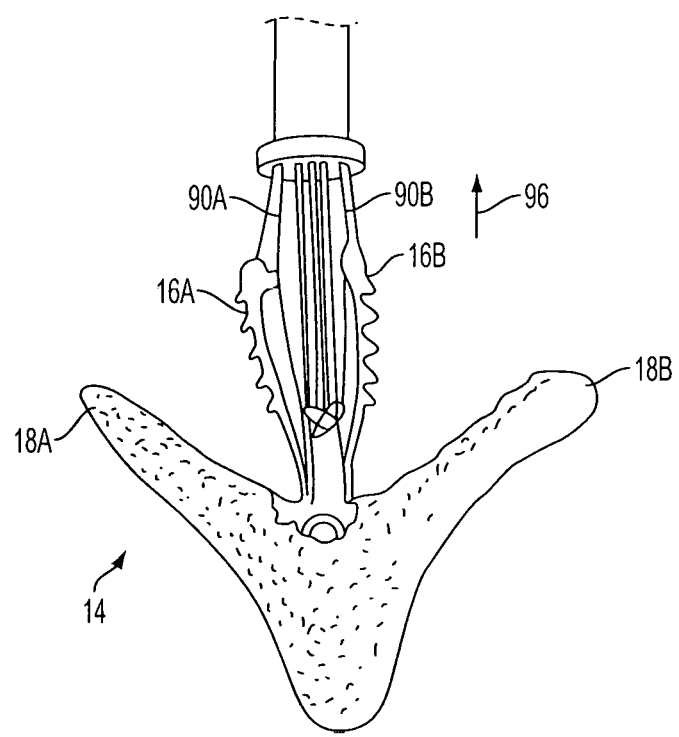

In another embodiment, with reference to FIG. 9, actuation of the proximal elements 16 may be accomplished by using one or more proximal element lines or actuators 90. Such actuation can be achieved in various ways. For example, as shown in FIG. 22A, the proximal element actuators 90A and 90B could be threaded through line loops 48A and 48B, which are disposed on the radially outward and proximal sides of the proximal elements 16A and 16B, respectively. The distal ends of proximal element actuators 90A and 90B may comprise closed loops 95A and 95B, which encircle the shaft 12 and the coupling member 19 shown in FIG. 22A as coupled together. As discussed above, the shaft 12 and the coupling member 19 can be releasably coupled together. To have the closed loops 95A and 95B surround shaft 12 and the coupling member 19, the closed loops 95A and 95B are placed over the shaft 12 and/or the coupling member 19 prior to the coupling shaft 12 and the coupling member 19 together. When the closed loops 95A and 95B encircle the shaft 12 and the coupling member 19, the closed loops 95A and 95B hold the distal ends of the proximal element actuators 90A and 90B in place relative to the shaft 12 and the coupling member 19 and restrict the degree to which the proximal element actuators 90A and 90B can be retracted. By being threaded through the line loops 48A and 48B, the proximal element actuators 90A and 90B are mechanically linked to the proximal elements 16A and 16B, respectively. Thus, as shown in FIG. 23, when the proximal element actuators 90A and 90B are retracted proximally in a direction 96, they move the proximal elements 16A and 16B away from the distal elements 18A and 18B, respectively. Similarly, pushing the proximal element actuators 90A and 90B distally moves the proximal elements 16A and 16B toward the distal elements 18A and 18B.

In another embodiment, to enable the proximal element actuators 90A and 90B to pull the proximal elements 16A and 16B proximally, as well as push the proximal elements 16A and 16B distally, each of the proximal element actuators 90A and 90B may be configured with a thin wire portion 90D and a thick wire portion 90E. The thin wire portions 90D extend from the loops 48A and 48B to the thick wire portions 90E. This thin wire portions 90D enable the proximal element actuators 90A and 90B to be retracted through the line loops 48A and 48B when the proximal element actuators are pulled proximally. On the other hand, the thick wire portions 90E have a stiffness that prevents these portions of the proximal element actuators 90A and 90B from passing through the loops 48A and 48B as the stiffer sections cannot easily bend to make the turn required to extend through the loops 48A and 48B toward the shaft 12. Thus, when the proximal element actuators 90A and 90B are pushed to the point where the thick wire portions 90E reach the loops 48A and 48B, the proximal element actuators 90A and 90B function to push the proximal elements 16A and 16B toward the distal elements 18A and 18B, respectively.

Figure 59A:
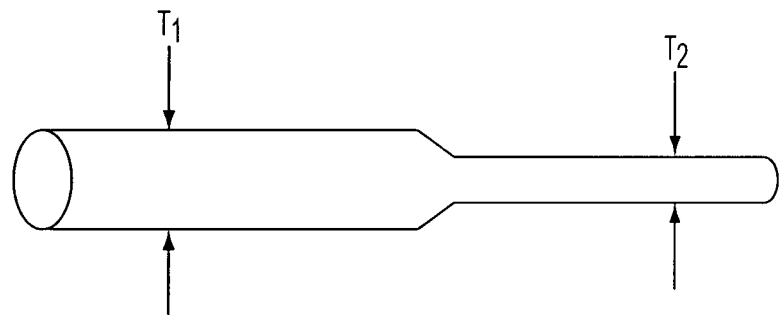
FIGS. 59A and 59B illustrate the configuration of a proximal element actuator.
Figure 59B:
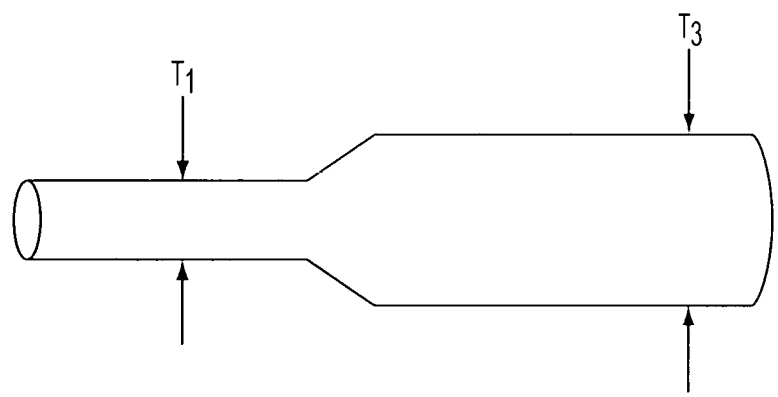
Figure 60A:
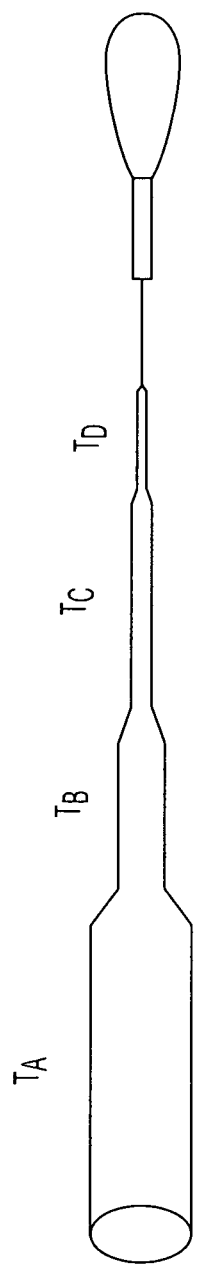
FIGS. 60A and 60B illustrate another configuration of a proximal element actuator.
Figure 60B:
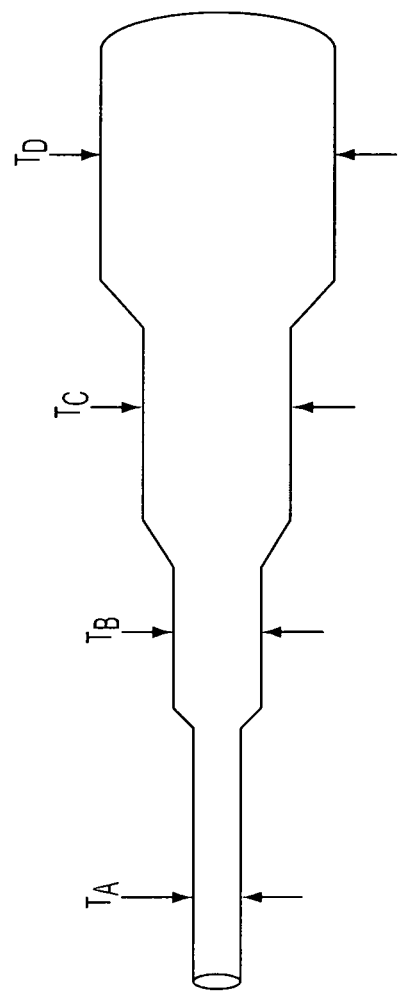

FIGS. 59A and 59B show an embodiment in which thick wire portions 90E are formed by rolling an end of a round thin wire portion 90D. In particular, the rolling of the round portion of the wire results in a cross section having a thick portion T3 formed as a result of rolling to reduce the round section thickness T1 to a thickness T2. This results in a substantially rectangular shaped cross section having the dimensions T2 and T3. Notably, T3 is greater than T1 and T2 is less than T1. As a result of this flattening of the end of the proximal element actuators 90A and 90B, the bending characteristics of the end portion is changed. That is, under a compressive load, the bending will tend to occur along the plane of the FIG. 59A and not in the plane of FIG. 59B. The round portion (thin) may have a diameter in the range of 0.009 to 0.012 inches whereas the thick portion may have a width ranging from 0.013 to 0.02 inches. Also, as shown in FIGS. 60A and 60B, the proximal element actuators 90A and 90B may be formed with multiple thick portions that thicken toward the distal end of the actuators. As shown in FIG. 60B, TA<TB<TC<TD.

In another embodiment as shown in FIG. 22B, as an alternative to using a thick/thin wire combination, the proximal element actuators 90A and 90B may comprise a thin wire contained within an outer tube 90G. In this embodiment, instead of relying on a stiffer thick wire portion, the proximal element actuators include an outer tube 90G to push the proximal elements 16A and 16B distally. The outer tube 90G may comprise, for example, a braided polyamide tube.

By using a thick wire portion or an outer tube, the proximal elements 16A and 16B can be pushed or position distally toward the distal elements with more force. In contrast, when configured such the proximal elements 16A and 16B are biased to extend distally in combination with only thin wire proximal element actuators 90A and 90B, the engaging force between the proximal elements 16A and 16B and the distal elements 18A and 18B decreases as the distal elements are moved distally, i.e., such as 120-180 degrees as shown in FIG. 3B. However, when either a thick wire portion or an outer tube is introduced in the proximal elements 16A and 16B, the proximal elements may be pushed distally with more force. This provides more control and better positioning for capturing leaflets during the coapting of the leaflets. Further, when there is a relatively large gap between the leaflets, having the distal elements extending in a 180 degree alignment a shown in FIG. 3B, enables the system to more easily capture the leaflets over this gap or separation. Moreover, the ability to push the proximal elements 16A and 16B over this range (120-180 degrees or more) to engage the distal elements 18A and 18B provides an response as well as improved geometry for leaflet grasping.

Figure 24:
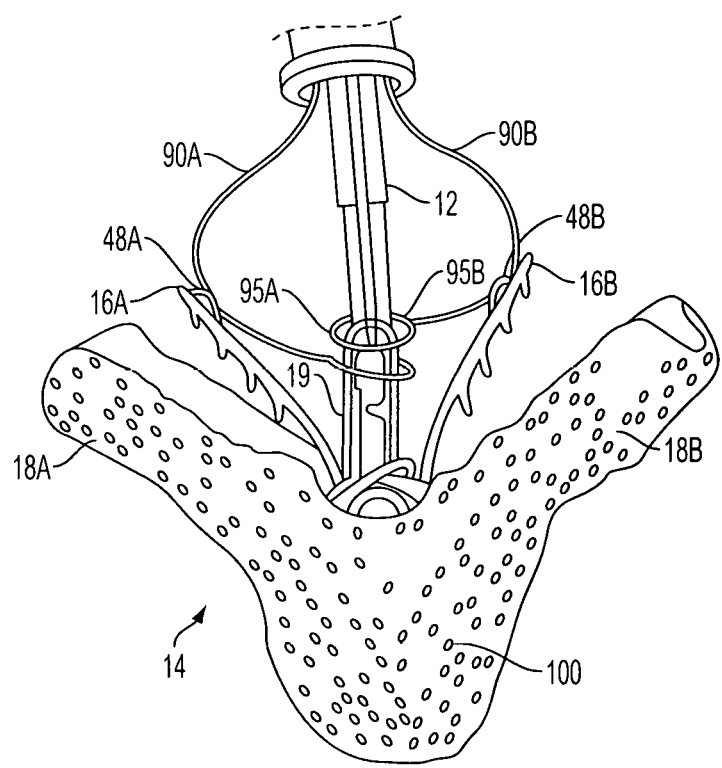
Figure 27:
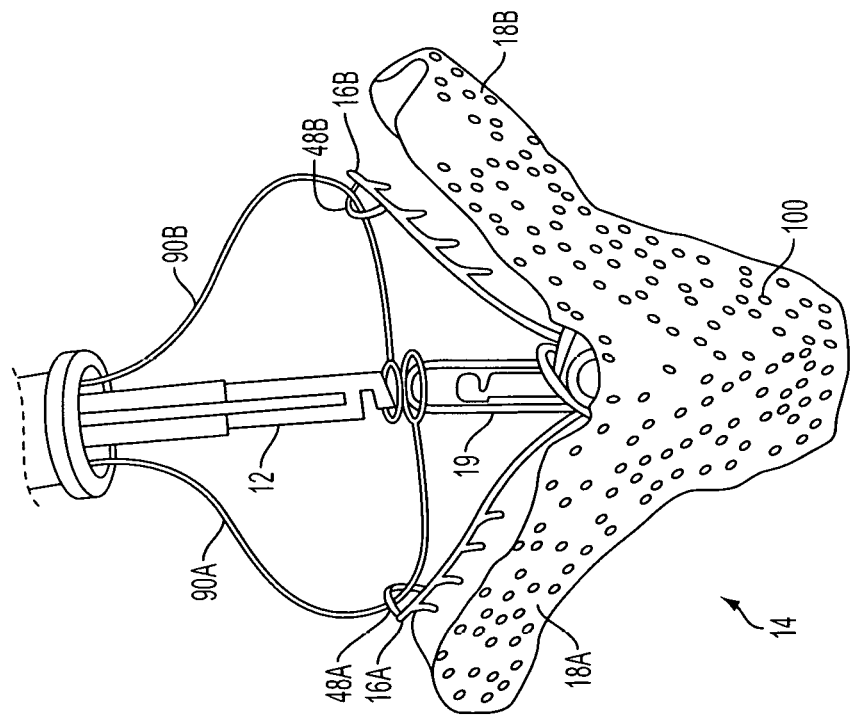

The proximal element actuators 90A and 90B may be moved so that the proximal elements 16A and 16B are moved at a variety of angles and distances from the distal elements 18A and 18B. And, the degree to which the proximal element actuators 90A and 90B are pushed or pulled can be maintained to keep the positions of the proximal elements 16A and 16B have relative to the distal elements 18. For example, as shown in FIG. 24, the proximal element actuators 90A and 90B are pulled proximally and maintained in the position shown so as to maintain the proximal elements 16A and 16B in an intermediate position relative to the distal elements 18. This intermediate position is between a position in which the proximal elements 16A and 16B are biased toward and that in which the proximal elements 16A and 16B are fully retracted as in FIG. 23. As shown in FIG. 27, once the proximal elements 16A and 16B are in a desired position, the shaft 12 and the coupling member 19 can be decoupled so that proximal retraction of the proximal element actuators 90A and/or 90B decouples the proximal element lines from the proximal elements 16. Thus, the fixation device 14 can be left in place while the shaft 12, the proximal element actuators 90A and 90B, and other parts can be removed from a site of operation. As shown in FIGS. 22 through 28, the fixation device 14 typically includes a covering 100 substantially the same as discussed in FIGS. 16A-16C below.

Figure 25:
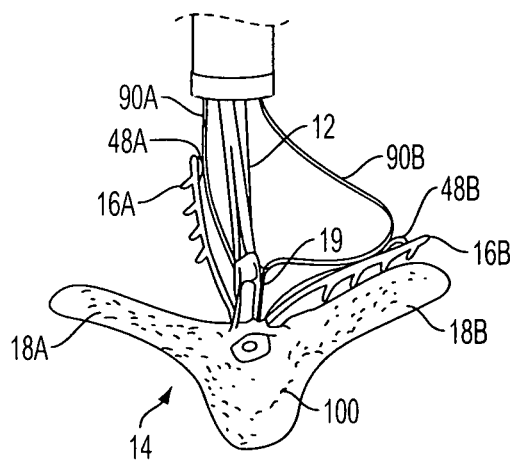
Figure 26:
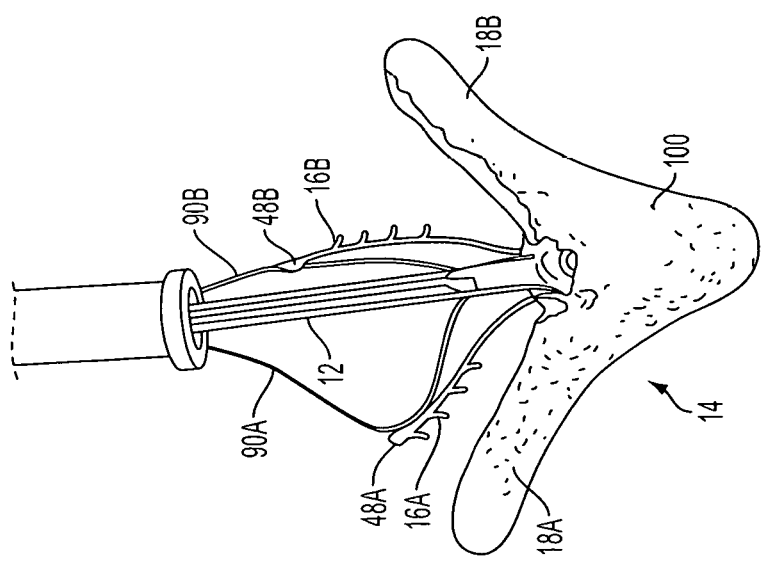

It may be desirable to provide for independent actuation of the proximal elements 16A and 16B. For example, as shown in FIG. 25, the proximal element actuator 90A is proximally retracted and rotates the proximal element 16A away from the distal element 18A, while the proximal element actuator 90B is pushed distally and rotates the proximal element 16B toward the distal element 18B. Similarly, as shown in FIG. 26, the proximal element actuator 90A is left alone, allowing the proximal element 16A to maintain the position it is biased toward, while the proximal element actuator 90B is proximally retracted, moving the proximal element 16B away from the distal element 18B. Providing for the independent actuation of the proximal elements 16A and 16B allows leaflets to be independently grasped by the proximal elements 16A and 16B and the distal elements 18A and 18B. Thus, the fixation device 14 can coapt leaflets more easily and at more optimal locations. For example, as opposed to grasping two leaflets simultaneously, a first leaflet can be grasped at a desired position and the fixation device 14 can then be repositioned so that a second leaflet can be grasped at a more optimal position. Alternatively, leaflets may be still be simultaneously grasped if desired as the independently actuatable proximal element actuators can still be moved simultaneously. Also, after leaflets are grasped, they can be released and the leaflets can be grasped again, for example, if the leaflets are malcoapted at the first grasp. The embodiments described about may be utilized with either the s-lock or the l-lock configurations described herein.

Figure 28:
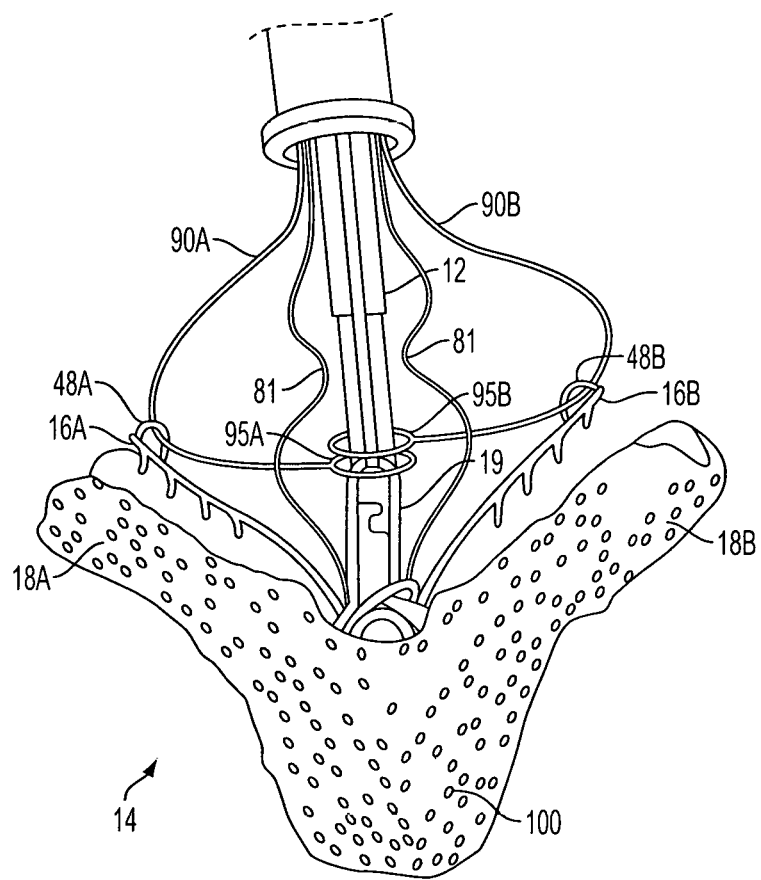
FIG. 28 illustrates another embodiment of a fixation device including a gripper pusher.

Embodiments of the fixation device similar to the devices described above may include both a gripper pusher 81 and independently actuatable proximal elements 16A and 16B, as shown for example in FIG. 28. Having both a gripper pusher 81 and independently actuatable proximal elements 16A and 16B may allow the fixation device to have many of the advantages described above such as to more accurately and more strongly grasp leaflets.

In another embodiment, the proximal element actuators 90A and 90B may each comprise a continuous loop that enters and exits the nose 318 of the shaft 302 as shown in FIG. 18. However, as shown in FIGS. 29-33, the proximal element actuators 90A and 90B may be coupled with the release harness 108 so that the lock lines 92 may be eliminated.

Figure 29:
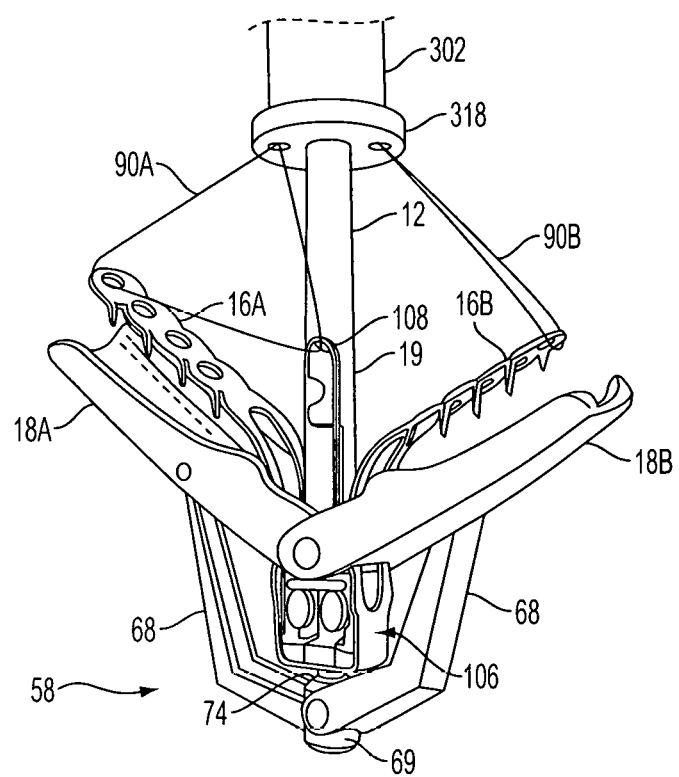
FIG. 29 illustrates an embodiment of a fixation device having independent proximal element actuation.

FIG. 29 illustrates a configuration in which the proximal element actuator 90A is looped through the end of proximal element 16A and the release harness 108. The other proximal element actuator 90B is looped only through the proximal element 16B. Thus, manipulation of the proximal element actuator 90A in this embodiment will actuate the proximal element 16A either proximally or distally to engage or disengage with tissue. After the tissue engagement is completed and the leaflets are properly coapted, the proximal element actuator 90A may be further actuated to release the release harness 108 of the locking mechanism 106. On the other hand, if it determined that the fixation device 14 requires repositioning, applying tension on the proximal element actuator 90A will unlock the locking mechanism. Further actuation of the proximal element actuator 90A may then cause the proximal element 16A to disengage from the leaflet so that repositioning can be performed.

Figure 30:
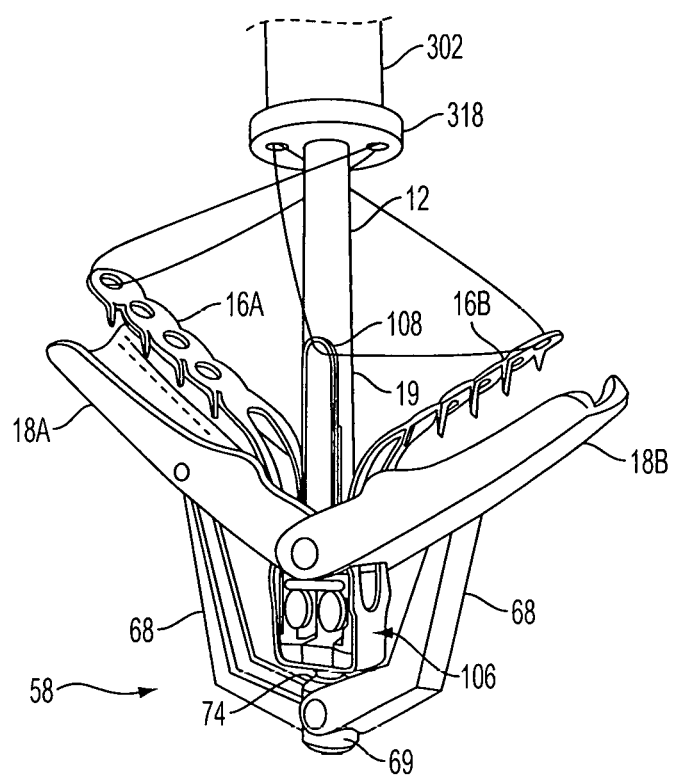
FIG. 30 illustrates another embodiment of a fixation device having independent proximal element actuation.

In another embodiment, as illustrated in FIG. 30, the proximal element actuators 90A and 90B may be configured to cross the shaft 12 to provide better leverage for actuation. Again, in this configuration the proximal element actuator 90A is looped through the end of proximal element 16A and the release harness 108. The other proximal element actuator 90B is looped only through the proximal element 16B. However, crossing the shaft in this manner changes the angular relationship between the point where the proximal element actuators 90A and 90B exit the nose 318 of the shaft 302 and where they connect to a corresponding proximal element 16A and 16B. As such, the resultant force of actuation on the proximal elements 16A and 16B is increased for a given amount of tension on the proximal element actuators 90A and 90B as shown in the configuration of FIG. 29. This arrangement also allows for elimination of the lock lines 92. As illustrated in FIG. 29, each of the proximal element actuators 90A and 90B may straddle the shaft 12. However, the lines may also be routed to cross on the same side of the shaft 12.

Figure 31:
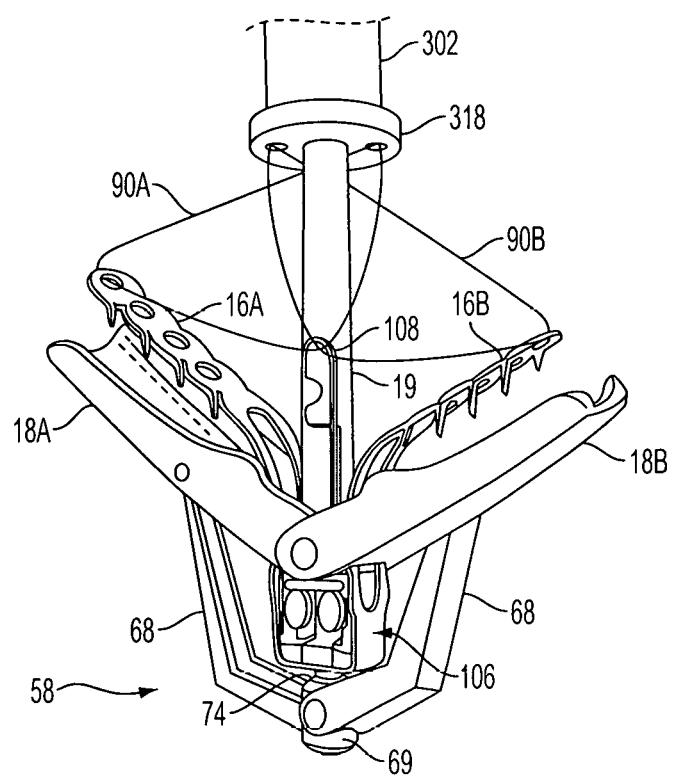
FIG. 31 illustrates another embodiment of a fixation device having independent proximal element actuation.

FIG. 31 shows another configuration of routing the proximal element actuators 90A and 90B. In this configuration, the proximal element actuator 90A and proximal element actuator 90B are each coupled with the one of the proximal elements 16A and 16B and the release harness 108. While the embodiment shown in FIG. 30 locks the fixation device 14 only after the proximal element 16A is moved into an engagement position with a leaflet, the configuration of FIG. 31 permits the operator to control the sequence of leaflet engagement between proximal elements 16A and 16B. In other words, the proximal element actuator 90A need not be actuated after locking the fixation device 14 in the event an operator merely elects to actuate proximal element 16B.

Figure 32:
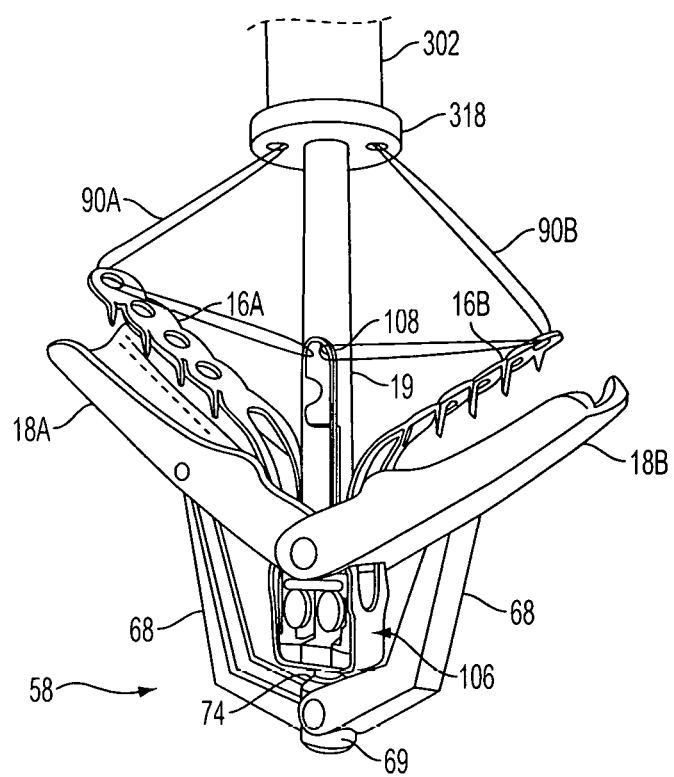
FIG. 32 illustrates another embodiment of a fixation device having independent proximal element actuation.
Figure 33:
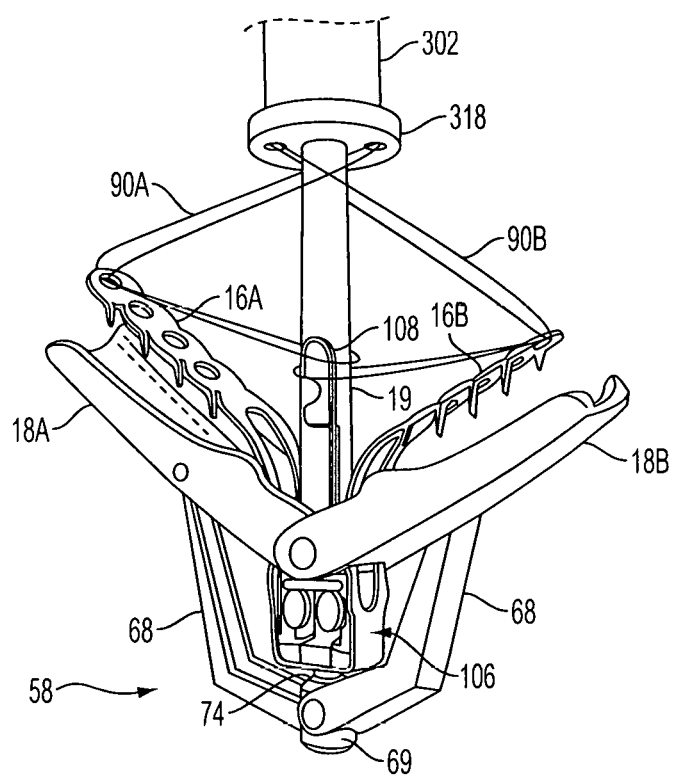
FIG. 33 illustrates another embodiment of a fixation device having independent proximal element actuation.

FIGS. 32 and 33 illustrate another possible configuration for the proximal element actuators 90A and 90B. Each proximal element actuator comprises a loop that exits from and returns to the nose 318. However, in this case, the proximal element actuators 90A and 90B are each double threaded through the end of a corresponding one of the proximal elements 16A and 16B and then looped around the release harness 108. In FIG. 32 the proximal element actuator 90A exits the nose 318 on a side of the nose 318 adjacent to the proximal element 16A and the proximal element actuator 90B exits the nose 318 on a side of the nose 318 adjacent to the proximal element 16B. In an alternative configuration, the proximal element actuator 90A exits the nose 318 on a side of the nose 318 opposite to the proximal element 16A and the proximal element actuator 90B exits the nose 318 on a side of the nose 318 opposite to the proximal element 16B. Crossing the shaft in this manner changes the angular relationship between the point where the proximal element actuators 90A and 90B exit the nose 318 of the shaft 302 and where they connect to a corresponding proximal element 16A and 16B. As such, the resultant force of actuation on the proximal elements 16A and 16B is increased for a given amount of tension on the proximal element actuators 90A and 90B.

In each of the embodiments of FIGS. 29-33, each of the proximal element actuators 90A and 90B may be formed of a single line, which may be formed of a single or multiple filaments, that extends from and returns to the nose 318 of the shaft 302. However, in the embodiments of FIGS. 32 and 33, the proximal element actuators 90A and 90B may only extend from the nose 318 and then terminate at the coupling shaft 12 or the coupling member 19 as shown in FIG. 24.

E. Individual Actuation of Proximal Elements/Single Actuator

Figure 34:
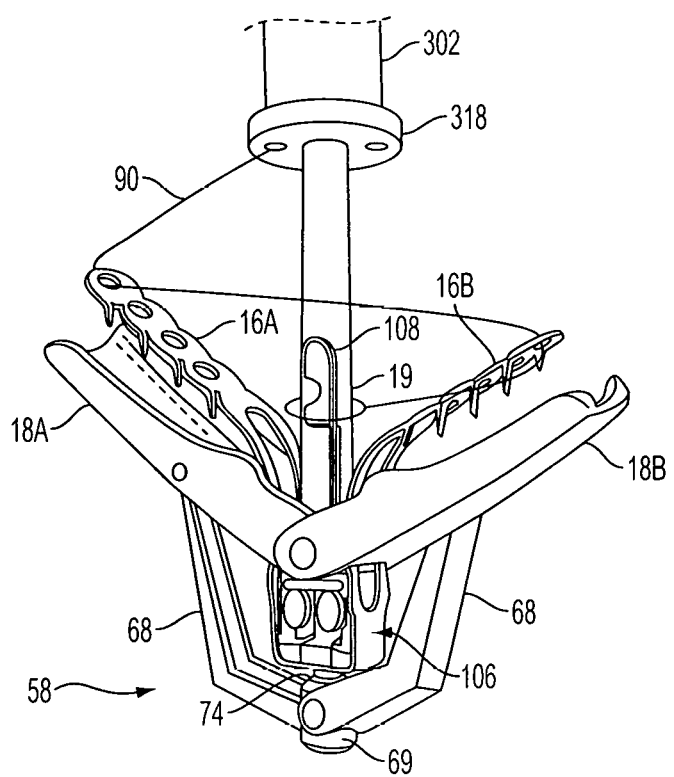
FIGS. 34-35 illustrates another embodiment of a fixation device having independent proximal element actuation with a single actuator.

In other embodiments, sequential grasping may be accomplished by use of a single actuator. FIG. 34 illustrates a configuration wherein a single proximal element actuator 90, having a proximal end and a distal end, extends from the nose 318 of the shaft 302 to one of the proximal elements 16A. It may be looped through an eyelet at a distal end of the proximal element 16A or held by a suture at the same location. The same proximal element actuator 90 then extends across the coupling shaft 12 to the other proximal element 16B where it is coupled to the distal end of this proximal element 16b in a manner similar to proximal element 16A. The distal end of this proximal element actuator 90 extends to either of the coupling shaft 12 or the coupling member 19 where it is secured. In FIG. 34 it is secured using a loop. However, the proximal element actuator may be releasable fixed to the fixing device 14 in accord in any of the embodiments disclosed below.

Figure 35:
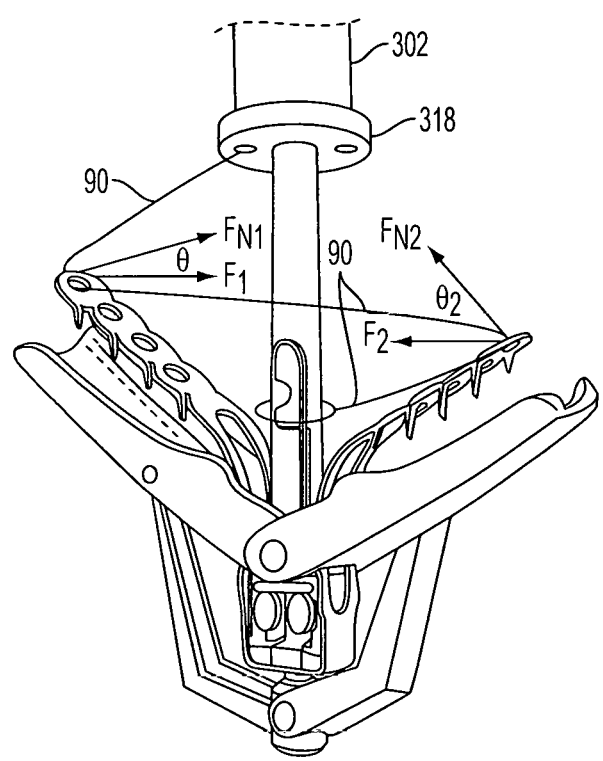

By virtue of the geometry of this configuration, each proximal element 16A and 16B may be independently actuated and the proximal element actuator 90 may be released in tandem with the separation of the coupling member 19. As illustrated in FIG. 35, due to the manner of routing the proximal element actuator 90, the resultant forces $F_1$ and $F_2$ are at different angles. These resultant forces and their directions are based on the tension on the proximal element 90 and the direction (angle) at which the proximal element actuator 90 approaches and extends away from a corresponding proximal element 16 A or 16B. The force that causes a corresponding proximal element to move is the component of the force that is perpendicular to the length of a corresponding proximal element. This perpendicular component is represented by $F_{N1}$ and $F_{N2}$. A smaller angle ($\theta_1$, $\theta_2$) between the resultant force and the perpendicular component leads to a larger perpendicular component. As illustrated in FIG. 35, because the angle $\theta_1$ is smaller than the angle $\theta_2$, the perpendicular component $F_{N1}$ will be larger that the perpendicular component $F_{N2}$. Accordingly, for a given amount of tension in the proximal element actuator 90, proximal element 16A will receive more moving force than proximal element 16B. That means that proximal element 16B will remain closed as proximal element 16A opens, and proximal element 16B will open after proximal element 16A is fully opened. This allows for independent actuation of the proximal elements 16A and 16B using a single proximal element actuator 90.

F. Gripper Pusher to Engage Proximal Elements

In some situations, the valve leaflets may fully or partially detach from the fixation device due to poor leaflet insertion between the proximal and distal elements. Evaluation of valve leaflet insertion in the fixation device is therefore performed using standard imaging technology such as echocardiography and fluoroscopy. However, depending on the angle and/or position of the proximal and distal elements relative to the delivery catheter, it can be challenging to assess the depth of valve leaflet insertion into the fixation device, or to differentiate between the leaflets and the proximal and distal elements of the fixation device. Visualization is therefore preferably performed with the distal elements in a more open configuration with the distal elements displaced from one another. However, since many current embodiments of the fixation device only permit the proximal elements to open up to an included angle of about 85°, the distal elements therefore must be closed up to an included angle of between about 45° and preferably 60° in order securely grasp the valve leaflets between the proximal and distal elements. While this configuration helps an operator visualize and differentiate between the valve leaflets and the fixation device, it is preferable to further open up the distal elements to an included angle of greater than 90°, and more preferably to 120° or more. Thus, it would be desirable to modify the proximal elements to open up further.

Figure 36:
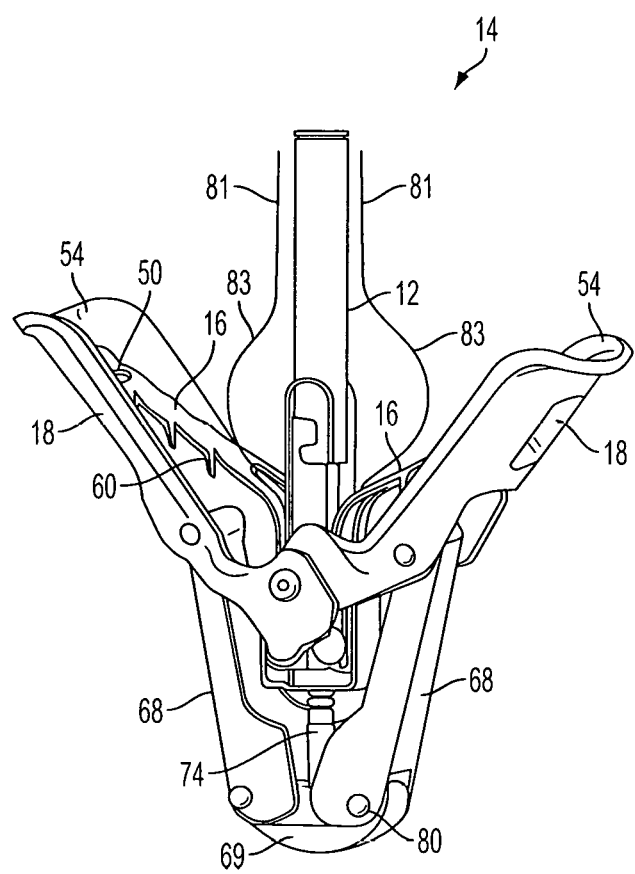
FIGS. 36-40 illustrate the fixation device of FIG. 9 with a gripper pusher.

FIGS. 36-40 illustrate an embodiment of a fixation device similar to the device of FIGS. 7A-14, with a major difference being that this embodiment includes a gripper pusher. FIG. 36 illustrates fixation device 14 that generally takes the same form as fixation device 14 previously described. In addition to the features previously described, fixation device 14 also includes a gripper pusher 81. The gripper pusher 81 deflects radially outward resulting in a bowed region 83 that expands outward until the bowed region 83 engages a superior surface of the proximal elements 16. As the bowed region 83 continues to deflect radially outward, it further pushes on the proximal elements 16 such that the proximal elements are deflected and rotated outward toward the engagement surface of the distal elements 18. Thus, the proximal elements 16 may be deflected outward further than they normally would, and therefore the valve leaflets may be captured between the proximal and distal elements when the distal elements are disposed in a more open position with a larger included angle therebetween. In preferred embodiments, the included angle between the distal elements is greater than about 90°, preferably greater than about 110°, and more preferably greater than about 120°. In the embodiment of FIG. 36, the gripper pusher 81 includes two arms formed from a metal, polymer or other wire-like material. Exemplary materials include cobalt chromium alloy, stainless steel, nitinol, and the like. Polymers may also be used to fabricate the gripper pusher. The gripper pusher 81 may be actuated to bow outwards upon application of an axially oriented compressive force that is generally parallel to the longitudinal axis of the gripper pusher arms. During compression, the gripper pusher bows outward forming bowed region 83. In other embodiments, the gripper pusher may be a spring which is resiliently biased to bow outward forming bowed region 83. However, when proximal element lines (not illustrated here) are tensioned to lift the proximal elements 16, the gripper pusher springs will collapse to a reduced profile.

Figure 37:
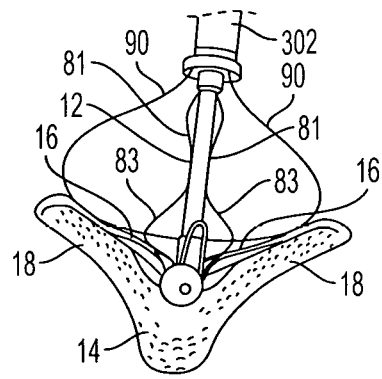
Figure 38:
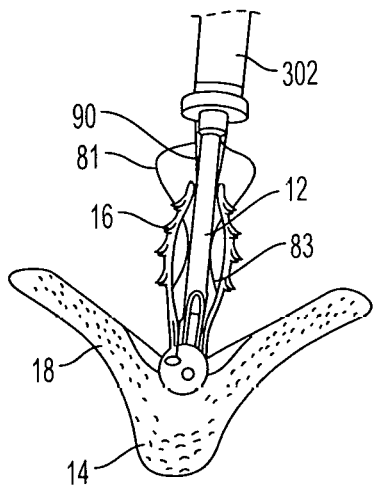

FIG. 37 illustrates the fixation device 14 having a covering for tissue ingrowth, and with the gripper pusher 81 expanded such that the proximal elements 16 (also referred to as gripping elements) are in engagement with the distal elements 18 (also referred to as fixation elements). The valve leaflets (not shown for convenience) are pinched therebetween. FIG. 38 illustrates the gripper pusher 81 in the collapsed configuration. The bowed region 83 collapses, allowing the proximal elements 16 to retract towards shaft 12, allowing the valve leaflets (not shown) to be released from the fixation device 14. The gripper pusher 83 is offset from the proximal elements 16 so that the proximal elements can retract without interfering with the gripper pusher 81.

Figure 39:
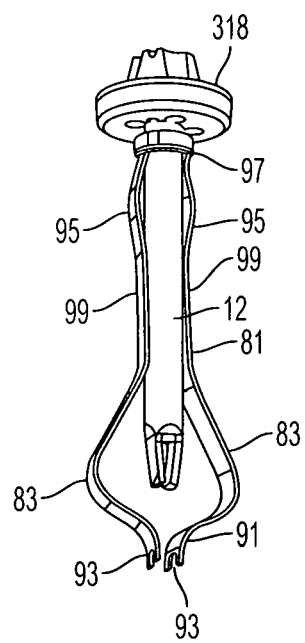
Figure 40:
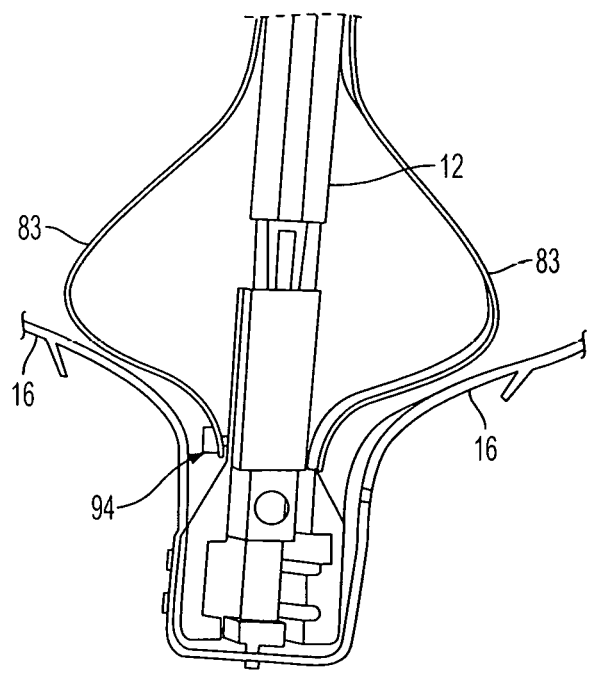

FIG. 39 highlights the gripper pusher 83 which preferably includes two spring arms 99. Each arm 99 is formed from wire or machined from a sheet or other stock material and in this embodiment has a rectangular cross-section, although other cross-sections are also contemplated. A distal portion 91 of each arm 99 has a notched region 93 forming a pair of fingers that can engage with a boss or other attachment mechanism on the fixation device. The notch may be released from the boss when the fixation device 14 is detached from the delivery catheter shaft 12. Additionally, each arm includes two bowed regions, or peaks, including a larger distal bowed region 83, and a smaller proximal bowed region 95. The larger bowed region 83 flares outwardly a greater distance so as to engage and push the proximal elements 16 into engagement with the distal elements 18. When the distal bowed region 83 relaxes and collapses away from the proximal elements 16, or when collapsed by retraction of the proximal elements, the smaller proximal bowed regions 95 expand radially outward. An attachment ring or coupling collar 97 is adjacent nose 318 (described in greater detail below) and is slidably disposed over the shaft 12 and allows coupling of the gripper arms 99 to the shaft 12. FIG. 40 illustrates the distal bowed region 83 in engagement with the proximal elements 16, and also illustrates engagement of the notch 93 on the distal portion of each arm 99 with a boss 94 on the fixation device 14.

Figure 42:
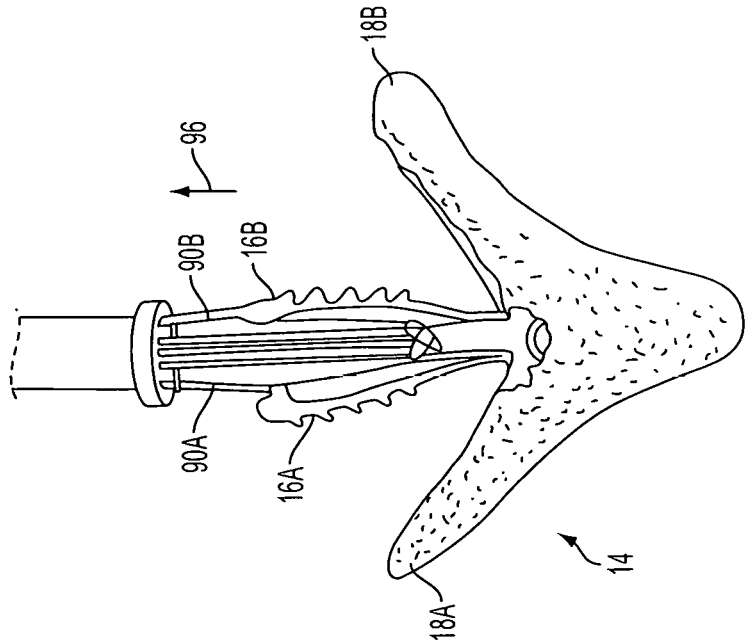
FIGS. 41-46 illustrate another embodiment of a fixation device of with a gripper pusher and independent actuation.
Figure 41:
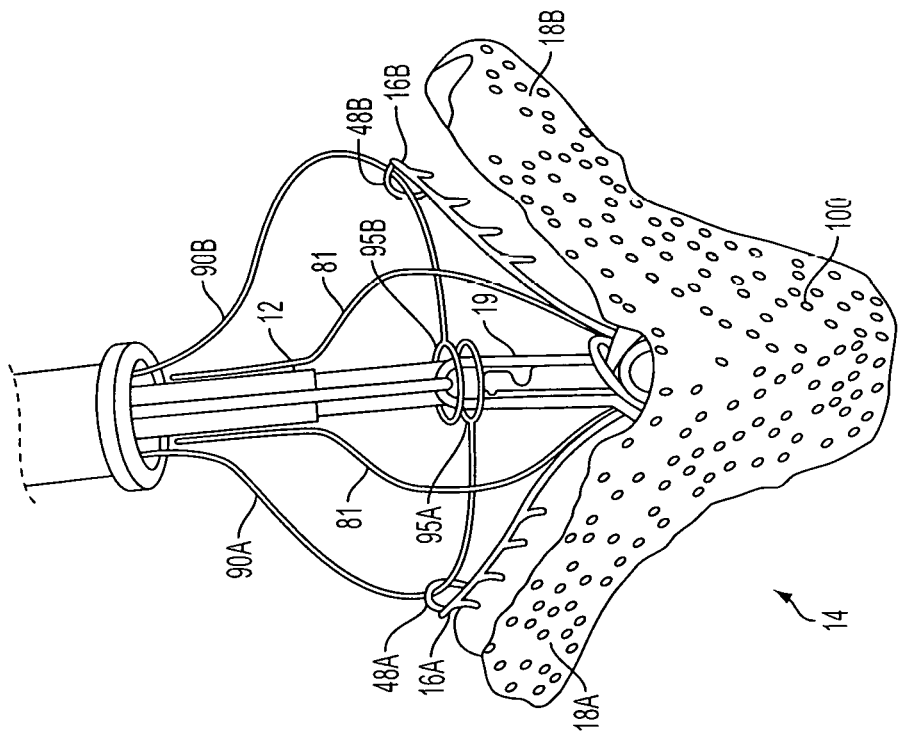

As described above, for example, with reference to FIGS. 10A through 11B, actuation of the proximal elements 16 may be accomplished by using one or more proximal element lines or actuators 90. In another embodiment, this actuation can be achieved by combination of the proximal element actuators 90 and the gripper pusher 81 as set forth above. For example, as shown in FIG. 41, the proximal element actuators 90A and 90B could be threaded through line loops 48A and 48B, which are disposed on the radially outward and proximal sides of the proximal elements 16A and 16B, respectively. The distal ends of proximal element actuators 90A and 90B may comprise closed loops 95A and 95B, which encircle the shaft 12 and the coupling member 19 shown in FIG. 41 as coupled together. As discussed above, the shaft 12 and the coupling member 19 can be releasably coupled together. To have the closed loops 95A and 95B surround shaft 12 and the coupling member 19, the closed loops 95A and 95B are placed over the shaft 12 and/or the coupling member 19 prior to the coupling shaft 12 and the coupling member 19 together. When the closed loops 95A and 95B encircle the shaft 12 and the coupling member 19, the closed loops 95A and 95B hold the distal ends of the proximal element actuators 90A and 90B in place relative to the shaft 12 and the coupling member 19 and restrict the degree to which the proximal element actuators 90A and 90B can be retracted. By being threaded through the line loops 48A and 48B, the proximal element actuators 90A and 90B are mechanically linked to the proximal elements 16A and 16B, respectively. Thus, as shown in FIG. 42, when the proximal element actuators 90A and 90B are retracted proximally in a direction 96, they move the proximal elements 16A and 16B away from the distal elements 18A and 18B, respectively.

However, in combination with the proximal element actuators 90A and 90B, which permit independent actuation of the proximal elements 16A and 16B, the gripper pusher 81 may also be included in the fixation device. Thus, the proximal elements 16A and 16B may be deflected outward further than they normally would, and therefore the valve leaflets may be captured between the proximal and distal elements when the distal elements are disposed in a more open position with a larger included angle therebetween. In preferred embodiments, the included angle between the distal elements is greater than about 90°, preferably greater than about 110°, and more preferably greater than about 120°. Thus, in this embodiment, the fixation device is capable for independent actuation as well as a wide range of proximal element 16A and 16B movement.

Figure 43:
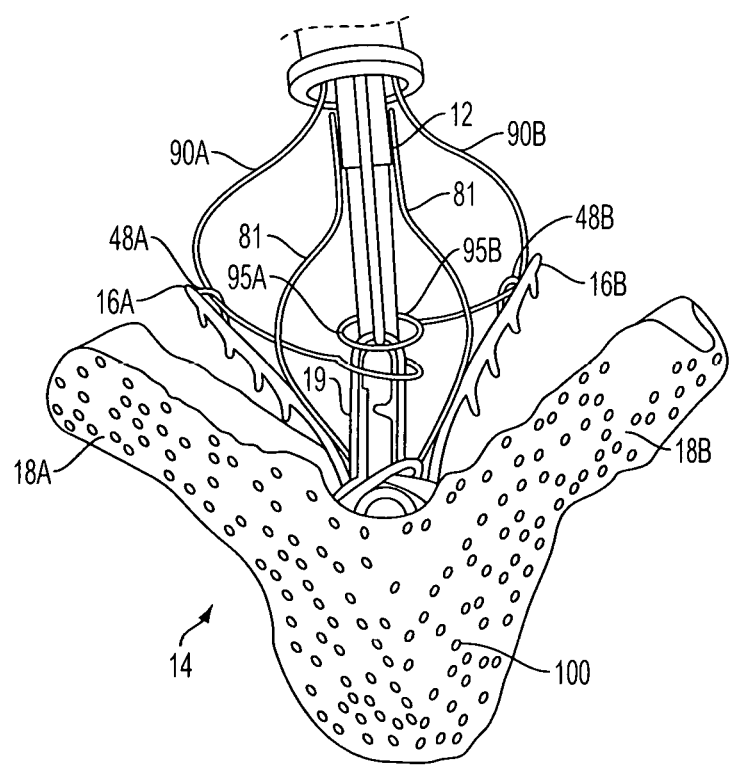
Figure 46:
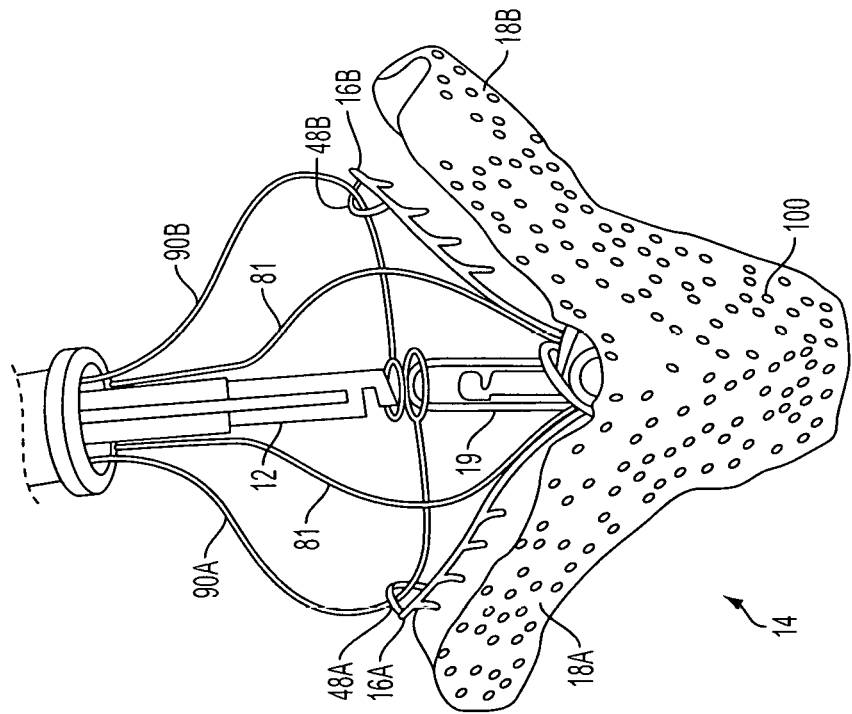

The proximal element actuators 90A and 90B may be moved so that the proximal elements 16A and 16B are moved at a variety of angles and distances from the distal elements 18A and 18B. And, the degree to which the proximal element actuators 90A and 90B are pushed or pulled can be maintained to keep the positions the proximal elements 16A and 16B have relative to the distal elements 18. For example, as shown in FIG. 43, the proximal element actuators 90A and 90B are pulled proximally and maintained in the position shown so as to maintain the proximal elements 16A and 16B in an intermediate position relative to the distal elements 18. This intermediate position is between the position in which the proximal elements 16A and 16B are biased toward and that in which the proximal elements 16A and 16B are fully retracted as in FIG. 42. As shown in FIG. 46, once the proximal elements 16A and 16B are in a desired position, the shaft 12 and the coupling member 19 can be decoupled so that proximal retraction of the proximal element actuators 90A and/or 90B decouples the proximal element lines from the proximal elements 16. Thus, the fixation device 14 can be left in place while the shaft 12, the proximal element actuators 90A and 90B, and other parts can be removed from a site of operation. As shown in FIGS. 41 through 47, the fixation device 14 typically includes a covering 100.

Figure 44:
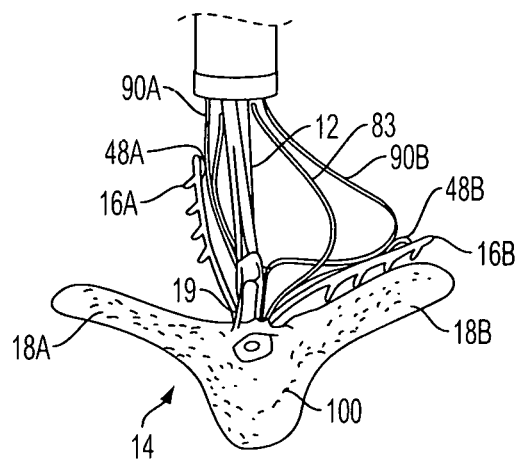
Figure 45:
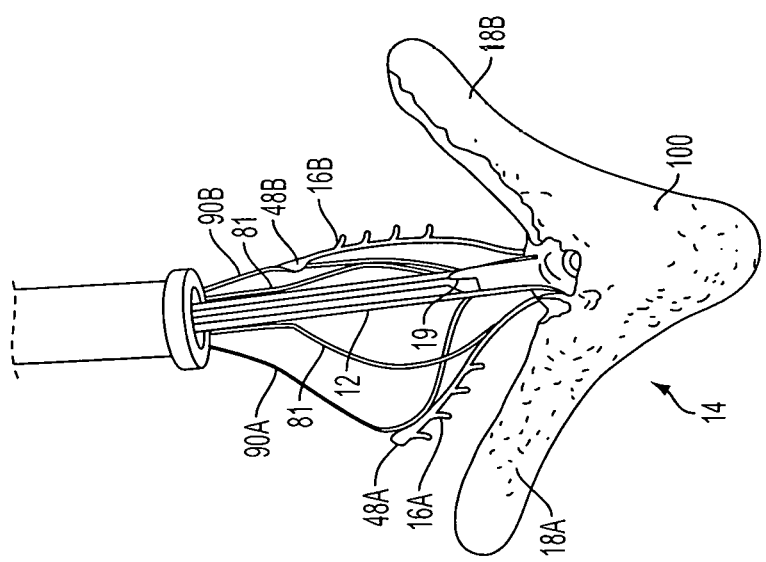

It may be desirable to provide for independent actuation of the proximal elements 16A and 16B. For example, as shown in FIG. 44, the proximal element actuator 90A is proximally retracted and rotates the proximal element 16A away from the distal element 18A, while the proximal element actuator 90B is pushed distally and rotates the proximal element 16B toward the distal element 18B. Similarly, as shown in FIG. 45, the proximal element actuator 90A is left alone, allowing the proximal element 16A to maintain the position it is biased toward, while the proximal element actuator 90B is proximally retracted, moving the proximal element 16B away from the distal element 18B.

Figure 47:
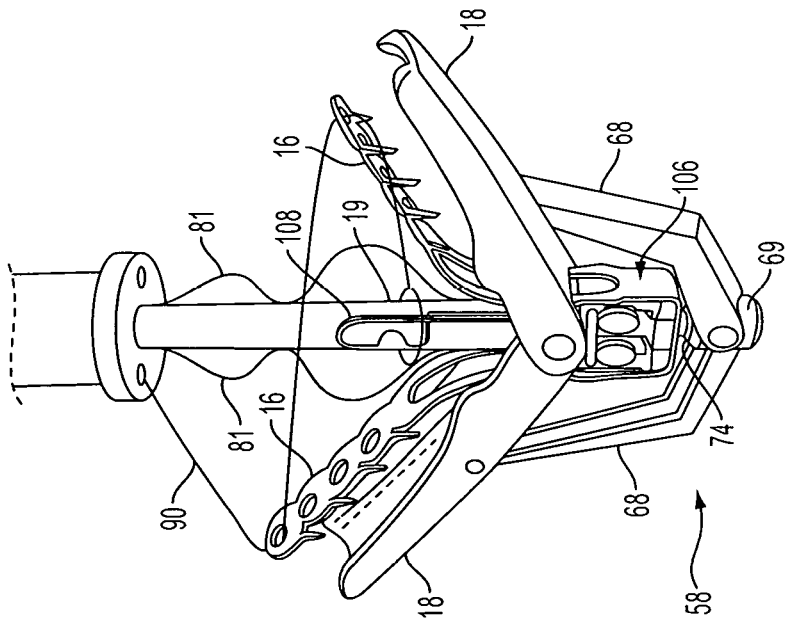
FIG. 47 illustrates another embodiment of a fixation device having a gripper pusher and independent actuation.

In another embodiment as illustrated in FIG. 47, the independent actuation of the proximal elements 16A and 16B is performed in a manner similar to the embodiment depicted in FIG. 46. However, as shown in FIG. 47, the proximal element actuators 90A and 90B are formed of a double loop configuration. The each proximal element actuator 90A and 90B exits the and returns through the nose 318 of the shaft 302 after being routed through the distal end of a corresponding one of the proximal elements 16A and 16B, and looped around the shaft 12 or coupling mechanism 19. This configuration provides the similar operational flexibility as the embodiment illustrated in FIG. 46, but permits removal of the proximal element actuators 90A and 90B before the coupling mechanism 19 is released from the shaft 12.

Figure 48:
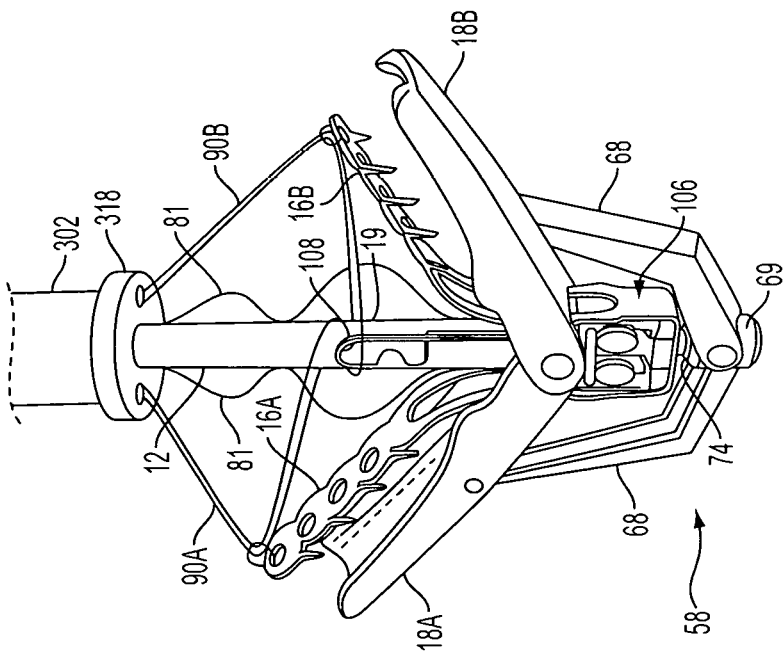
FIG. 48 illustrates another embodiment of a fixation device having a gripper pusher and independent actuation with a single actuator.

In another embodiment as illustrated in FIG. 48, a single proximal element actuator 90 is configured to perform sequential grasping in a similar manner to the embodiment depicted in FIG. 34. However, this embodiment also utilizes the gripper pusher 81 to provide for an extended range of movement in the open direction of the distal elements 18A and 18B. By virtue of the geometry of this configuration, each proximal element 16A and 16B may be independently actuated and the proximal element actuator 90 may be released in tandem with the separation of the coupling member 19. As illustrated in FIG. 35, due to the manner of routing the proximal element actuator 90, the resultant forces $F_1$ and $F_2$ are at different angles. These resultant forces and their directions are based on the tension on the proximal element 90 and the direction (angle) at which the proximal element actuator 90 approaches and extends away from a corresponding proximal element 16 A or 16B. Again, the force that causes a corresponding proximal element to move is the component of the force that is perpendicular to the length of a corresponding proximal element. This perpendicular component is represented by $F_{N1}$ and $F_{N2}$. Accordingly, for a given amount of tension in the proximal element actuator 90, proximal element 16A will receive more moving force than proximal element 16B. That means that proximal element 16B will remain closed as proximal element 16A opens, and proximal element 16B will open after proximal element 16A is fully opened. This allows for independent actuation of the proximal elements 16A and 16B using a single proximal element actuator 90. Additionally, however, in this embodiment, the included angle between the distal elements may greater than about 90°, preferably greater than about 110°, and more preferably greater than about 120°. Thus, in this embodiment, the fixation device is capable for independent actuation as well as a wide range of proximal element movement.

Coupling of Proximal Element Actuator

In many of the embodiments described above, the proximal element actuator 90 or proximal element actuators 90A and 90B includes an end that may be releasable coupled to the fixation device 14. Describe below are multiple embodiments showing various methods and structures for releasably coupling the proximal element actuators that may be applied to any of the embodiments described above.

Figure 49A:
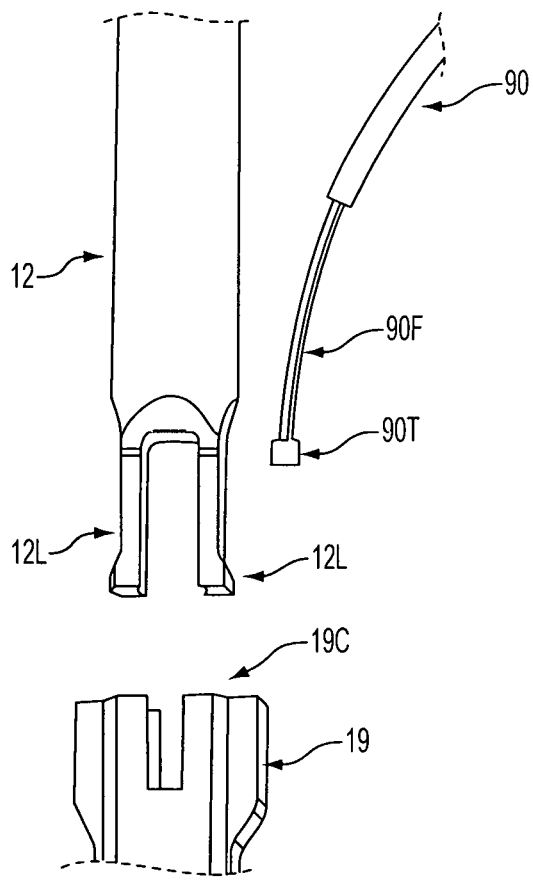
Figure 49B:
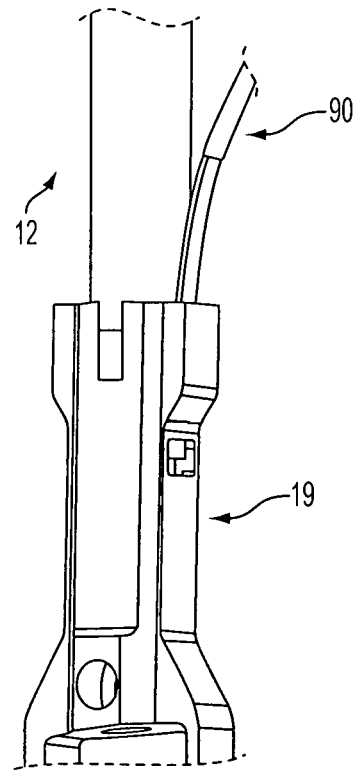
Figure 49C:
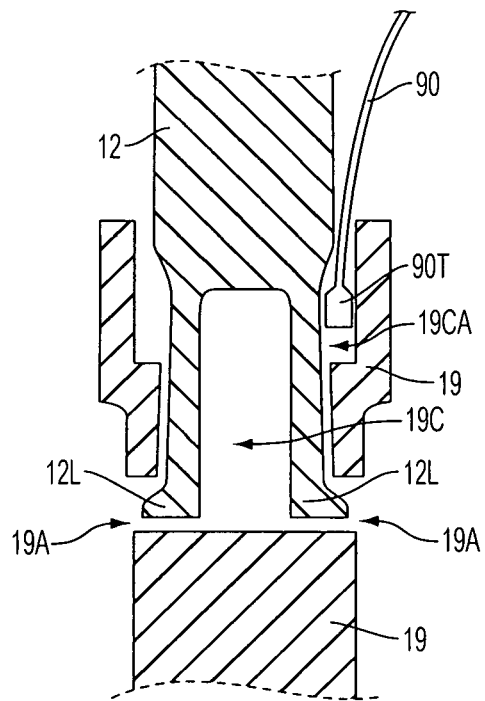

In many embodiments, the shaft 12 and the coupling member 19 are releaseably coupled together via an L-locking mechanism. For example, as shown in FIG. 49A, the proximal element actuator 90 may comprise a round T-shaped end 90T distal of the flat section 90F and the shaft 12 may comprise L-shaped ends 12L. As shown in the perspective view of FIG. 49B, the proximal element actuator 90 is releaseably coupled to the coupling member 19 when it and shaft 12 are placed into the channel 19C of the coupling member 19. As the shaft 12 is placed through the channel 19C, the L-shaped ends 12L are forced inwardly until they reach apertures 19A. At that point, the L-shaped ends 12L expand outwardly to fit into the apertures 19A, thereby locking the shaft 12 in place relative to the coupling member 19, as shown in cross-sectional view of FIG. 49C. The round T-shaped distal end 90T will typically be placed in the space 19CA prior to the shaft 12 being placed in the channel 19C. As shown in FIG. 49C, the round T-shaped distal end 90T then becomes trapped in the space or pocket 19CA between the channel 19C and a wider portion of the shaft 12 when the shaft is placed therein. Other L-locking or other locking mechanisms are described in commonly assigned U.S. patent application Ser. No. 12/393,452 entitled "Detachment Mechanism for Implantable Fixation Devices" and filed Feb. 26, 2009, the full contents of which are incorporated herein by reference.

The round T-shaped end 90T of the proximal element actuator 90 may also be used to facilitate releaseably coupling the proximal element line 90 to the shaft 12 and coupling member 19 is many other ways. For example, as shown in FIG. 50A, the L-shaped end 12L of the shaft 12 may comprise at least one proximal element line slot 12S. As shown in FIGS. 50C and 50D, the T-shape end 90T of the proximal element actuator 90 is slid into the proximal element line slot 12S. Then, the shaft 12 is placed into the coupling member 19, thereby also locking the proximal element line 90 in place. As shown in FIG. 50E, removing the shaft 12 from the coupling member 19 allows the proximal element line 90 to be slid out of the proximal element line slot 12S of L-shaped end 12L, thereby decoupling the proximal element actuator 90 from both the shaft 12 and the coupling device 19.

Figure 51A:
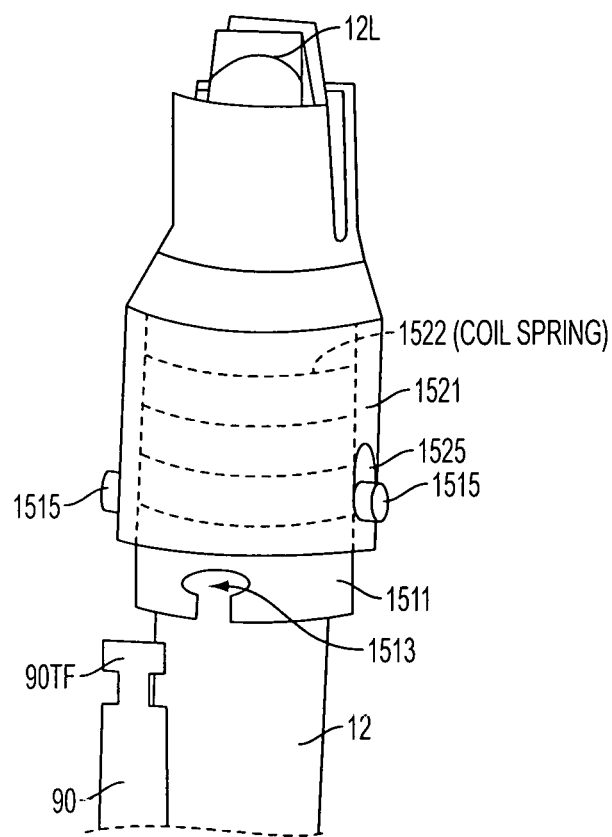
Figure 51B:
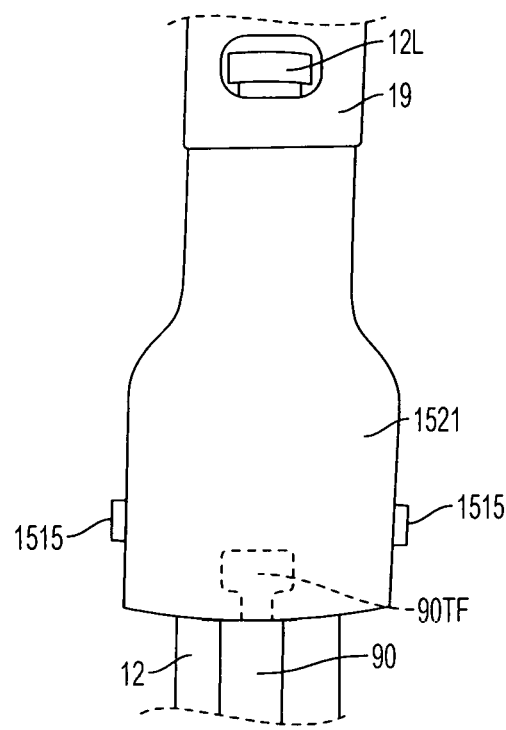

As shown in FIG. 51A, the proximal element actuator 90 may comprise a flat T-shaped end 90TF. The shaft 12 may further comprise an inner distal covering 1511 surrounding a distal portion of the shaft 12 and an outer distal covering 1521 surrounding the inner distal covering. The inner distal covering 1511 will typically be in a fixed position relative to the shaft 12 while the outer distal covering will be moveable relative to the shaft 12 at a range determined by tabs 1515 of inner distal covering 1511 placed through side channels 1525 of the outer distal covering 1521. To releaseably couple the proximal element actuator 90 to the shaft 12 and coupling line 19, the T-shaped end 90TF is fit into a T-shaped cutout 1513 of inner distal covering 1511, and when the shaft 12 is placed into the coupling device 19, the coupling device 19 pushes the outer distal covering 1521 over the inner distal covering 1511 to cover the T-shaped cutout 1513 as well as the T-shaped end 90TF, as shown in FIG. 51B. This compresses a coil spring 1522 placed between the inner distal covering 1511 and the outer distal covering 1521. When the fixation device 14 is released from the shaft 12, the outer distal covering 1521 moves distally due to the action of the coil spring 1522 to expose the T-shape cutout 1513 to release the proximal element actuator. In some embodiments, the outer distal covering 1521 may be spring loaded against the inner distal cover 1523 so that tend to maintain their relative positions shown in FIG. 51B.

Figure 52A:
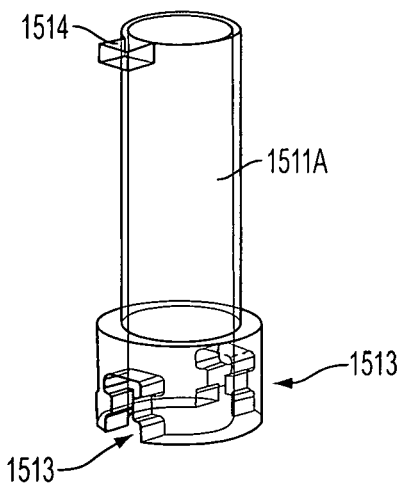
Figure 52B:
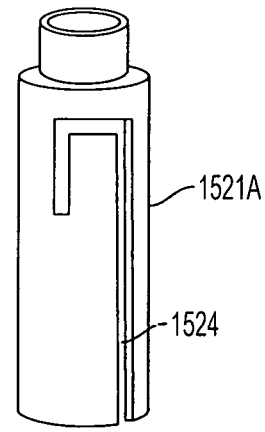
Figure 52C:
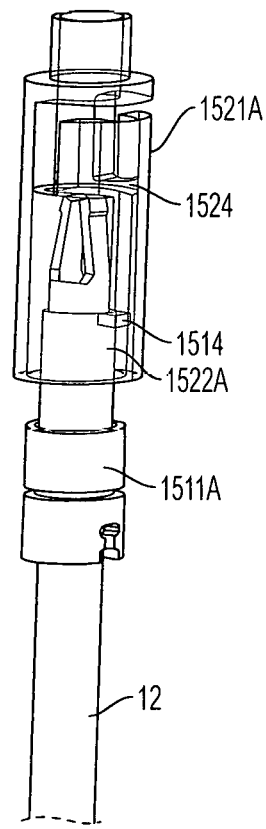
Figure 52D:
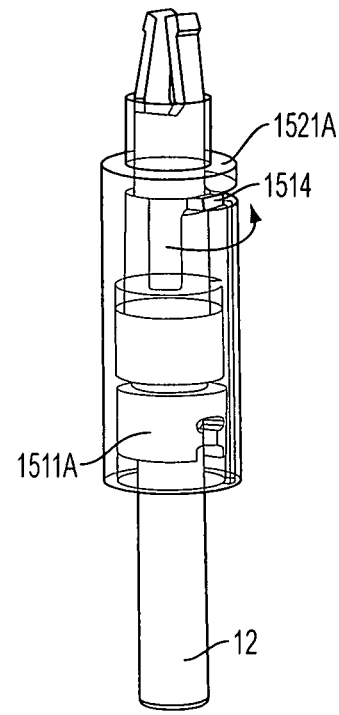
Figures 52E, 52F, 52G:
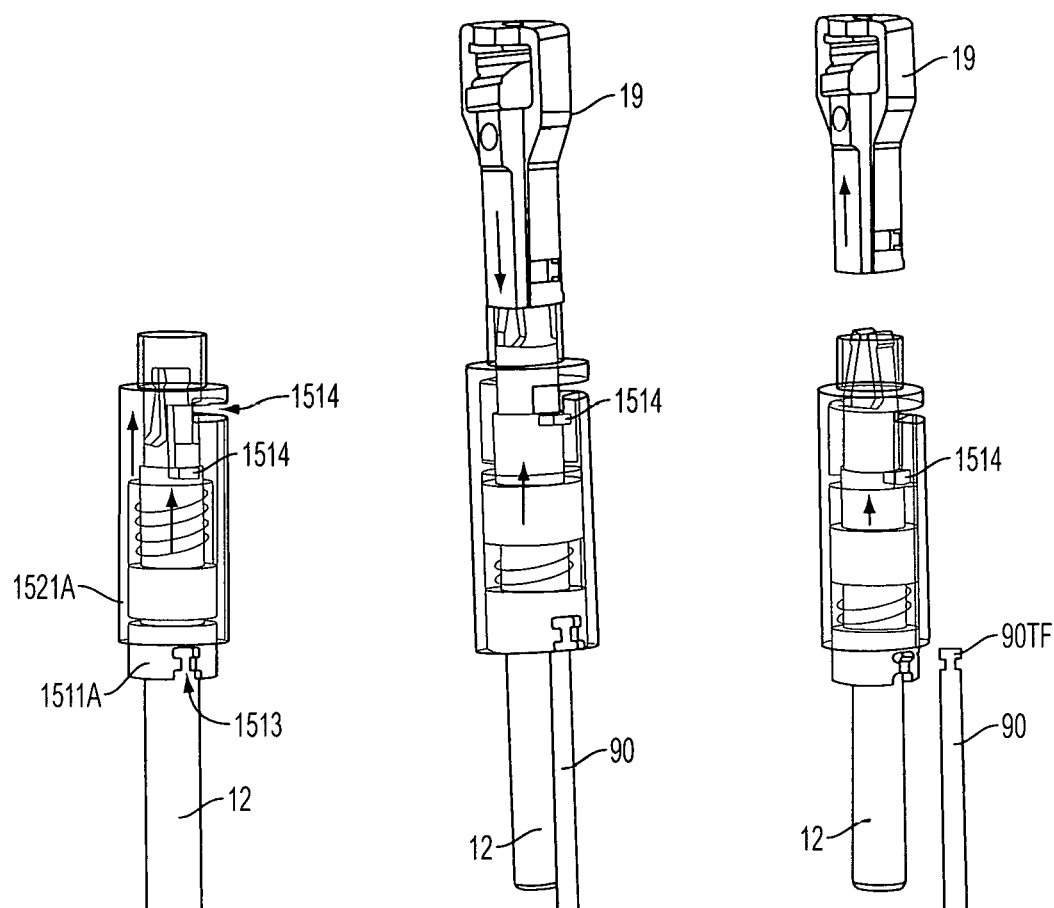

Proximal element actuators 90 may be releaseably coupled to the fixation device 14 in a variety of ways using variations of inner and outer distal collars over the distal portion of shaft 12, for example, as shown in FIGS. 52A to 52G. FIG. 15AB1 shows an inner distal collar 1511A having a pair of T-shaped cutouts 1513 and a tab 1514. FIG. 52C shows an outer distal collar 1521A having a channel 1524. The channel 1524 guides the inner distal collar 1511A via its tab 1514 as the inner distal collar 1511A is slid into the outer distal collar 1521A, for example as shown in FIGS. 52C through 52E. As in the embodiment shown in FIGS. 51A and 51B, to releaseably couple the proximal element actuators 90 to the shaft 12 and coupling member 19, the T-shaped end 90TF is fit into a T-shaped cutout 1513 of inner distal collar 1511S. When the shaft 12 is placed into the coupling device 19, the coupling member 19 pushes the outer distal collar 1521S over the inner distal collar 1511S to cover the T-shaped cutout 1513 as well as the T-shaped end 90TF, as shown in FIGS. 52F and 52G. This compresses the coil spring 1522A shown in FIG. 52C. When the fixation device 14 is released from the shaft 12, the outer distal covering 1521A moves distally due to the action of the coil spring 1522A to expose the T-shape cutout 1513A to release the proximal element actuator 90.

Figure 53:
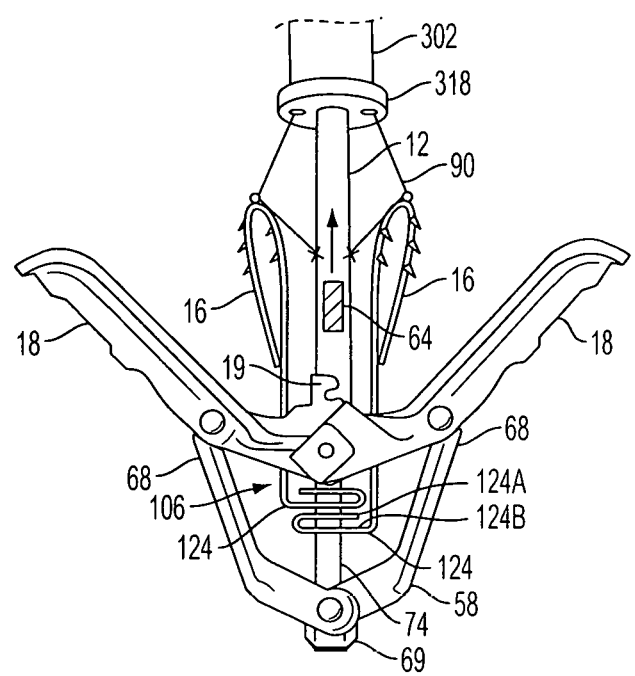
FIGS. 53, 54A-D, 55A-C and 56A-B illustrate an actuator rod and related components according an another embodiment of the fixation device.

In other embodiments, the proximal element actuators 90 may be releasably engaged with structures that are activated by removal of the actuator rod 64 that passed through the coupling member 19 and the shaft 12. As illustrated in FIG. 53 a stud 74 is releasably attached to the actuator rod 64 which passes through the coupling member 19 and the shaft 12 of the interventional tool 10. In this way, the actuator rod 64 is connectable with the fixation device and acts to manipulate the fixation device, typically opening and closing the distal elements. After the leaflets have been coapted, the actuator rod 64 is removed proximally from the stud 74 to release the coupling member 19, or alternatively, the L-lock mechanism described above. In the following embodiments, this action of the actuator rod 64 may be utilized to release the proximal element actuators 90.

Figure 54A:
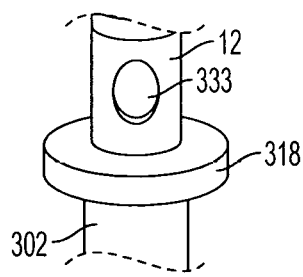
Figure 54B:
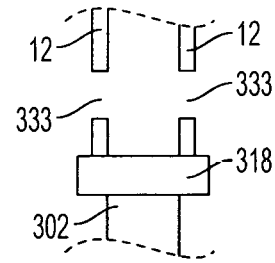
Figure 54C:
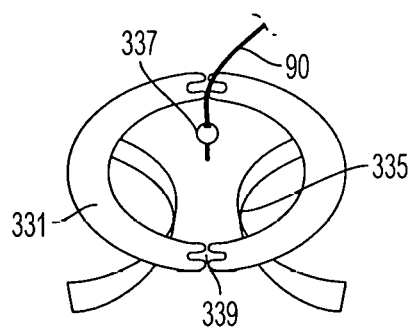
Figure 54D:
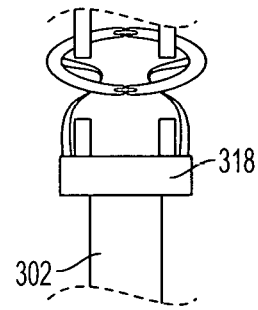

In one embodiment, as illustrated in FIGS. 54A through 54D and 55A through 55, spring members 331 are utilized in combination with the actuator rod 64 to hold and release the proximal element actuators 90. As shown in FIG. 54A, a portion of the shaft extending from the nose 318 has two windows 333 formed therein. Two spring members are positioned on the periphery of the shaft 12 adjacent a corresponding window so that a bent portion 335 extends into the actuator rod pathway formed within the shaft 12. A proximal side of these bent portions 335 may be fixed to the nose 318 or an external portion of the shaft 12. A distal side of each bent portion 335 is attached to a "C" shaped portion having a notch 339 formed at each end of the "C" shape. The corresponding end portions of one "C" shape portions on one spring are configured to abut the end portions of another spring so that the corresponding notches 339 can restrict the movement of a ball 337 at the end of either one of the proximal element actuators. FIG. 54C illustrates a position in which the "C" shaped portions are in contact to form a notch that prevents distal movement of the ball 337.

Figure 55A:
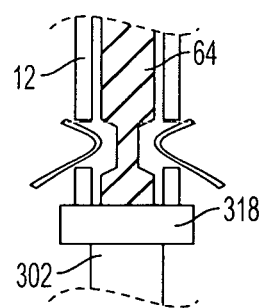
Figure 55B:
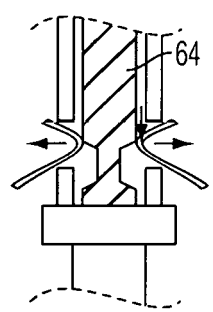
Figure 55C:
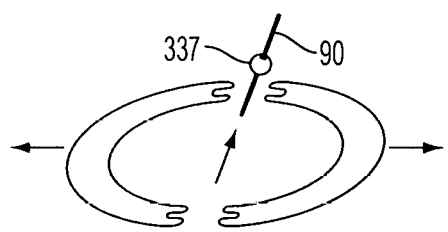

As illustrated in FIG. 55A, the actuator rod 64 is configured to have a tapered profile having a narrow portion and a wide portion. As the actuator rod 64 is moved proximally in FIG. 55B, a wide portion of the actuator rod 64 contacts the bent portions 335 to separate the corresponding "C" shaped portions of the adjacent spring members 331. This opens the notches 339 so that the ball 337 of the proximal actuator 90 is released as shown in FIG. 55C.

Figure 56A:
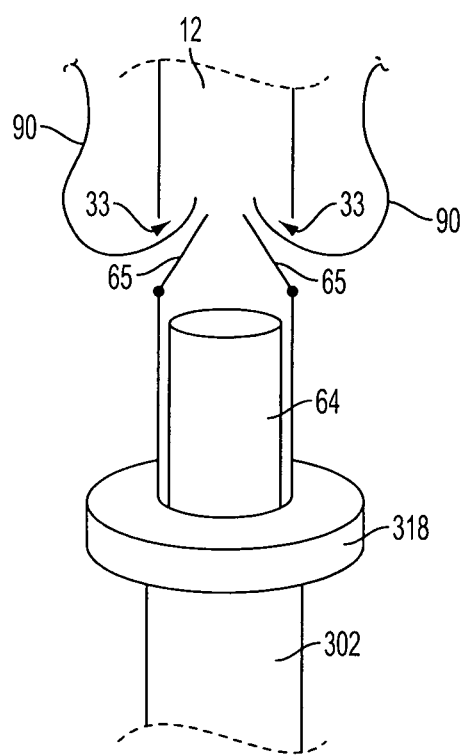
Figure 56B:
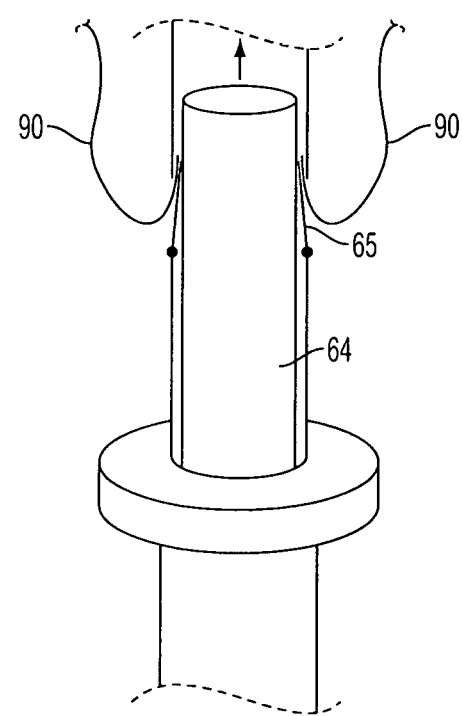

In another embodiment as illustrated in FIGS. 56A and 56B, the proximal element actuator 90 or proximal element actuators 90A and 90B may be releasably attached to the shaft 12 by using one or a set of liners 65 hingedly attached to the shaft 12. In this configuration, a pair of windows 33 (only one window is required in the case of a single proximal element actuator) is formed in the shaft 12. A liner is hingedly attached to the inside of the shaft 12 on a proximal side of each of the windows 33. As shown in FIG. 56A, when the actuator rod 64 is withdrawn proximally, the liners 65 move inwardly such that the proximal element actuators 90 are free to move. When the actuator rod 64 is in this position, the proximal element actuators 90 may be inserted into, or withdraw from, the windows 33. On the other hand, when the actuator rod 64 is moved distally as shown in FIG. 56B, the liners 65 are pressed outwardly against the inside surface of the shaft 12 to trap or pinch the proximal element actuators. This secures the proximal element actuators so that the proximal elements 16 can be moved independently. The proximal element actuators 90 are fixed to the shaft 12 until the actuator rod 64 is again moved proximally to the position shown in FIG. 56A.

While the methods and structures of releasably fixing the proximal element actuators 90 are shown above with either one or two proximal element actuators, it is possible to utilize or modify those structures for use with either a single or multiple proximal element actuators 90.

Releasably Fixing the Gripper Pushers

Figure 57:
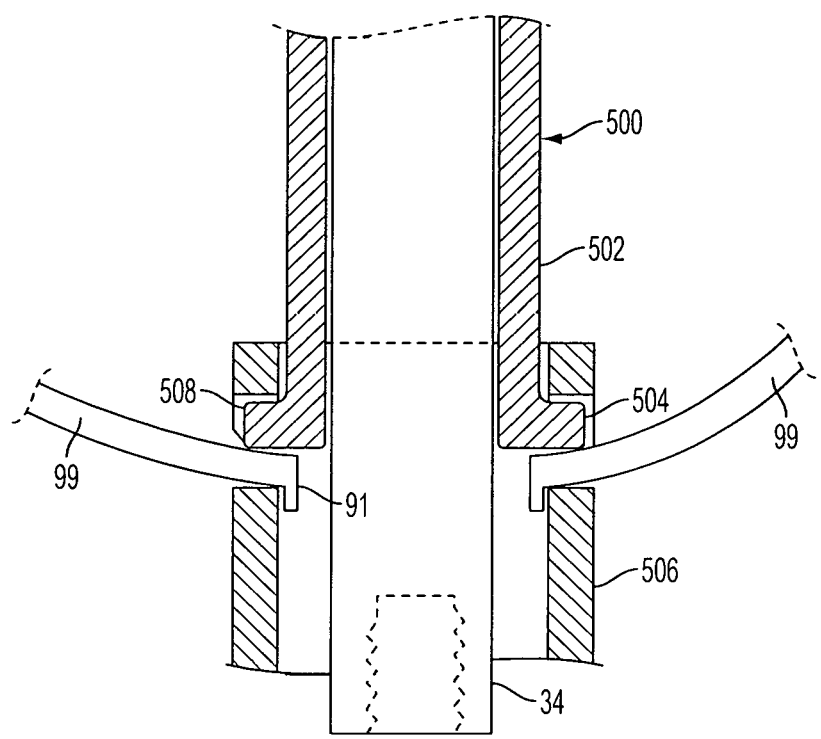
FIGS. 57 and 58 illustrate an embodiment for releasably coupling a gripper pusher to a fixation device.
Figure 58:
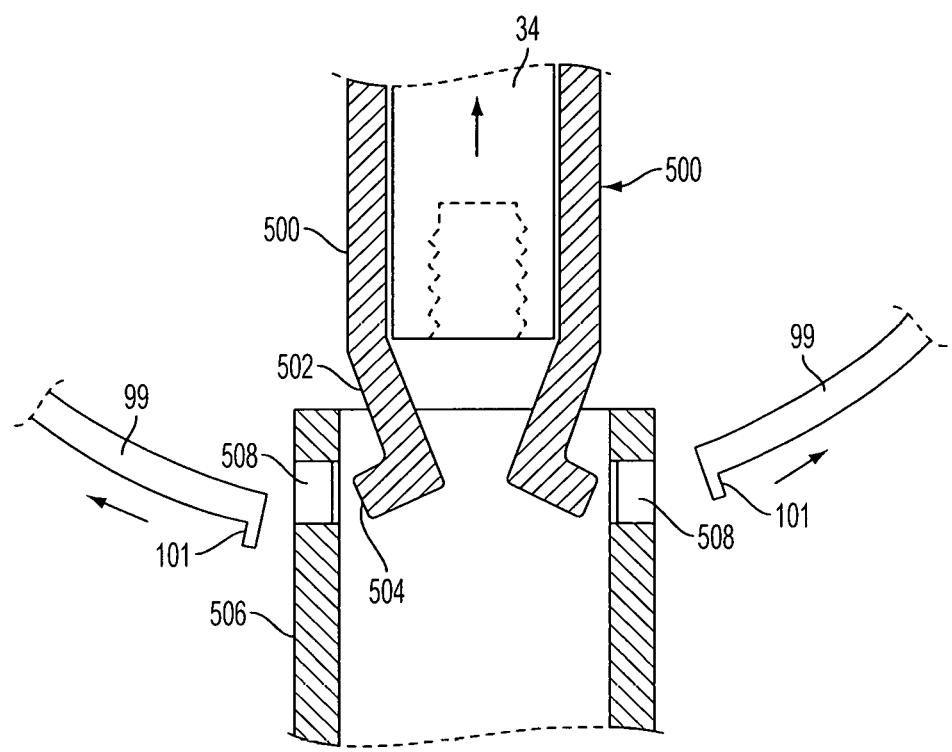

As set forth above, FIG. 39 highlights the gripper pusher 83 which preferably includes two spring arms 99. Each arm 99 is formed from wire or machined from a sheet or other stock material and in this embodiment has a rectangular cross-section, although other cross-sections are also contemplated. In the embodiment of FIG. 39, a distal portion 91 of each arm 99 has a notched region 93 forming a pair of fingers that can engage with a boss or other attachment mechanism on the fixation device. The notch may be released from the boss when the fixation device 14 is detached from the delivery catheter shaft 12. FIGS. 57 and 58 show an alternative embodiment for releasably securing the arms 99 of the gripper pusher 83 in combination with an L-lock configuration.

FIGS. 57 and 58 illustrate an alternate embodiment to the mating surface 32 illustrated in FIG. 6A. Here, upper shaft 500 is releasably coupled with lower shaft 506 with a detent mechanism 504, 508. The upper and lower shafts in this embodiment are generally tubular shaped although one of skill in the art will appreciate that other configurations are possible. The detent mechanism in this exemplary embodiment includes one or more spring arms 502 integrally formed on tubular upper shaft 500 and one or more receptacles 508 sized to receive the spring arms 502. Tubular upper shaft 500 is integrally formed with one or more spring arms 502 having a flange-like engagement surface 504 at a distal end thereof. The spring arms 502 are preferably biased inwardly, i.e., toward the interior of the shaft 500. Detachable tubular lower shaft 506 features one or more receptacles, here apertures 508 are configured to receive and mate with the engagement surface 504 of the spring arm 502 and an engagement surface of the arm 99 of the gripper pusher 83. The apertures 508 may extend all the way through the wall of the lower shaft 506 and are sized to snuggly fit both the engagement surface 504 of the spring arms 502 and the engagement surface 101 at the distal end 91 of the arms 99. To releasably couple the arms 99 to the tubular lower shaft 506, the engagement surfaces 101 of the arms 99 are fitted into a corresponding aperture 508. Then, a snuggly fitting rod 34 (such as actuator rod 64) is inserted through the tubular shafts 500, 506 outwardly deflecting the inwardly biased spring arm(s) 502 such that the engagement surface 504 is pushed into engagement with a corresponding receptacle 508 and arm 99 thereby coupling the gripper pusher 83 and the upper shaft 500 to the lower shaft 506.

FIG. 58 illustrates detachment of the lower shaft 506 from the upper shaft 500. This is achieved by retracting the rod 34 to a position above the spring arm(s) 502 which allows the inwardly biased engagement surface 504 to disengage from the receptacle 508 allowing the arms 99 of the gripper pusher 83 to separate along with the shafts 500, 506.

While the foregoing is a complete description of the preferred embodiments of the invention, various alternatives, substitutions, additions, modifications, and equivalents are possible without departing from the scope of the invention. For example, in many of the above-described embodiments, the invention is described in the context of approaching a valve structure from the upstream side—that is, the atrial side in the case of a mitral valve. It should be understood that any of the foregoing embodiments may be utilized in other approaches as well, including from the ventricular or downstream side of the valve, as well as using surgical approaches through a wall of the heart. Moreover, the invention may be used in the treatment of a variety of other tissue structures besides heart valves, and will find usefulness in a variety of tissue approximation, attachment, closure, clamping and ligation applications, some endovascular, some endoscopic, and some open surgical.

Again, although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A system for fixation of leaflets of a heart valve comprising:
   an implantable fixation device comprising
      a first arm and a second arm,
      a first gripping element moveable relative to the first arm between a first position and a second position, and
      a second gripping element moveable relative to the second arm between a first position and a second position; and
   a delivery device comprising
      a catheter having a proximal end portion and a distal end portion, the catheter defining at least one lumen extending from the proximal end portion to the distal end portion,
      a first gripping element line extending through the at least one lumen, the first gripping element line coupled to the first gripping element and actuatable to move the first gripping element between the first and second positions, the first gripping element line having a proximal end portion and a distal end portion, the distal end portion of the first gripping element line being releasably coupled to a distal end portion of an elongate delivery shaft, and
      an actuator rod extending through a lumen of the elongate delivery shaft to the implantable fixation device to actuate the first and second arms;
   wherein the elongate delivery shaft defines at least one opening and the distal end portion of the first gripping element line is fixed in the at least one opening with the actuator rod extended to the implantable fixation device.

2. The system of claim 1, further comprising a second gripping element line extending through the at least one lumen, the second gripping element line coupled to the second gripping element and actuatable to move the second gripping element between the first and second positions.

3. The system of claim 2, wherein the first gripping element line and the second gripping element line are independently actuatable.

4. The system of claim 1, wherein the distal end portion of the elongate delivery shaft is releasably coupled to a proximal end portion of the implantable fixation device.

5. The system of claim 4, wherein the delivery shaft comprises a liner disposed inside of the delivery shaft configured to occlude the at least one opening, and wherein the first gripping element line is fixed by the liner when the actuator rod is extended into the implantable fixation device and released by the liner when the actuator rod is withdrawn from the implantable fixation device.

6. The system of claim 5, wherein the liner is hingedly attached to the delivery shaft.

7. The system of claim 4, wherein the delivery shaft comprises spring members disposed on the exterior of the delivery shaft having bent portions that extend into the at least one opening, each spring member having a notched end, wherein the notched ends of the spring members abut to form an opening sized to releasably engage the first gripping element line.

8. The system of claim 7, wherein the actuator rod has a taper shape configured to press the bent portions when the actuator rod is withdrawn from the implantable fixation device to release the first gripping element line by causing the notched ends to separate.

9. The system of claim 1, wherein the first gripping element line is released from the implantable fixation device when the elongate delivery shaft is decoupled from the implantable fixation device.

10. The system of claim 1, further comprising a gripper pusher releasably coupled to the implantable fixation device adjacent the first and second gripping elements, the gripper pusher having an expanded configuration and a collapsed configuration, wherein in the expanded configuration the gripper pusher engages the first and second gripping elements and advances the first and second gripping elements toward the first and second arms, respectively.

11. The system of claim 10, wherein in the collapsed configuration the gripper pusher has a reduced radial profile relative to the gripper pusher radial profile in the expanded configuration thereby allowing the first and second gripping elements to move away from the first and second arms, respectively.

12. The system of claim 1, further comprising a gripper pusher adjacent the first and second gripping elements.

13. The system of claim 12, wherein the distal end portion of the elongate delivery shaft is releasably coupled to a proximal end portion of the implantable fixation device.

14. The system of claim 13, wherein a distal end portion of the gripper pusher is releasably attached to the implantable fixation device.

15. The system of claim 14, wherein the gripper pusher comprises a pair of elongate flexible arms and a shaft of the implantable fixation device includes apertures for releasably engaging a distal end portion of each of the pair of elongate flexible arms.

16. The system of claim 15, wherein a proximal end portion of the implantable fixation device comprises a pair of apertures, wherein the distal end portion of the elongate delivery shaft comprises a pair of L-shaped ends resiliently biased to fit into the pair of apertures, wherein the distal end portions of the pair of elongate flexible arms are releasably coupled to the implantable fixation device by being fitted into the apertures and with the pair of L-shaped ends.

17. The system of claim 16, wherein the system is configured such that withdrawal of the actuator rod from the implantable fixation device releases the L-shaped ends and the distal end portions of the pair of elongate flexible arms from the implantable fixation device.

18. A fixation system for engaging tissue comprising:
an implantable fixation device comprising
  a first arm and a second arm,
  a first gripping element moveable relative to the first arm between a first position and a second position, and
  a second gripping element moveable relative to the second arm between a first position and a second position; and
a delivery device comprising
  a catheter having a proximal end portion and a distal end portion, the catheter defining at least one lumen extending from the proximal end portion to the distal end portion,
  a first gripping element line extending through the at least one lumen, the first gripping element line coupled to the first gripping element and actuatable to move the first gripping element between the first and second positions, the first gripping element line having a proximal end portion and a distal end portion, the distal end portion of the first gripping element line being releasably coupled to a distal end portion of an elongate delivery shaft,
  a second gripping element line extending through the at least one lumen, the second gripping element line coupled to the second gripping element and actuatable to move the second gripping element between the first and second positions, the second gripping element line having a proximal end portion and a distal end portion, the distal end portion of the second gripping element line being releasably coupled to the distal end portion of the elongate delivery shaft, and
  an actuator rod extending through a lumen of the elongate delivery shaft to the implantable fixation device to actuate the first and second arms;
wherein the first gripping element line and the second gripping element line are actuatable independently of each other; and
wherein the elongate delivery shaft defines an opening and the distal end portion of the first gripping element line is fixed in the opening with the actuator rod extended to the implantable fixation device.

19. The fixation system of claim 18, wherein the first gripping element line is released when the actuator rod is withdrawn from the implantable fixation device.

20. The fixation system of claim 19, wherein the second gripping element line is disposed in the opening and fixed when the actuator rod is extended into the implantable fixation device.

21. The fixation system of claim 20, wherein the second gripping element line is released when the actuator rod is withdrawn from the implantable fixation device.

22. A method for fixing tissue, the method comprising:
providing an implantable fixation device having
  a first arm and a second arm,
  a first gripping element moveable relative to the first arm between a first position and a second position,
  a second gripping element moveable relative to the second arm between a first position and a second position, and
  a locking mechanism moveable between a locked position and an unlocked position;
positioning the fixation device using a delivery device such that tissue is disposed between the first gripping element and the first arm, wherein the delivery device comprises:
  a catheter having a proximal end portion and a distal end portion, the catheter defining at least one lumen extending from the proximal end portion to the distal end portion,
  a first gripping element line extending through the at least one lumen, the first gripping element line coupled to the first gripping element and actuatable to move the first gripping element between the first and second positions, the first gripping element line having a proximal end portion and a distal end portion, the distal end portion of the first gripping element line being releasably coupled to a distal end portion of an elongate delivery shaft, and
  an actuator rod extending through a lumen of the elongate delivery shaft to the implantable fixation device to actuate the first and second arms,
  wherein the elongate delivery shaft defines at least one opening and the distal end portion of the first gripping element line is fixed in the at least one opening with the actuator rod extended to the implantable fixation device;
activating the first gripping element line to actuate the first gripping element to grasp tissue between the first gripping element and the first arm; and
withdrawing the actuator rod to release the first gripping element line.

23. The method of claim 22, further comprising activating a second gripping element line to actuate the second gripping element to grasp tissue between the second gripping element and the second arm, while the first gripping element and the first arm are engaged with tissue.

\* \* \* \* \*